US012694972B2

(12) United States Patent
Ocampo et al.

(10) Patent No.: US 12,694,972 B2
(45) Date of Patent: Jul. 28, 2026

(54) PREDICTING ACTIONABLE MUTATIONS FROM DIGITAL PATHOLOGY IMAGES

(71) Applicants:Genentech, Inc., South San Francisco, CA (US); Hoffmann-La Roche Inc., Little Falls, NJ (US); Ventana Medical Systems, Inc., Tucson, AZ (US)

(72) Inventors: Paolo Santiago Syjuco Ocampo, Los Altos Hills, CA (US); Bernhard Stimpel, Basel (CH); Yao Nie, Sunnyvale, CA (US); Fahime Sheikhzadeh, Tucson, AZ (US); Xiao Li, Foster City, CA (US); Przemyslaw Szostak, Basel (CH); Prasanna Porwal, Akola (IN); Faranak Aghaei, Tucson, AZ (US)

(73) Assignees: Genentech, Inc., South San Francisco, CA (US); Hoffmann-La Roche Inc., Little Falls, NJ (US); Ventana Medical Systems, Inc., Tucson, AZ (US)

( * ) Notice: Subject to any disclaimer, the term of this patent is extended or adjusted under 35 U.S.C. 154(b) by 226 days.

(21) Appl. No.: 18/506,905

(22) Filed: Nov. 10, 2023

(65) Prior Publication Data

US 2024/0087726 A1     Mar. 14, 2024

Related U.S. Application Data

(63) Continuation of application No. PCT/US2022/029329, filed on May 14, 2022.
(Continued)

(51) Int. Cl.
G16H 30/40      (2018.01)
G06T 7/00       (2017.01)
(Continued)

(52) U.S. Cl.
CPC .......... *G16H 30/40* (2018.01); *G06T 7/0012* (2013.01); *G16H 20/00* (2018.01); *G16H 50/20* (2018.01)

(58) Field of Classification Search
CPC ......... G06T 7/0012; G06T 2207/30096; G06T 2207/10056; G06T 2207/30024;
(Continued)

(56) References Cited

U.S. PATENT DOCUMENTS 8,559,693  B2 *  10/2013  MacAulay ............ G06T 7/0012
                                              382/128
11,164,312  B2 *  11/2021  Saltz .................... G06V 10/267
(Continued)

FOREIGN PATENT DOCUMENTS

WO        2017079763  A1     5/2017

OTHER PUBLICATIONS

Hassoun, M.H. (Jul. 1996). Fundamentals of Artificial Neural Networks 1995, Book Review, MIT 42(4):1322-1324.
(Continued)

*Primary Examiner* — Courtney Joan Nelson
(74) *Attorney, Agent, or Firm* — MORRISON & FOERSTER LLP

(57)                ABSTRACT

A method includes accessing a digital pathology image that depicts tumor cells sampled from a subject. A plurality of patches may be selected from the digital pathology image, wherein each of the patches depicts tumor cells. A mutation prediction may be generated for each of the patches, wherein the mutation prediction represents a prediction of a likelihood that an actionable mutation appears in the patch. Based on the plurality of mutation predictions, a prognostic prediction related to one or more treatment regimens for the subject may be generated. The prognostic prediction may be based on determining one or more mutational contexts of the
(Continued)

digital pathology image as an unknown driver or a tumor suppressor, an oncogene driver mutation, or a gene fusion.

20 Claims, 45 Drawing Sheets

Related U.S. Application Data

(60) Provisional application No. 63/332,674, filed on Apr. 19, 2022, provisional application No. 63/239,287, filed on Aug. 31, 2021, provisional application No. 63/188,963, filed on May 14, 2021.

(51) Int. Cl.
  G16H 20/00 (2018.01)
  G16H 50/20 (2018.01)

(58) Field of Classification Search
  CPC ........... G06T 11/00; G06T 2207/20021; G06T 2219/004; G06N 3/0464; G06N 20/00; G06V 2201/03; G06V 10/44; G06V 20/69; G16H 30/40; G16H 50/20; G16H 20/00; G16H 10/60; G16H 70/60
  See application file for complete search history.

(56) References Cited

U.S. PATENT DOCUMENTS

| | | | |
|---|---|---|---|
| 2020/0211189 A1 | 7/2020 | Yip et al. | |
| 2021/0090694 A1* | 3/2021 | Colley | G16B 30/00 |
| 2021/0142904 A1* | 5/2021 | Michuda | G16H 50/20 |
| 2023/0177682 A1* | 6/2023 | Xiao | G16H 50/30 |
| | | | 382/133 |

OTHER PUBLICATIONS

Larochelle, H. et al. (2009). "Exploring Strategies for Training Deep Neural Networks," J. Mach. Learn. Res. 1:1-40.
Vincent, P. et al. (2010). "Stacked Denoising Autoencoders: Learning Useful Representations in A Deep Network with a Local Denoising Criterion," J. Mach. Learn. Res. 11:3371-3408.

\* cited by examiner

<u>200</u>

300

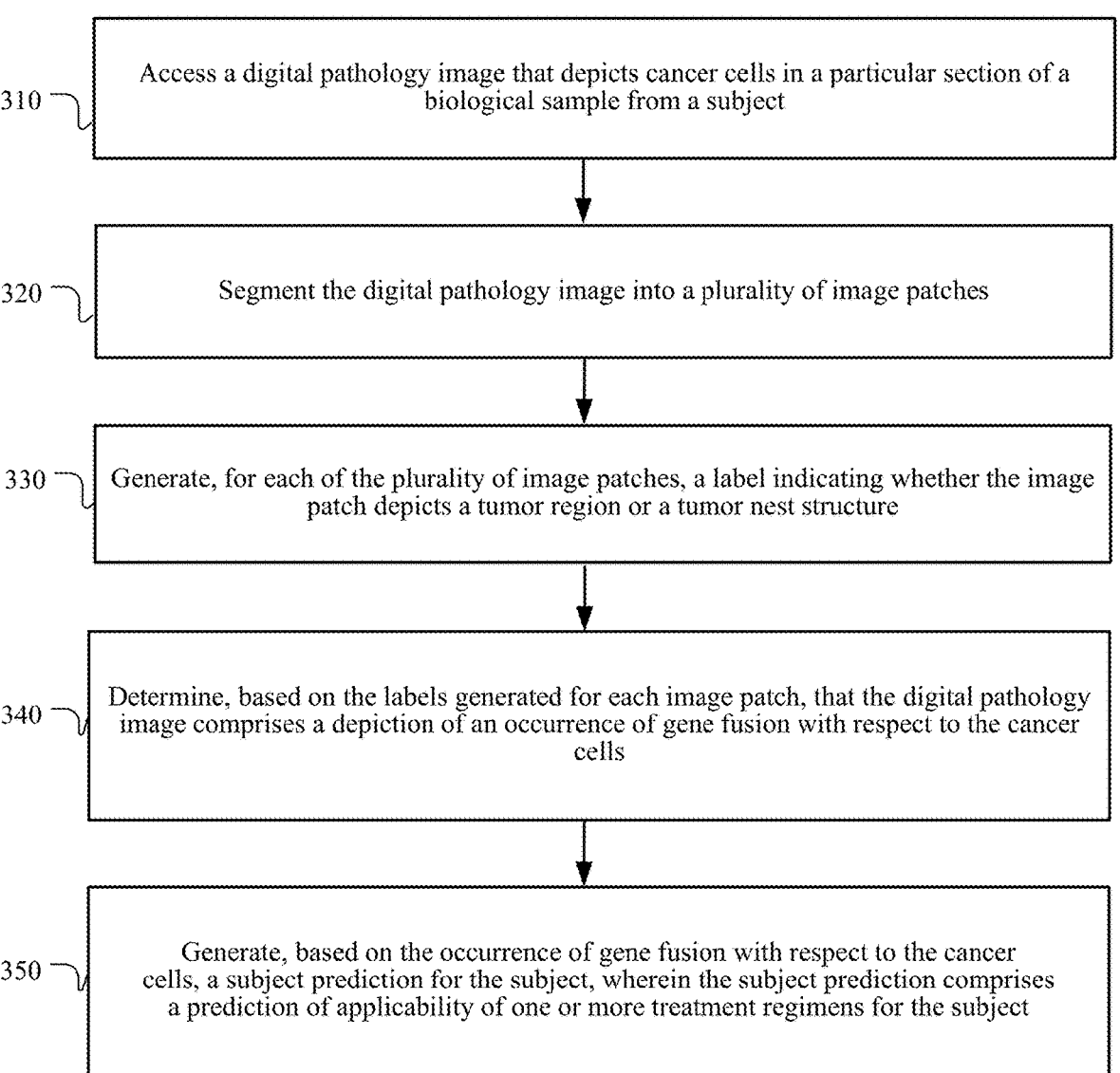

310    Access a digital pathology image that depicts cancer cells in a particular section of a biological sample from a subject 320    Segment the digital pathology image into a plurality of image patches 330    Generate, for each of the plurality of image patches, a label indicating whether the image patch depicts a tumor region or a tumor nest structure 340    Determine, based on the labels generated for each image patch, that the digital pathology image comprises a depiction of an occurrence of gene fusion with respect to the cancer cells 350    Generate, based on the occurrence of gene fusion with respect to the cancer cells, a subject prediction for the subject, wherein the subject prediction comprises a prediction of applicability of one or more treatment regimens for the subject

*FIG. 3*

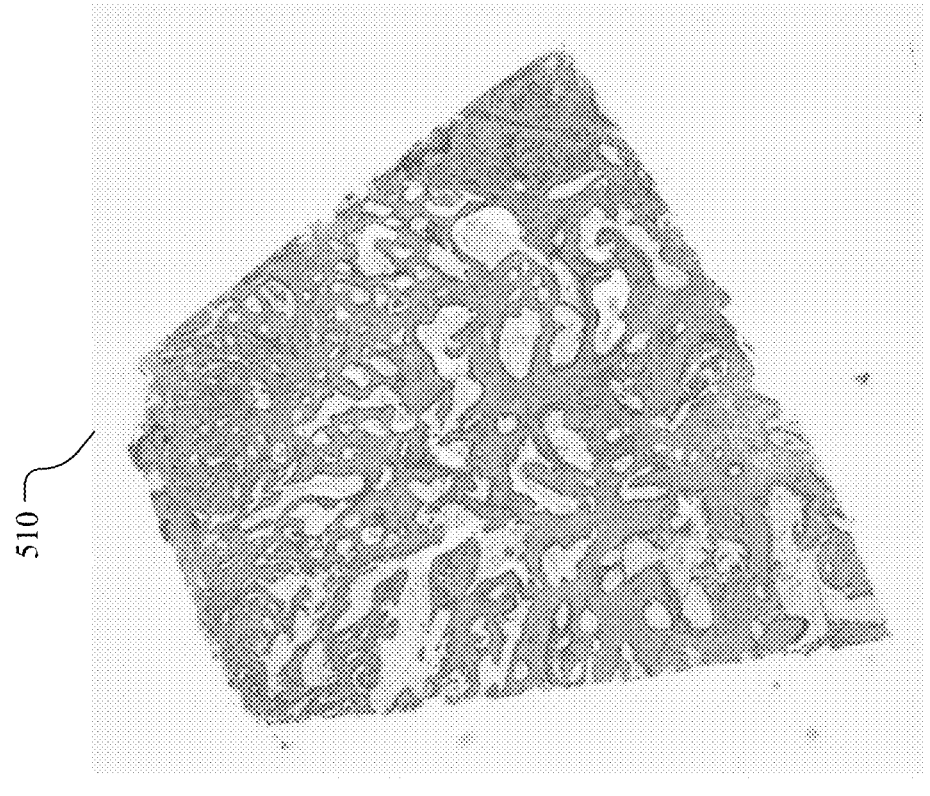
EGFR+ lung adenocarcinoma
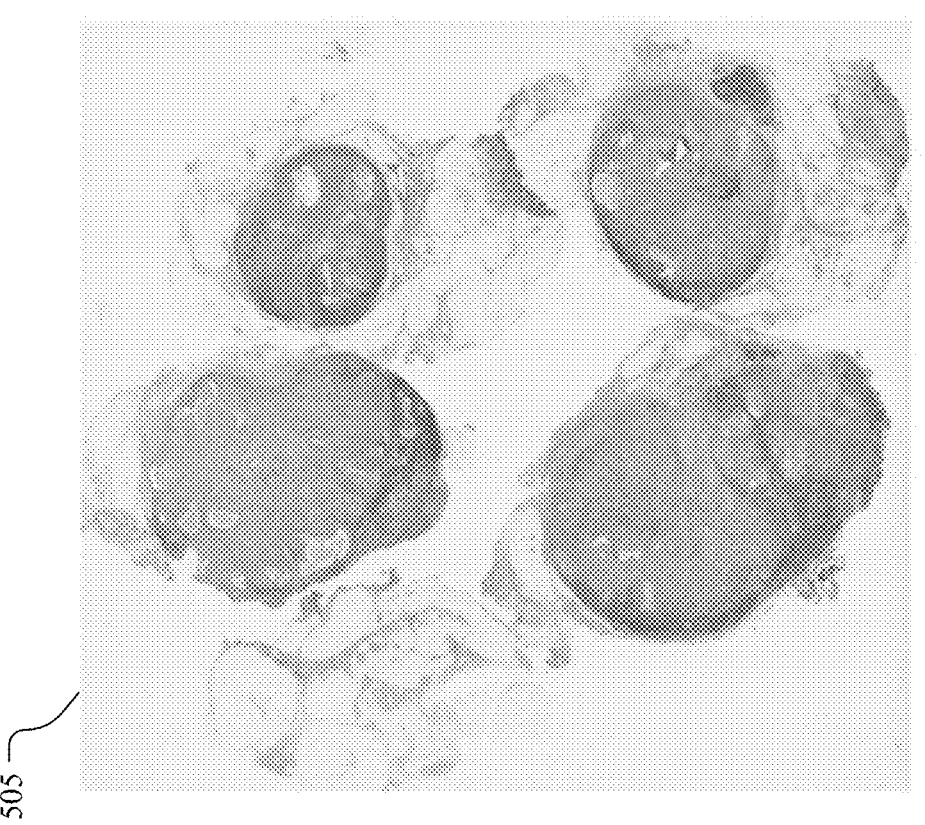
ROS1+ metastatic lung adenocarcinoma
*FIG. 5A*

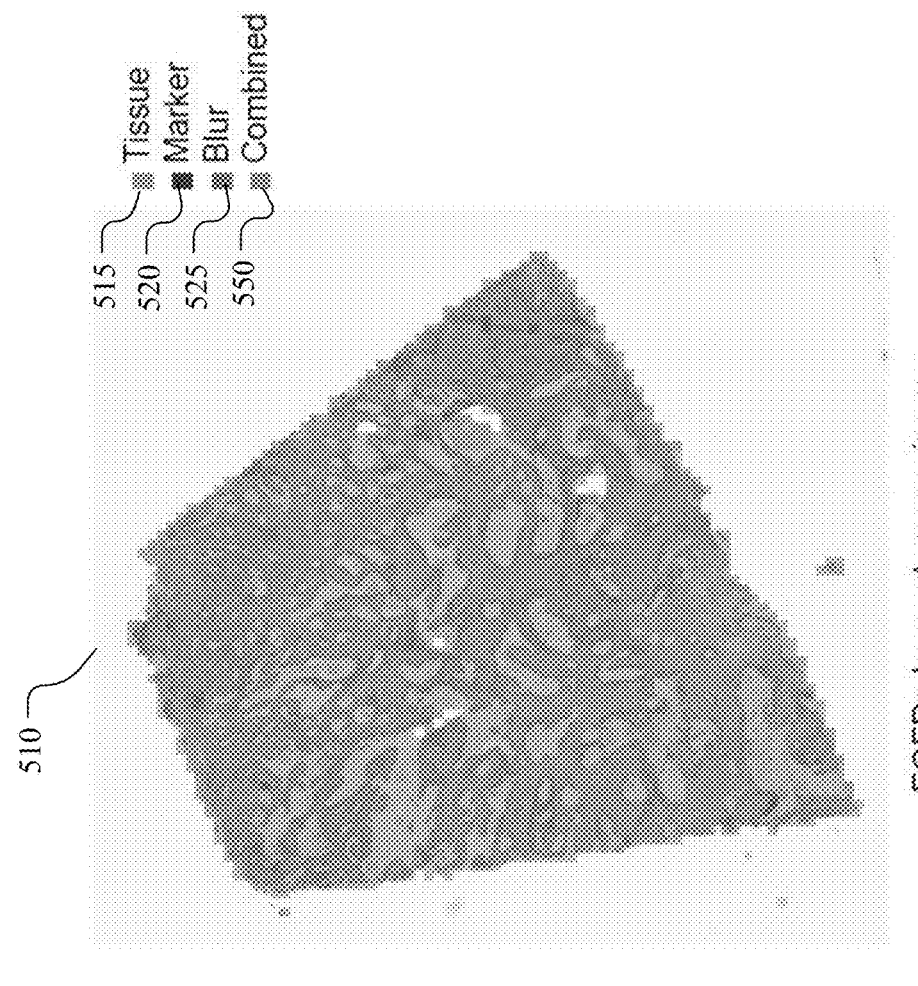
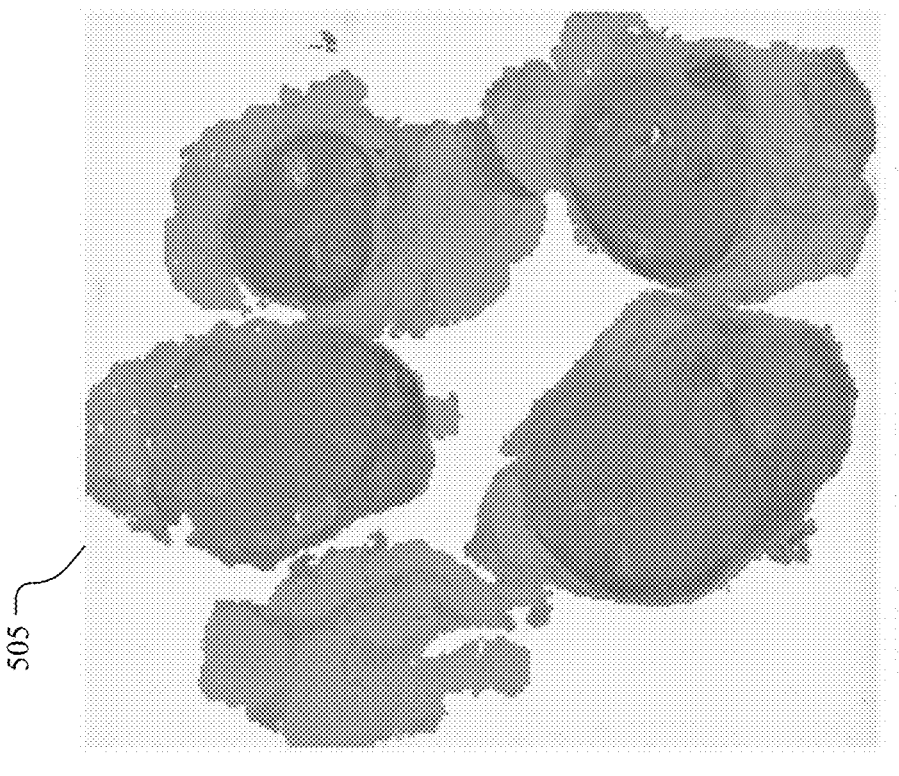
515 Tissue
520 Marker
525 Blur
550 Combined
510
505
EGFR+ lung adenocarcinoma
ROS1+ metastatic lung adenocarcinoma
*FIG. 5B*

Normal
Tumor
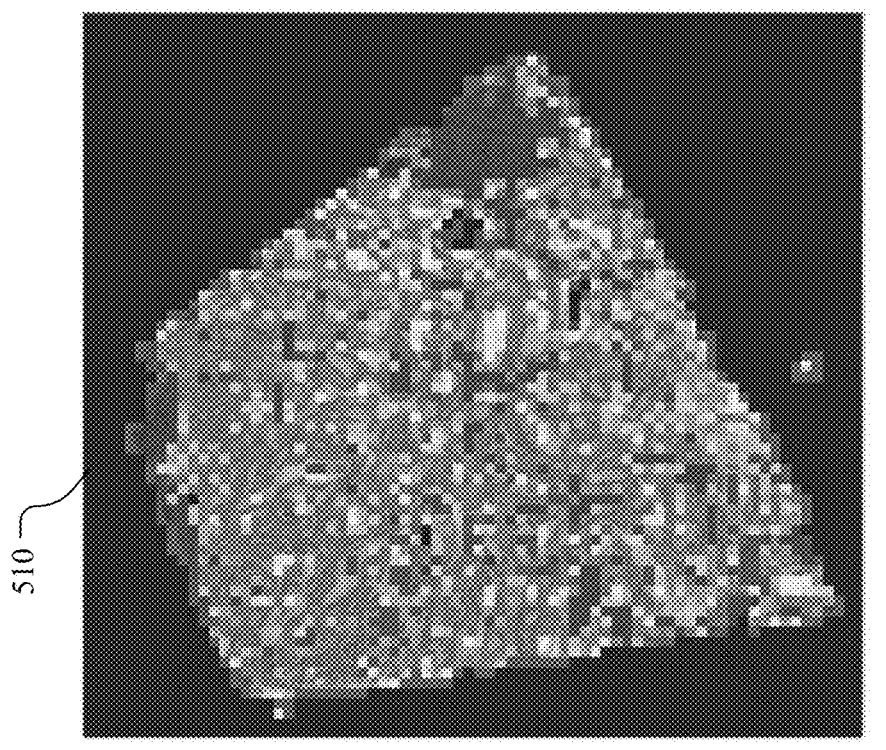
EGFR+ lung adenocarcinoma
510
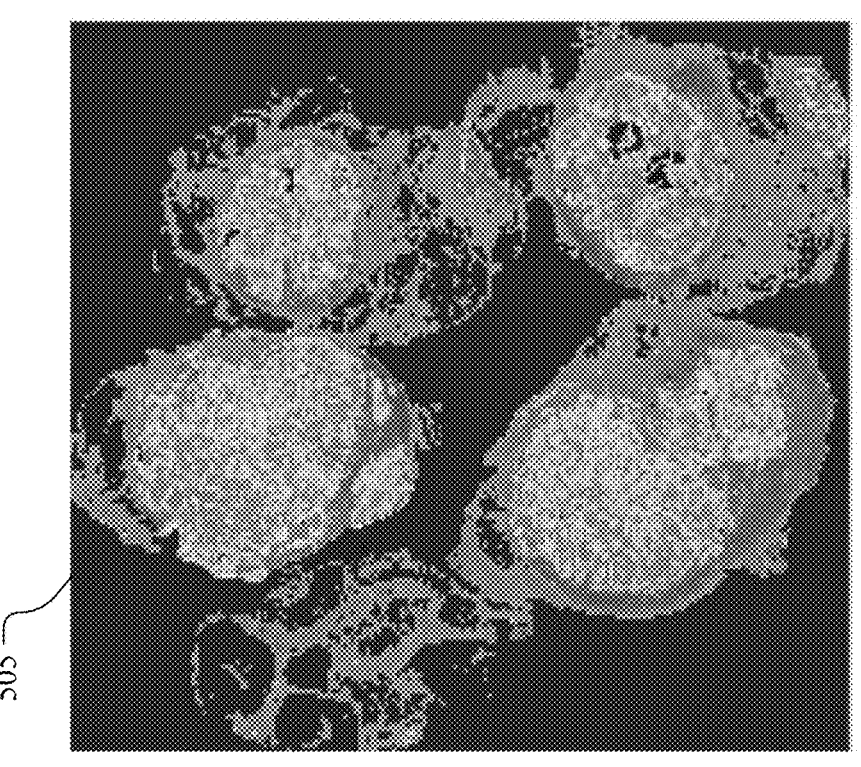
ROS1+ metastatic lung adenocarcinoma
505
*FIG. 5C*

Fusion-
Fusion+
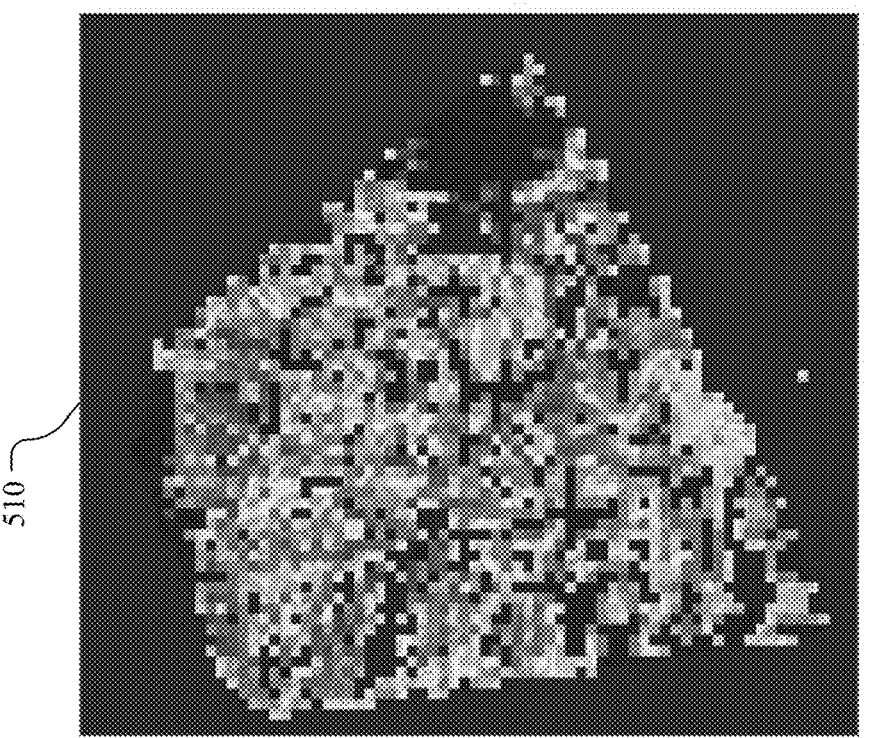
510
EGFR+ lung adenocarcinoma
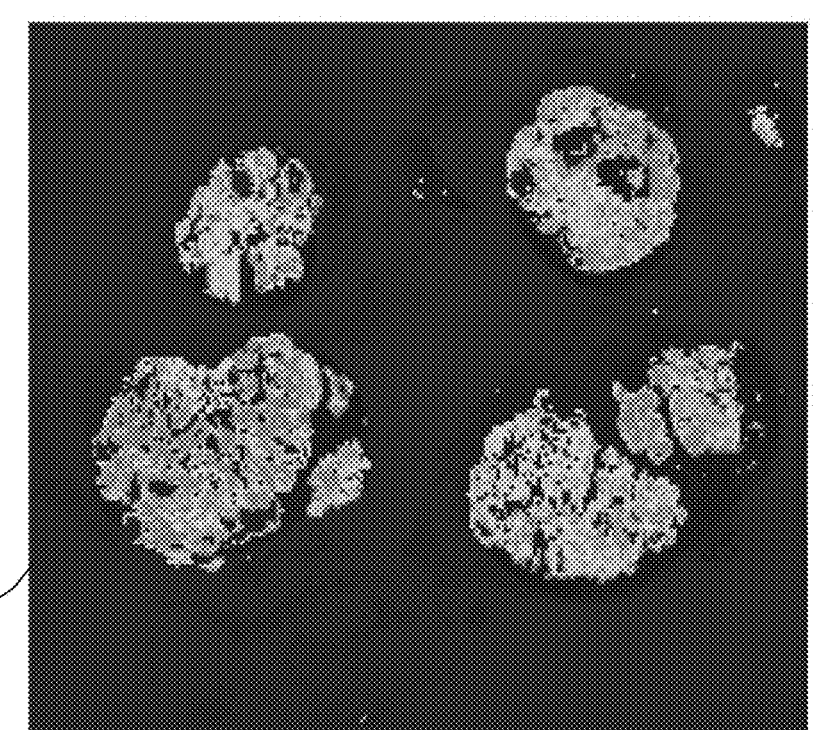
505
ROS1+ metastatic lung adenocarcinoma
*FIG. 5D*

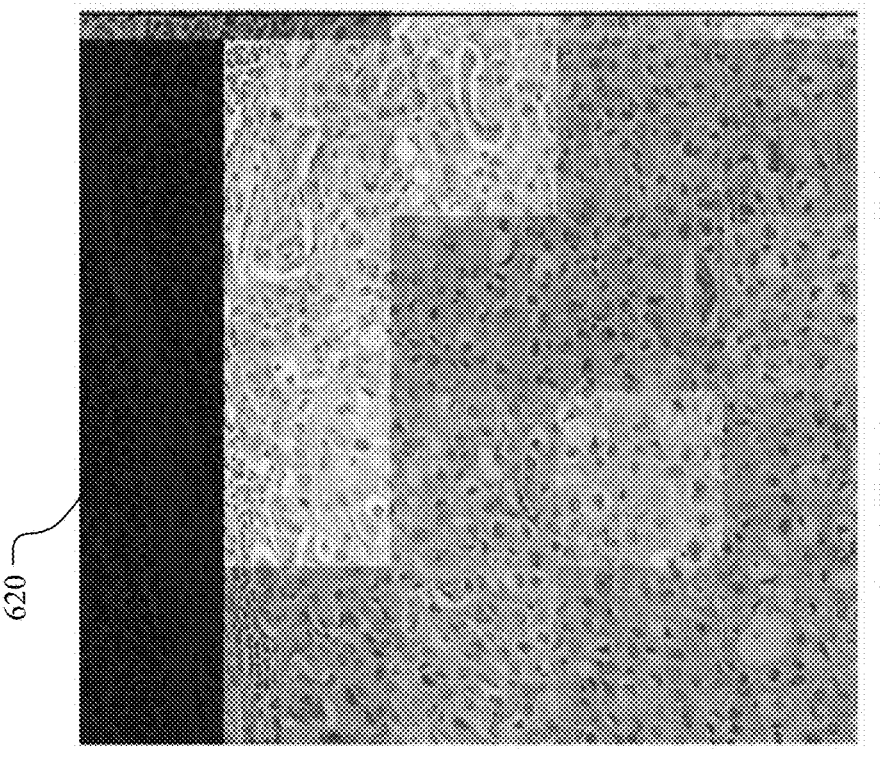
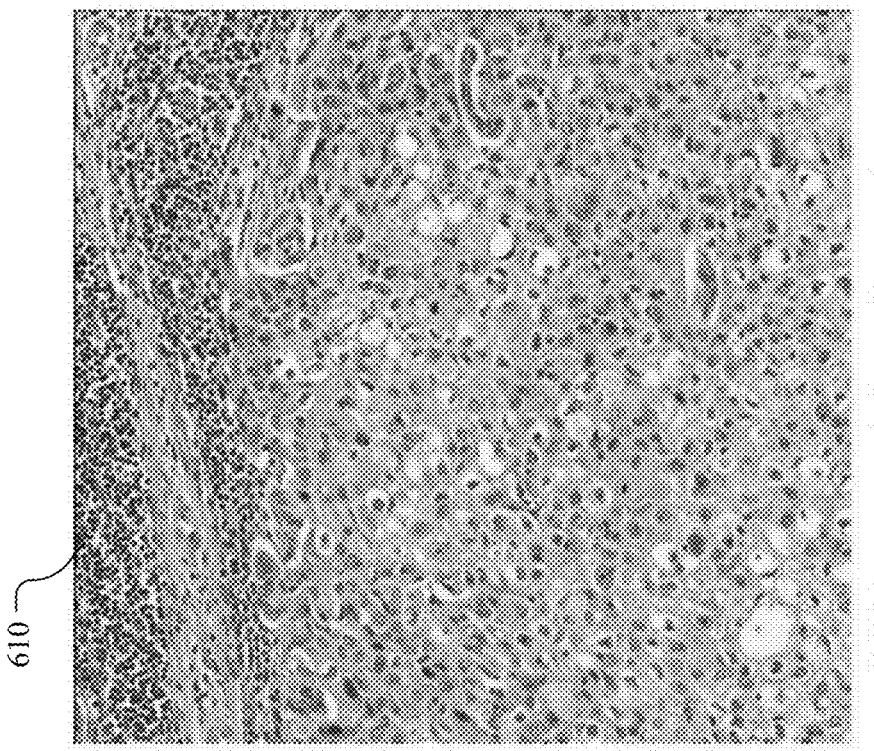
*FIG. 6*

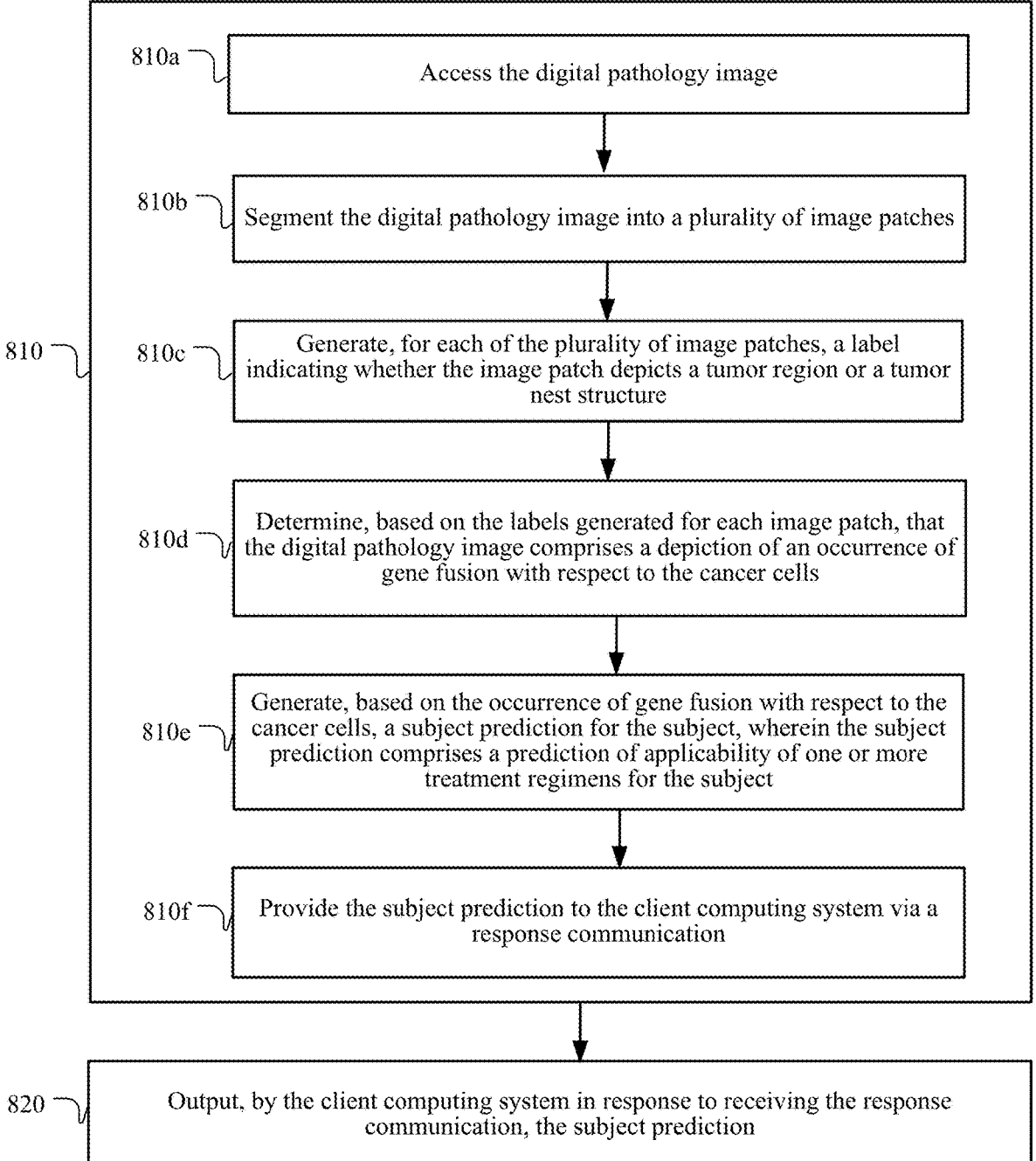

800

810a → Access the digital pathology image

810b → Segment the digital pathology image into a plurality of image patches

810 → 810c → Generate, for each of the plurality of image patches, a label indicating whether the image patch depicts a tumor region or a tumor nest structure 810d → Determine, based on the labels generated for each image patch, that the digital pathology image comprises a depiction of an occurrence of gene fusion with respect to the cancer cells 810e → Generate, based on the occurrence of gene fusion with respect to the cancer cells, a subject prediction for the subject, wherein the subject prediction comprises a prediction of applicability of one or more treatment regimens for the subject 810f → Provide the subject prediction to the client computing system via a response communication 820 → Output, by the client computing system in response to receiving the response communication, the subject prediction

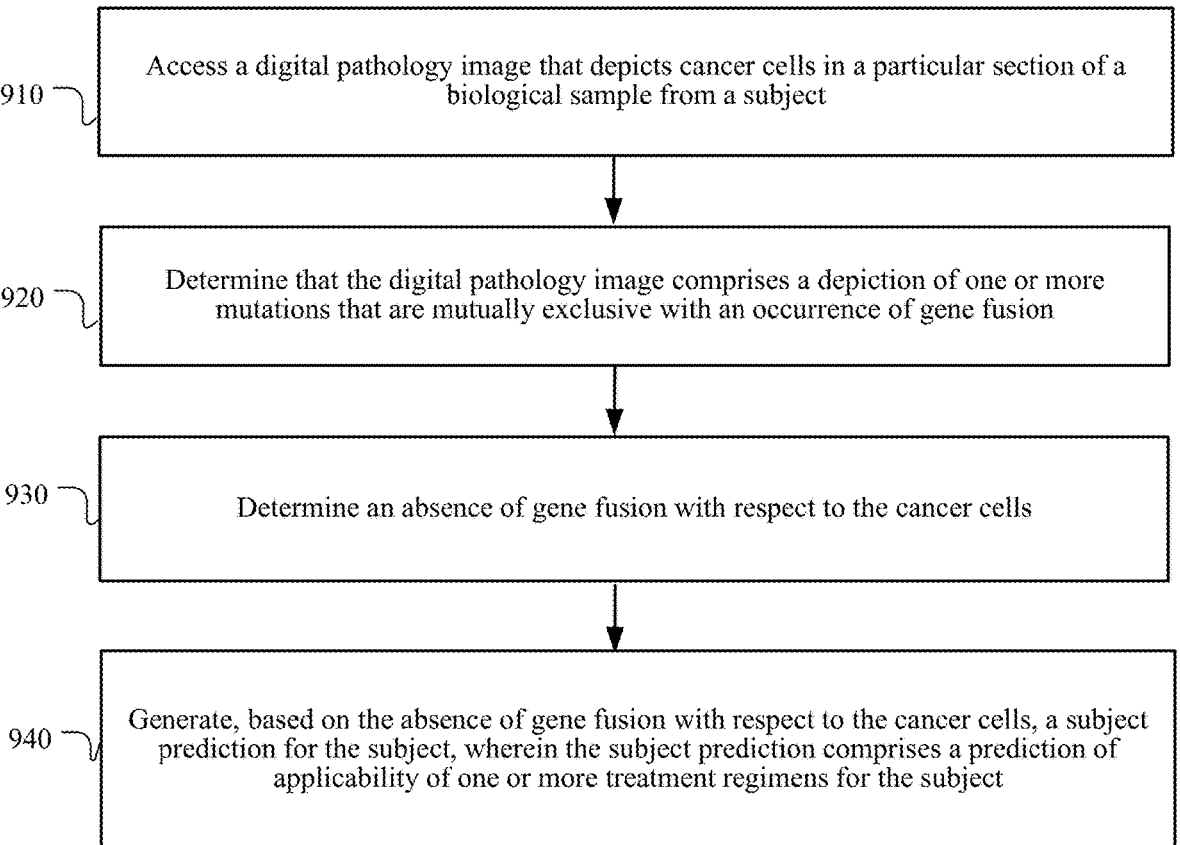

910    Access a digital pathology image that depicts cancer cells in a particular section of a biological sample from a subject 920    Determine that the digital pathology image comprises a depiction of one or more mutations that are mutually exclusive with an occurrence of gene fusion 930    Determine an absence of gene fusion with respect to the cancer cells 940    Generate, based on the absence of gene fusion with respect to the cancer cells, a subject prediction for the subject, wherein the subject prediction comprises a prediction of applicability of one or more treatment regimens for the subject

*FIG. 9*

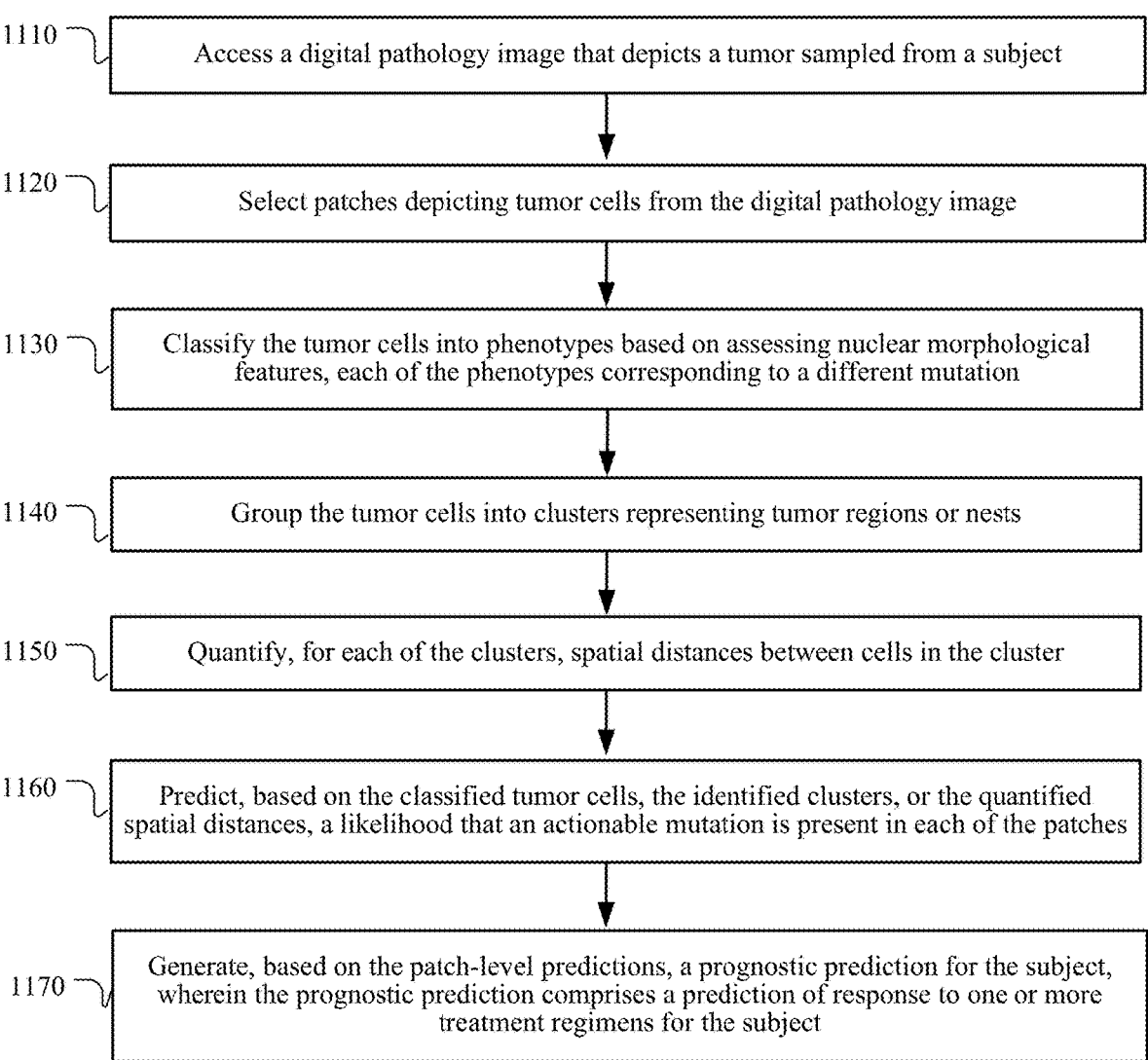

1100

1110  Access a digital pathology image that depicts a tumor sampled from a subject 1120  Select patches depicting tumor cells from the digital pathology image 1130  Classify the tumor cells into phenotypes based on assessing nuclear morphological features, each of the phenotypes corresponding to a different mutation 1140  Group the tumor cells into clusters representing tumor regions or nests 1150  Quantify, for each of the clusters, spatial distances between cells in the cluster 1160  Predict, based on the classified tumor cells, the identified clusters, or the quantified spatial distances, a likelihood that an actionable mutation is present in each of the patches 1170  Generate, based on the patch-level predictions, a prognostic prediction for the subject, wherein the prognostic prediction comprises a prediction of response to one or more treatment regimens for the subject

Unknown Driver (Area)

Unknown Driver (First Order Entropy)

Unknown Driver (RunLengthNonUniformity)

Driver Mutation (Area)

Driver Mutation (First Order Entropy)

Driver Mutation (RunLengthNonUniformity)

Gene Fusion (Area)

Gene Fusion (First Order Entropy)

Gene Fusion (RunLengthNonUniformity)

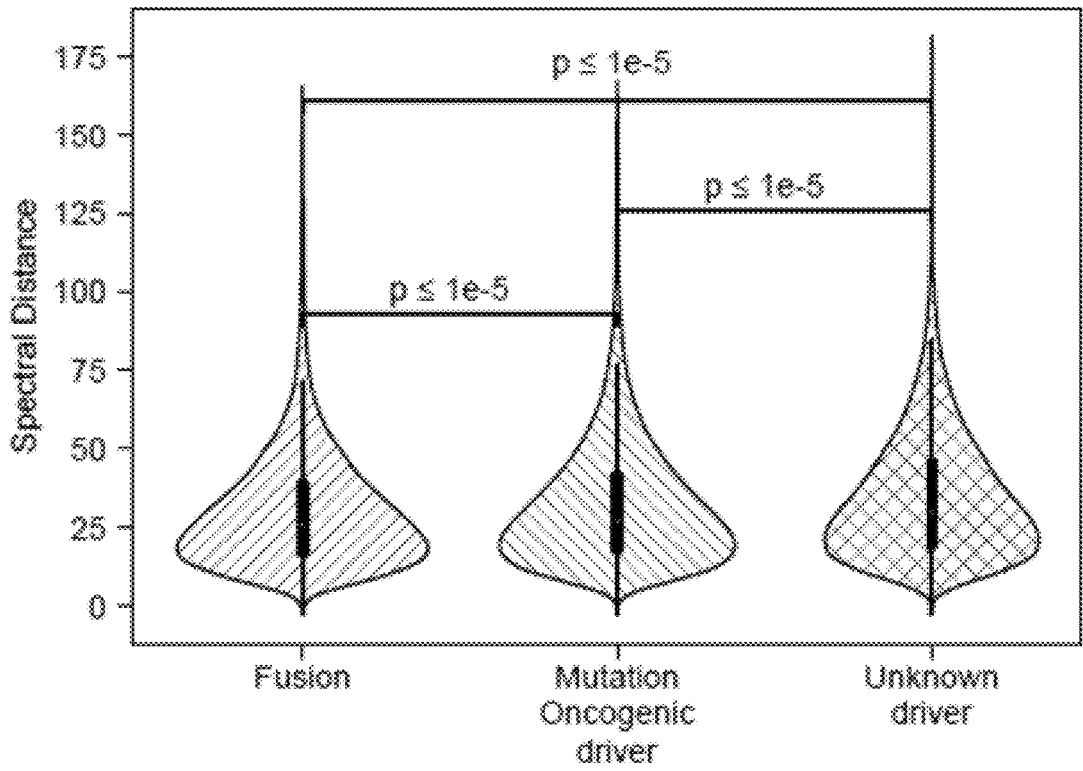
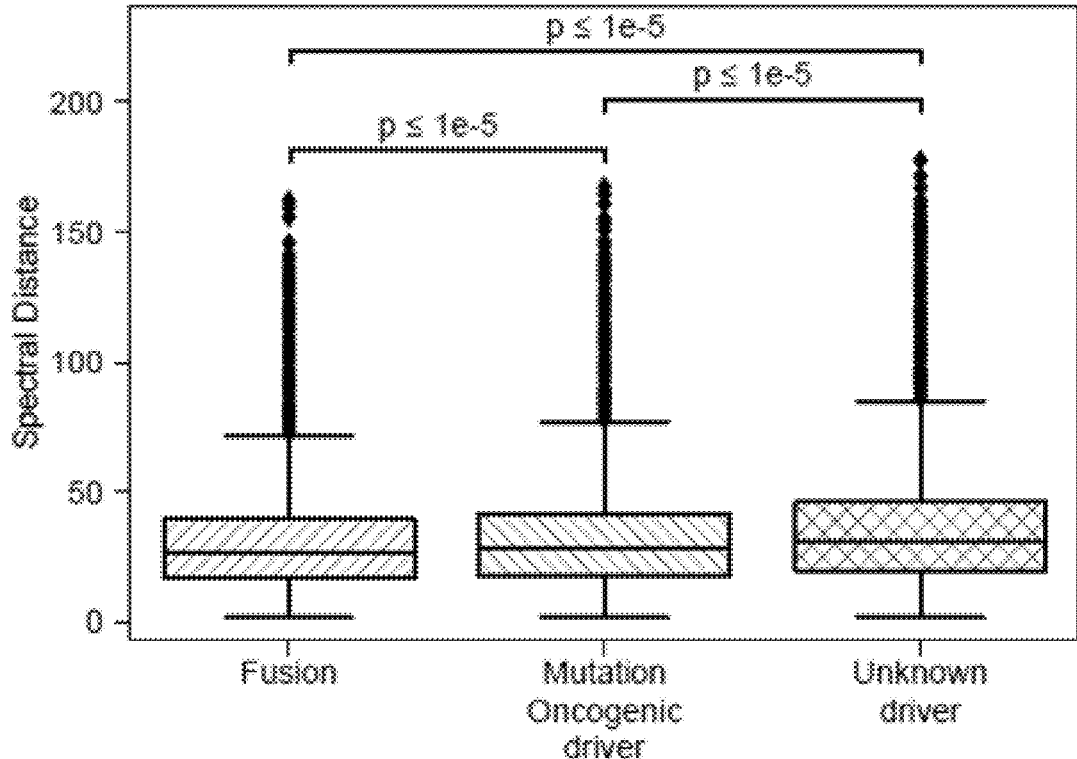
*FIG. 17B*

Co-occurring pairs with distance configuration:
p(◆,◆), p(●,●), p(■,■), p(◆,■), p(◆,●), p(●,■)

PREDICTING ACTIONABLE MUTATIONS FROM DIGITAL PATHOLOGY IMAGES

CROSS REFERENCE TO RELATED APPLICATIONS

This application is a continuation application of International Application No. PCT/US2022/029329, filed internationally on May 14, 2022, which claims the benefit of priority to U.S. Provisional Application No. 63/188,963, filed on May 14, 2021, U.S. Provisional Application No. 63/239,287, filed on Aug. 31, 2021, and U.S. Provisional Application No. 63/332,674, filed on Apr. 19, 2022.

TECHNICAL FIELD

The present disclosure relates to cancer diagnosis, treatment, and prognosis.

BACKGROUND

One important step in planning cancer treatment is identifying the treatment option that is most likely to be effective, taking into account both disease progression and likelihood of patient adherence. Once a malignant tumor has grown beyond a certain size and/or has metastasized, the patient's options may be limited to treatments such as chemotherapy, radiotherapy, targeted therapy, and immunotherapy. Patient adherence may be challenging with chemotherapy and radiotherapy, due to severe side effects that make patients feel ill. Patients also face a risk that cancer cells may mutate and become resistant to systemic therapy. Immunotherapies, the most novel of these treatment choices, activate the patient's own immune system and represent an important option in managing cancer albeit it may only be effective for 20%-30% of tumors. In general, across different tumor types, the following rationale is applied in order to maximize immediate clinical benefit as well as to safeguard future treatment options for the patient: As a first step, patients with high stage disease should first be screened for eligibility for targeted therapies. If no mutational targets are identified, then the patient is offered immunotherapies alone or in combination with traditional chemotherapy. As a last resort, should this combination fail, combinations of chemotherapy could be considered.

Targeted therapies may be preferable but only suitable for a small subset of tumors, due to the rarity of addressable mutations. Based on current approved therapies, addressable mutations occur exclusively on oncogenes, genes that positively regulate different cellular functions. In lung cancer, the most common and actionable mutations are found in the following oncogenes: EGFR, ALK, RET, ROS1, and NTRK. Aside from oncogenes, a second class of genes known as tumor suppressors can also lead to cancer when mutated. As their name suggests, these genes normally function to suppress cellular activity; a mutation in these genes would therefore lead to cancer via the loss of suppression. Finally, in clinical practice, the most comprehensive molecular characterization of tumors is performed using a next generation sequencing (NGS) panel. This assay only detects mutations in a subset of genes, with some panels querying as low as 25 genes while others can go up to 500 genes. This represents a minute proportion of the 20,000-25,000 total genes in the human genome. This could explain why a driver mutation is not found in a proportion of tumor samples tested via NGS (unknown driver).

Targeted therapies may include medicines that target epidermal growth factor receptor (EGFR), as well as the gene fusions involving anaplastic lymphoma kinase (ALK), RET, ROS1, and neurotrophic tyrosine receptor kinase (NTRK). For EGFR, although immunohistochemical stains can be used to identify the most common variants (e.g., with coverage of up to 97% of EGFR-positive lung adenocarcinoma patients), molecular testing may be required to identify resistance mutations in patients who have failed EGFR-targeted therapy. No such immunohistochemical stain has been developed for RET and ROS1, and the performance of the immunohistochemical stains for ALK and NTRK may be highly variable and difficult to interpret.

Gene fusions often require more sophisticated molecular assays with greater coverage of the genome than the more commonly used "hot spot" assays that test for a limited number of loci. To target gene fusions, one may need much wider coverage resulting in a much more expensive test, which requires much more technical capacity for a laboratory to perform. However, some gene fusions (e.g., NTRK fusion) may be exceedingly rare. Although NTRK fusions have been identified in a wide variety of tumor types, the frequency of this specific fusion may be less than 1% in the most common cancer indications (such as in lung adenocarcinoma, colorectal cancer, and non-secretory breast cancer). The relative rarity of gene fusions (e.g., ranging from 7% for ALK to less than 0.3% for NTRK in lung adenocarcinomas) constitute a significant technical and financial disincentive to widespread testing. Currently, molecular testing is the only method available so far to determine whether gene fusion exists in patients. However, molecular testing is expensive, so patients sometimes avoid scheduling molecular testing due to the high likelihood that the patient may not benefit from targeted therapy. As a result, a significant proportion of patients may be unlikely to receive the correct test to determine whether their tumors carry gene fusions. Therefore, a desire exists for a fast, robust, and sensitive screening tool to classify tumor samples by the type of test needed to determine their first and best systemic treatment option.

SUMMARY OF PARTICULAR EMBODIMENTS

Herein is provided a system and methods to identify actionable mutations, including, by way of example and not limitation, oncogene fusions (e.g., ALK, ROS1, RET and NTRK) using digital pathology techniques, wherein the actionable mutations are predictive of mutations for which a targeted therapy is available and prognostic of treatment response.

In some instances, the disclosed methods and systems may be applied to the detection of gene fusions/rearrangements, a specific type of rare, druggable oncogenic mutation event that can be identified across many different cancer types, that if present in a tumor tissue sample, may indicate a robust response to certain targeted therapies. Gene fusions include rare, druggable mutation events that can occur across many different tumor types and are increasingly targeted by novel therapies. The identification of gene fusions can be a technically difficult, expensive, and time-consuming process that in the end may only benefit a minority of patients that carry such genetic alterations; for these reasons, widespread testing may be limited to the few hospitals that can afford to absorb and provide the technical and financial resources involved in this process. The embodiments disclosed herein may address this disparity through the creation, training, and use of machine-learning models (e.g., digital pathology screening models) that can predict the presence of oncogenic fusions from digital pathology images such as scanned, stained (e.g., hematoxylin and eosin (H&E)-stained) whole slide images (WSI) depicting cancer tissue/cells (e.g., lung adenocarcinoma). In addition, the embodiments disclosed herein may include fast, cheap, and sufficiently-accurate screening tools that may be used to guide molecular testing and decision-making regarding the use of targeted therapies for individual in patients (including, but not limited to, lung adenocarcinoma patients).

In particular embodiments, a digital pathology image processing system may access a digital pathology image that depicts cancer cells in a particular section of a biological sample from a subject. The digital pathology image processing system may then identify one or more image patches from the digital pathology image, each depicting one or more clusters of tumor cells (e.g., a region completely comprised of tumor cells or region comprising one or more tumor nest structures surrounded by stroma). In some cases, when the digital pathology image has been divided into a plurality of tiles, the image patch may include a portion of an image tile, a plurality of adjacent tiles, or a combination of one or more adjacent tiles and one or more adjacent portions of tiles. The digital pathology image processing system may generate, for each of the plurality of image patches, a label indicating a likelihood (e.g., a binary output or a percentage output) that the image patch depicts a cluster of tumor cells. In particular embodiments, the digital pathology image processing system may determine, based on the labels generated for each patch, that the digital pathology image comprises a depiction of an occurrence of, e.g., a gene fusion, in the cancer cells present in the biological sample. The digital pathology image processing system may further generate, based on the detection of, e.g., a gene fusion, a prognostic prediction for the subject. In some embodiments, the prognostic prediction may comprise a prediction of applicability of one or more treatment regimens (e.g., chemotherapy or a targeted therapy) for the subject.

Disclosed herein are methods comprising: accessing a digital pathology image that depicts cancer cells in a particular section of a biological sample from a subject, and wherein the depicted particular section was stained with one or more stains; segmenting the digital pathology image into a plurality of image patches; generating, for each of the plurality of image patches, a label indicating a likelihood that the image patch depicts a cluster of tumor cells; determining, based on the labels generated for each image patch, that the digital pathology image comprises a depiction of an occurrence of gene fusion with respect to the cancer cells; and generating, based on the occurrence of gene fusion with respect to the cancer cells, a prognostic prediction for the subject, wherein the prognostic prediction comprises a prediction of applicability of one or more treatment regimens for the subject.

In some embodiments, the method further comprising detecting one or more features from each of the plurality of image patches, wherein the one or more features comprise one or more of a clinical feature or a histologic feature, and wherein generating the label for each of the plurality of image patches is based on the one or more features.

In some embodiments, generating the label for each of the plurality of image patches is based on tumor morphology, wherein the tumor morphology is based on an analysis of one or more of a presence of signet ring cells, a number of signet ring cells, a presence of hepatoid cells, a number of hepatoid cells, extracellular mucin, or a tumor growth pattern.

In some embodiments, generating the label for each of the plurality of image patches is based on one or more machine-learning models, wherein the method further comprises training the one or more machine-learning models based on a plurality of training data comprising one or more labeled depictions of a cluster of tumor cells and one or more labeled depictions of other histologic or clinical features.

In some embodiments, the prognostic prediction is generated further based on an analysis of one or more additional digital pathology images, each of the one or more additional digital pathology images depicting an additional particular sample of the biological sample from the subject, and wherein the analysis comprises: determining a likelihood that each of the one or more additional digital pathology images comprises a depiction of an occurrence of gene fusion with respect to the cancer cells; and combining the determination for each of the one or more additional digital pathology images.

In some embodiments, the method further comprising: outputting, via a graphical user interface, the prognostic prediction, wherein the graphical user interface comprises a graphical representation of the digital pathology image, and wherein the graphical representation comprises an indication of the label generated for each of the plurality of image patches and a predicted level of confidence associated with the respective label.

In some embodiments, the method further comprising: generating a recommendation associated with use of the one or more treatment regimens.

In some embodiments, the particular section of the biological sample was stained with one or more stains.

In some embodiments, determining that the digital pathology image comprises the depiction of the occurrence of gene fusion with respect to the cancer cells is further based on a weighted combination of the labels generated for each image patch.

In some embodiments, the method further comprising: identifying tumor heterogeneity from the digital pathology image; and measuring the identified tumor heterogeneity, wherein determining that the digital pathology image comprises the depiction of the occurrence of gene fusion is further based on the measured tumor heterogeneity.

In some embodiments, identifying tumor heterogeneity comprises classifying mutated tumor cells into phenotypes by identifying morphologically similar cells, e.g., by assessing nuclear heterogeneity. In some embodiments, assessing nuclear heterogeneity comprises quantifying certain features of cell nuclei to distinguish mutated cells based on nuclear morphologic heterogeneity.

In some embodiments, identifying tumor heterogeneity comprises identifying regions of clonal cells by conducting a cell-level spatial analysis to assess spatial distribution. In some embodiments, assessing spatial distribution comprises measuring spectral distances within subgraphs of a minimum spanning tree of tumor cells, wherein each of the subgraphs represents a cluster of adjacent cells (e.g., a tumor nest), and computing adjacency spectral distances pairwise across all of the subgraphs. In some embodiments, each of the subgraphs may be defined by performing outlier detection. In some embodiments, each of the subgraphs may be defined based on segmentation of detected tumor nests.

In some embodiments, identifying tumor heterogeneity comprises identifying regions of closely adjacent clonal cells by conducting a cell-level spatial analysis to assess spatial entropy. In some embodiments, assessing spatial entropy comprises computing, for each of a predefined number of distance bins, a frequency of pairs of cells identified as being morphologically similar.

Disclosed herein are one or more computer-readable non-transitory storage media embodying software that is operable when executed to perform part or all of one or more methods disclosed herein.

Disclosed herein are systems comprising: one or more processors; and a non-transitory memory including instructions that, when executed by the one or more data processors, cause the one or more data processors to perform part or all of one or more methods disclosed herein.

Disclosed herein are methods comprising: transmitting, from a client computing system to a remote computing system, a request communication to process a digital pathology image that depicts cancer cells in a particular section of a biological sample from a subject, wherein in response to receiving the request communication from the client computing system, the remote computing system performs operations comprising: accessing the digital pathology image; segmenting the digital pathology image into a plurality of image patches; generating, for each of the plurality of image patches, a label indicating a likelihood (e.g., a binary output or a percentage output) that the image patch depicts a cluster of tumor cells; determining, based on the labels generated for each image patch, that the digital pathology image comprises a depiction of an occurrence of gene fusion with respect to the cancer cells; generating, based on the occurrence of gene fusion with respect to the cancer cells, a prognostic prediction for the subject, wherein the prognostic prediction comprises a prediction of applicability of one or more treatment regimens for the subject; and providing the prognostic prediction to the client computing system via a response communication; and outputting, by the client computing system in response to receiving the response communication, the prognostic prediction.

Disclosed herein are methods comprising, by a digital pathology image processing system: accessing a digital pathology image that depicts cancer cells in a particular section of a biological sample from a subject; determining that the digital pathology image comprises a depiction of one or more mutations that are mutually exclusive with an occurrence of gene fusion; determining an absence of gene fusion with respect to the cancer cells; and generate, based on the absence of gene fusion with respect to the cancer cells, a prognostic prediction for the subject, wherein the prognostic prediction comprises a prediction of applicability of one or more treatment regimens for the subject.

BRIEF DESCRIPTION OF THE DRAWINGS

FIG. 3 is a flowchart for a non-limiting example method for predicting gene fusion.

FIG. 5A illustrates a non-limiting example of pathology slide images for lung adenocarcinoma.

FIG. 5B illustrates a non-limiting example of results from quality control.

FIG. 5C illustrates a non-limiting example of tumor cluster detection.

FIG. 5D illustrates a non-limiting example of prediction of gene fusion status.

FIG. 6 illustrates a non-limiting example prediction of ROS1 gene fusion status.

FIG. 8 is a flowchart for a non-limiting example method for enabling end users to request prognostic predictions.

FIG. 9 is a flowchart for a non-limiting example method for predicting an alternate treatment based on identifying a lack (or an absence) of gene fusion.

FIG. 11 is a flowchart for a non-limiting example method for identifying tumor heterogeneity.

Figure 13B:
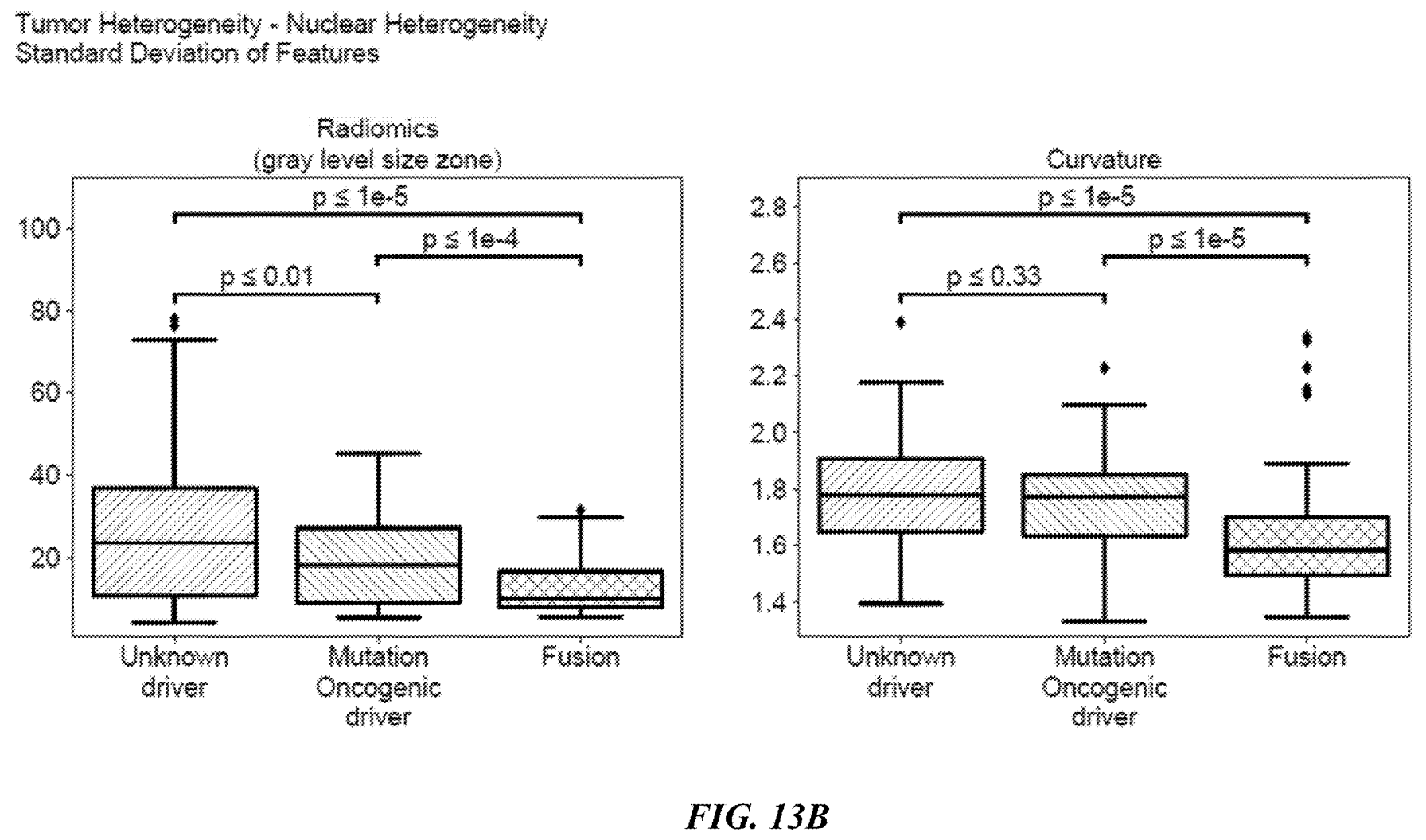

FIGS. 13A-13E illustrate non-limiting examples of experimental results of identification of gene fusions based on quantifying certain nuclear morphology features.

FIG. 17B illustrates a non-limiting example of experimental results of identification of gene fusions based on quantifying adjacency spectral distances as between the subgraphs.

DESCRIPTION

In order to identify which patients may benefit from molecular testing for gene fusions, pathologists may review slide images of tumor tissue samples to assess indicators of tumor heterogeneity. Tumor heterogeneity may be observed from distinct morphological and phenotypic profiles of different tumor cells that correspond to gene mutations that cause cells to become cancerous and grow and spread in the body. Tumor heterogeneity may manifest as either intra-tumor heterogeneity, for example, within a single tumor nest, or as inter-tumor heterogeneity, for example, as between nearby tumor nests. Beyond serving as a differentiator between normal tissue and tumor tissue, tumor heterogeneity may serve as an indicator of disease severity-a highly heterogeneous tumor (a.k.a. a bizarre tumor) may indicate a poor prognosis, due to therapeutic failure attributable to drug resistance acquired through gene mutations.

Figure 1A:
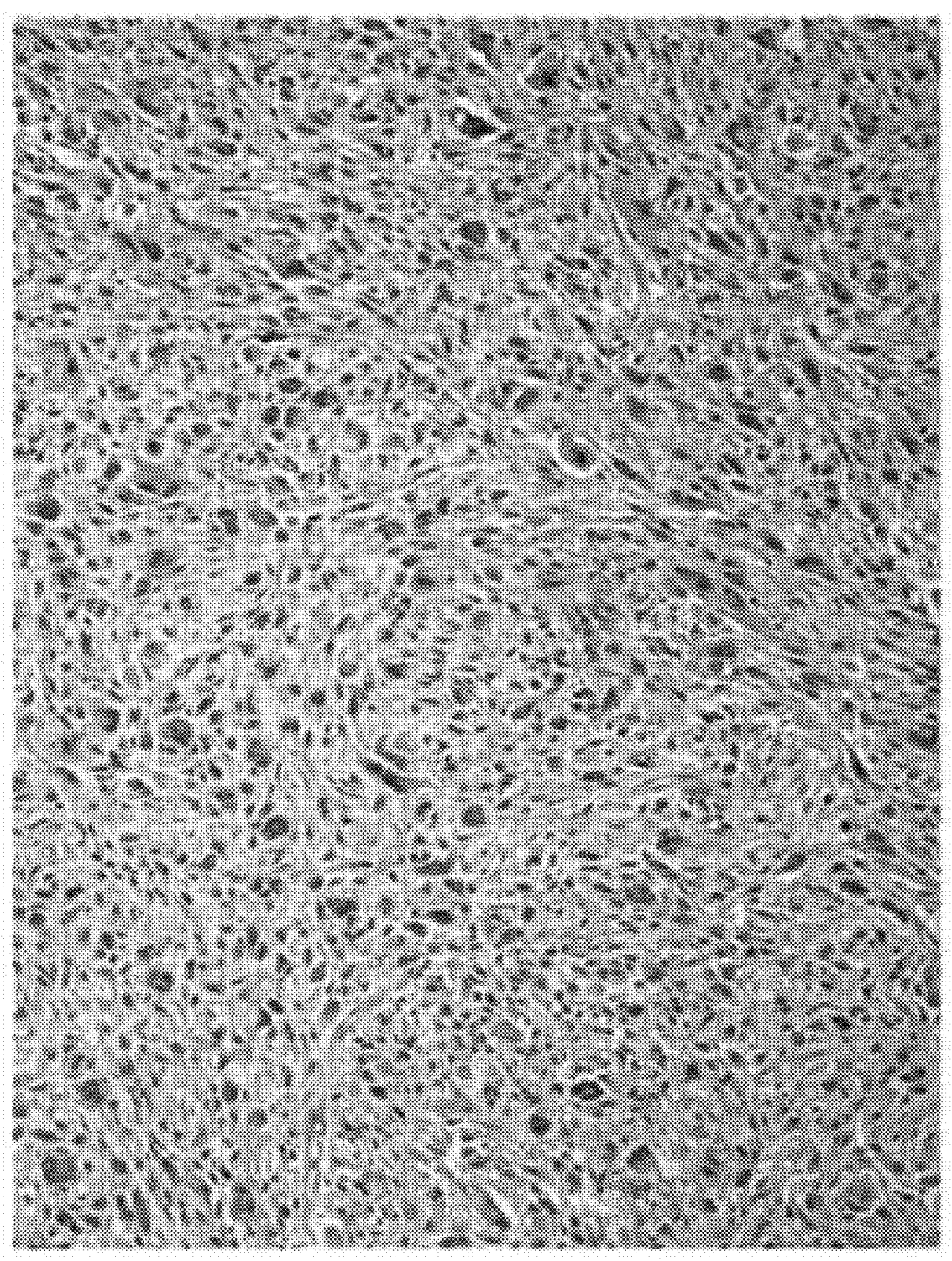
FIGS. 1A-1D illustrate non-limiting example of tumor heterogeneity.
Figure 1B:
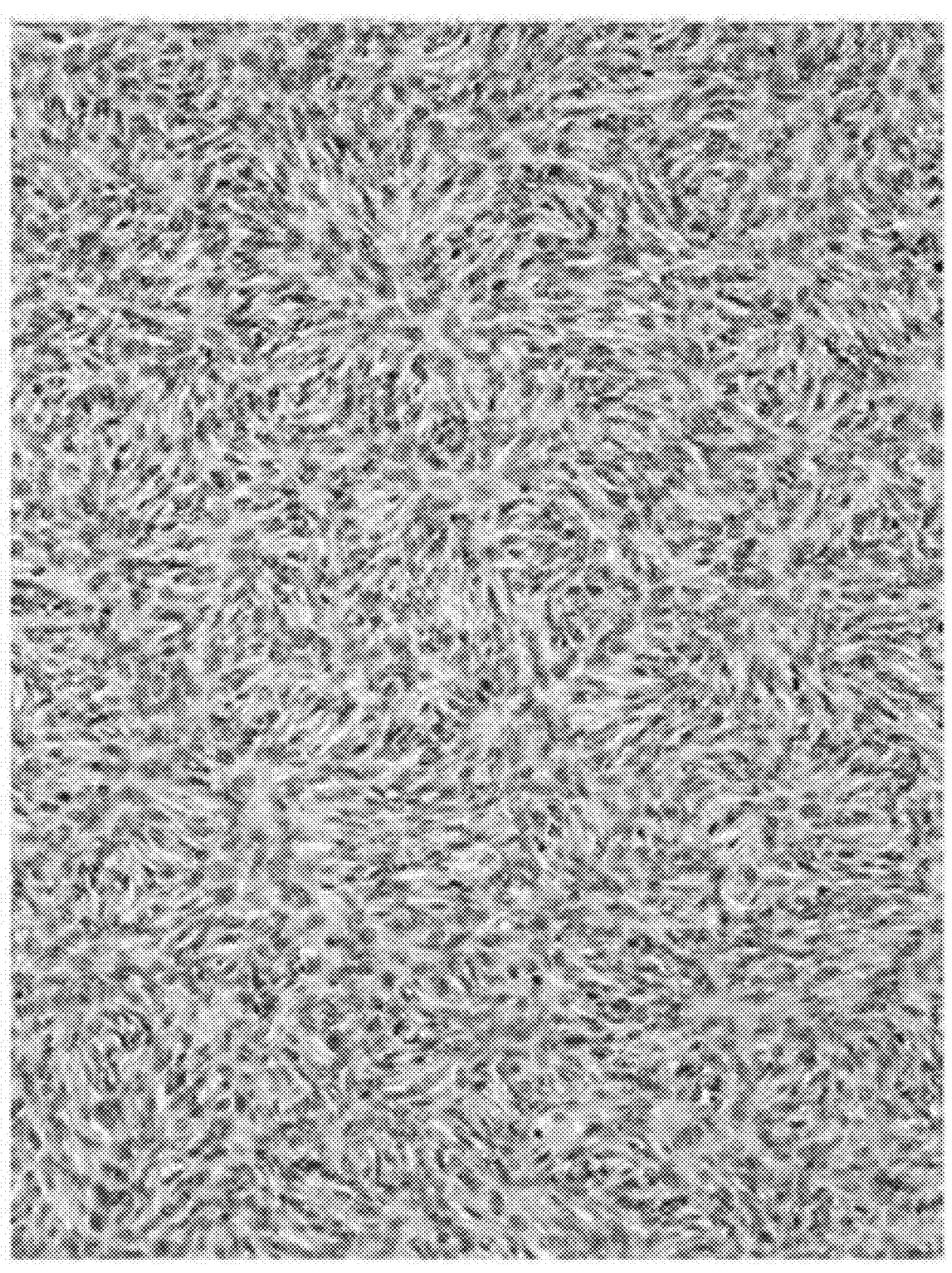
Figure 1C:
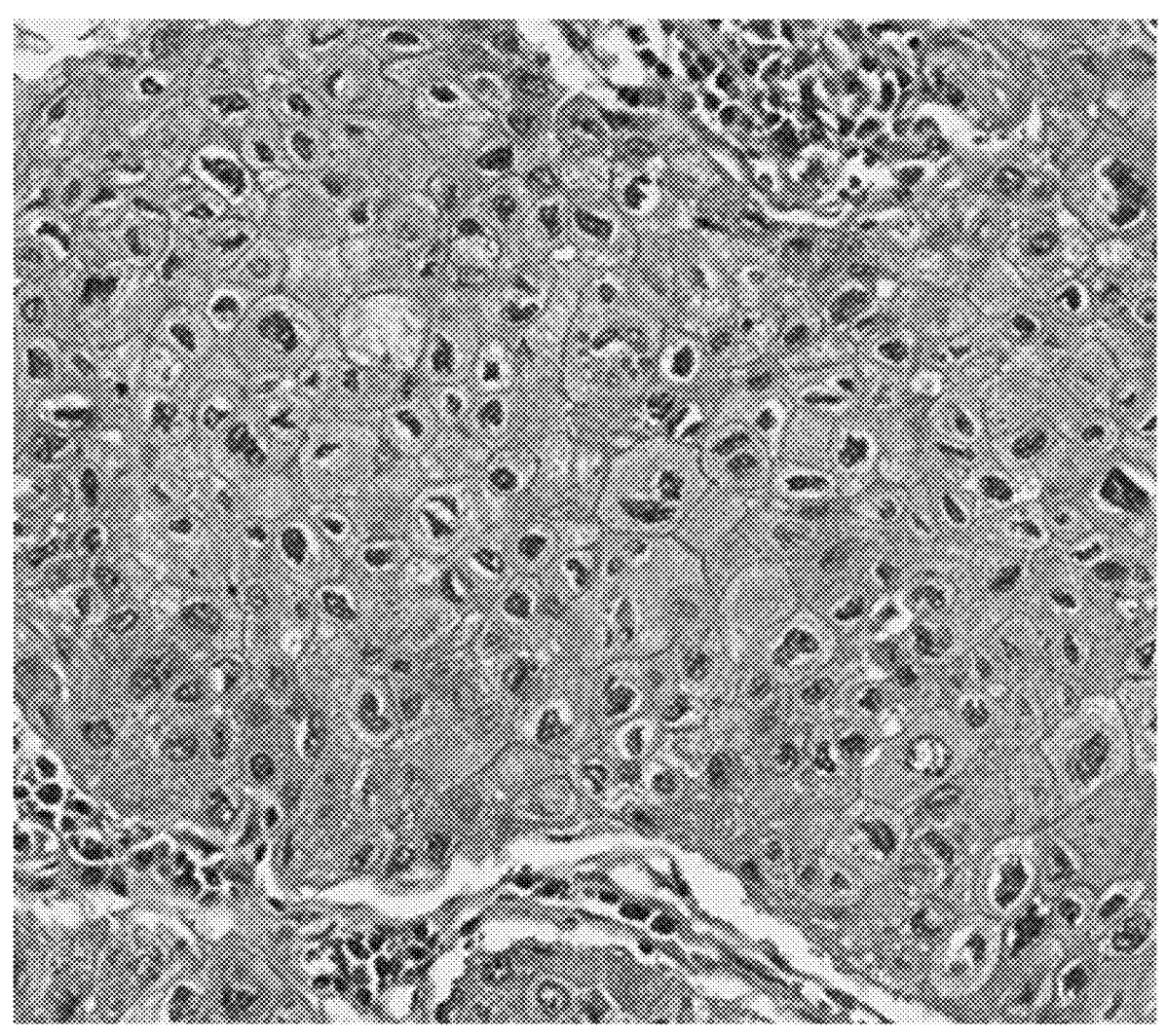
Figure 1D:
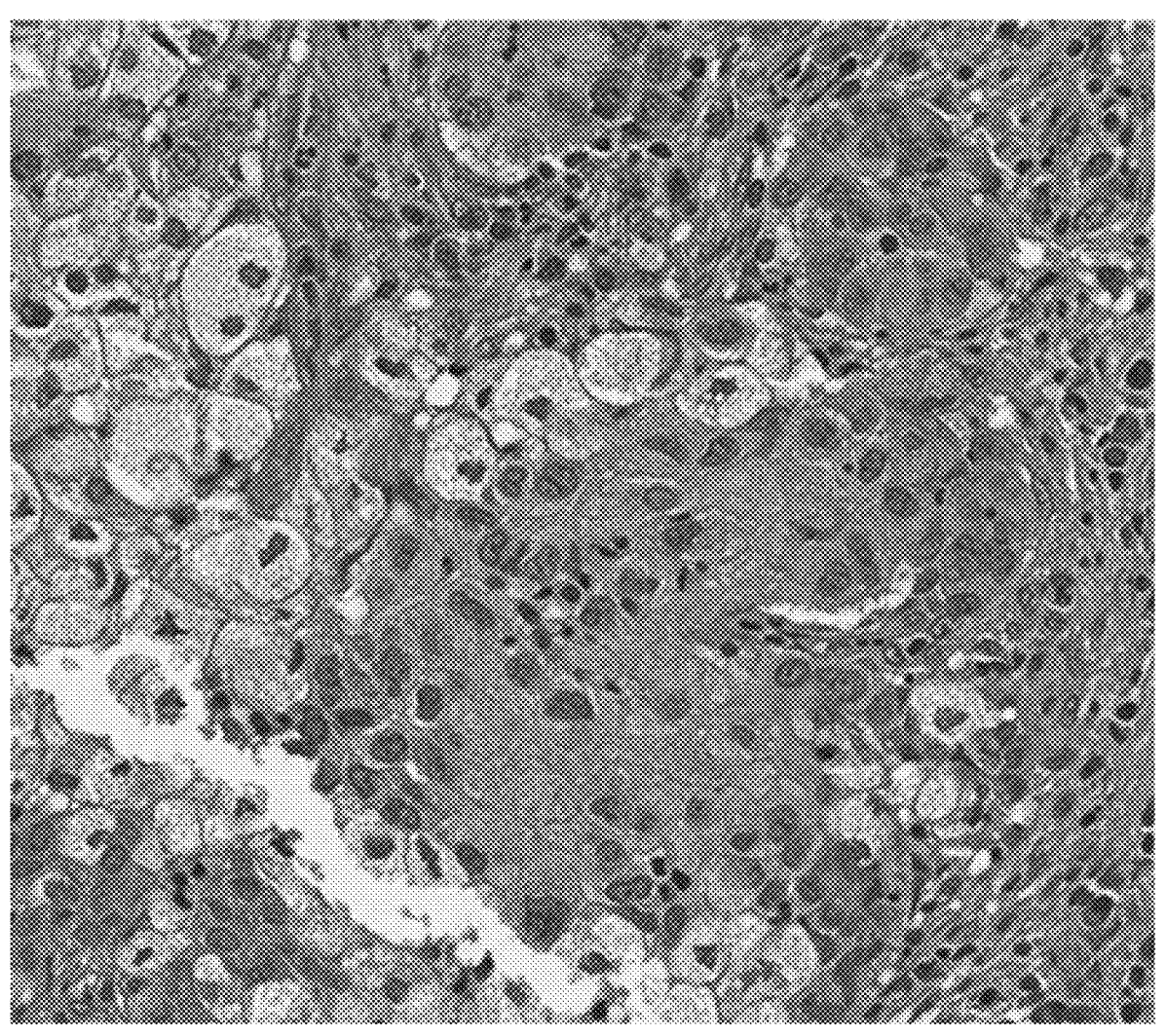

FIGS. 1A-1D illustrate examples of tumor heterogeneity as visualized in digital pathology images. FIG. 1A illustrates an example of tumor heterogeneity in uterine leiomyosarcoma. The tumor cells look very different from each other. For example, in terms of size there are some tumor cells that are double, triple, or quadruple in size to others. In terms of curvature, some tumor cells have a smooth and rounded contour while others are angular (i.e., have at least two re. In other words, they are very heterogeneous. FIG. 1B illustrates an example of tumor heterogeneity in dermatofibrosarcoma protuberans. In contrast to FIG. 1A, the tumor cells in FIG. 1B as a population are more similar in terms of their shape, chromatic intensity, angularity, and size. In sarcomas (such as those depicted in FIGS. 1A and 1B), high heterogeneity (e.g., as shown in FIG. 1A) is often associated with aneuploidy which is aberrations of chromosome number, whereas monotony (e.g. as shown in FIG. 1B), a.k.a. low tumor heterogeneity, may be associated with gene fusions. FIG. 1C illustrates an example of high tumor heterogeneity in a lung squamous cell carcinoma sample. FIG. 1D illustrates an example of high tumor heterogeneity in a lung adenocarcinoma sample.

Patients with gene fusions often present at an advanced stage of the disease. Gene fusions/rearrangements are a rare type of oncogenic mutation event that can be identified across many different cancer types. These mutations, however, carry an increasingly outsized importance as the presence of certain gene fusions from a tumor sample can indicate a likelihood of a robust response to certain targeted therapies. In such gene fusions, on a cellular level, the cells may appear to have low heterogeneity (i.e., appear to be clonal), and yet on the group level (e.g., the population level) their phenotype (i.e., the set of morphological features, wherein tumor cells sharing a common set of morphological features are said to belong to a single phenotype) may be aggressive, as corresponds to a diagnosis at an advanced stage. There are at least a couple of hypotheses regarding the correlation of tumor heterogeneity with gene fusion. One hypothesis may be that the visual signal that is indicative for gene fusions may reside primarily in tumor nests/cells. Another hypothesis may be that the visual signal that is indicative of gene fusion may be strong and diffuse across all parts of the tumor area. Yet another hypothesis may be that low tumor mutational burden may suggest decreased tumor morphologic heterogeneity. In any case, lack of tumor heterogeneity in aggressive malignant tumors may thus be the signature for gene fusions across tumor types. However, in some instances, it may be difficult for human eyes to observe the lack of tumor heterogeneity.

Figure 2:
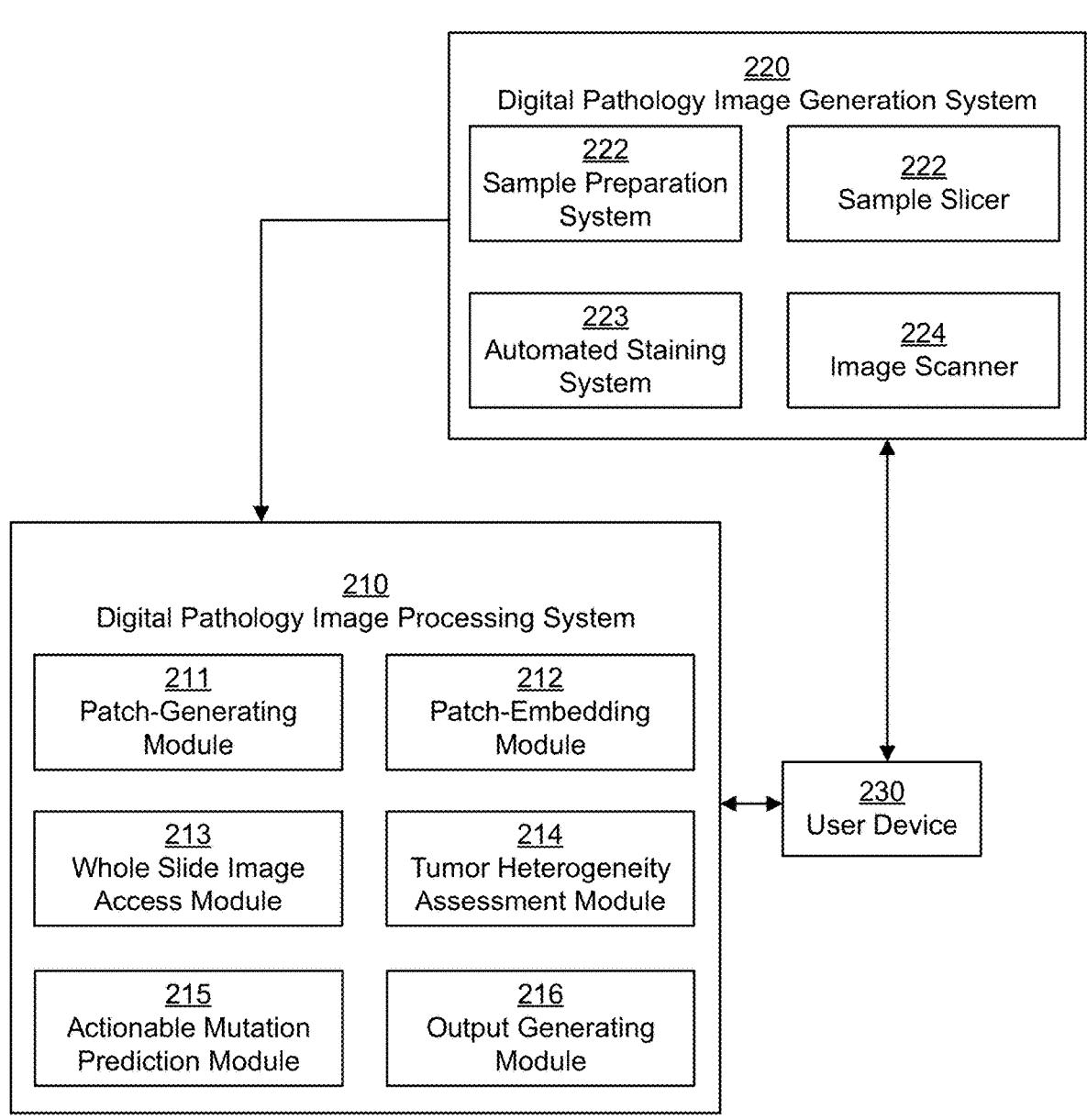
FIG. 2 illustrates a non-limiting example of a network of interacting computer systems that can be used for digital pathology image generation and processing, as described herein according to some embodiments of the present disclosure.

FIG. 2 illustrates a network 200 of interacting computer systems that can be used for digital pathology image generation and processing, including prediction of actionable mutations, as described herein according to some embodiments of the present disclosure.

A digital pathology image generation system 220 can generate one or more whole slide images (WSIs) or other related digital pathology images, corresponding to a particular sample. For example, an image generated by digital pathology image generation system 220 can include a stained section of a biopsy sample. As another example, an image generated by digital pathology image generation system 220 can include a slide image (e.g., a blood film) of a liquid sample. As another example, an image generated by digital pathology image generation system 220 can include fluorescence microscopy such as a slide image depicting fluorescence in situ hybridization (FISH) after a fluorescent probe has been bound to a target DNA or RNA sequence.

Some types of samples (e.g., biopsies, solid samples and/or samples including tissue) can be processed by a sample preparation system 221 to fix and/or embed the sample. Sample preparation system 221 can facilitate infiltrating the sample with a fixating agent (e.g., liquid fixing agent, such as a formaldehyde solution) and/or embedding substance (e.g., a histological wax). For example, a sample fixation sub-system can fix a sample by exposing the sample to a fixating agent for at least a threshold amount of time (e.g., at least 3 hours, at least 6 hours, or at least 13 hours). A dehydration sub-system can dehydrate the sample (e.g., by exposing the fixed sample and/or a portion of the fixed sample to one or more ethanol solutions) and potentially clear the dehydrated sample using a clearing intermediate agent (e.g., that includes ethanol and a histological wax). A sample embedding sub-system can infiltrate the sample (e.g., one or more times for corresponding predefined time periods) with a heated (e.g., and thus liquid) histological wax. The histological wax can include a paraffin wax and potentially one or more resins (e.g., styrene or polyethylene). The sample and wax can then be cooled, and the wax-infiltrated sample can then be blocked out.

A sample slicer 222 can receive the fixed and embedded sample and can produce a set of sections. Sample slicer 222 can expose the fixed and embedded sample to cool or cold temperatures. Sample slicer 222 can then cut the chilled sample (or a trimmed version thereof) to produce a set of sections. Each section can have a thickness that is (for example) less than 100 μm, less than 50 μm, less than 10 μm or less than 5 μm. Each section can have a thickness that is (for example) greater than 0.1 μm, greater than 1 μm, greater than 2 μm or greater than 4 μm. The cutting of the chilled sample can be performed in a warm water bath (e.g., at a temperature of at least 30° C., at least 35° C. or at least 40° C.).

An automated staining system 223 can facilitate staining one or more of the sample sections by exposing each section to one or more staining agents. Each section can be exposed to a predefined volume of staining agent for a predefined period of time. In some instances, a single section is concurrently or sequentially exposed to multiple staining agents.

Each of one or more stained sections can be presented to an image scanner 224, which can capture a digital image of the section. Image scanner 224 can include a microscope camera. The image scanner 224 can capture the digital image at multiple levels of magnification (e.g., using a 10× objective, 20× objective, 40× objective, etc.). Manipulation of the image can be used to capture a selected portion of the sample at the desired range of magnifications. Image scanner 224 can further capture annotations and/or morphometrics identified by a human operator. In some instances, a section is returned to automated staining system 223 after one or more images are captured, such that the section can be washed, exposed to one or more other stains, and imaged again. When multiple stains are used, the stains can be selected to have different color profiles, such that a first region of an image corresponding to a first section portion that absorbed a large amount of a first stain can be distinguished from a second region of the image (or a different image) corresponding to a second section portion that absorbed a large amount of a second stain.

It will be appreciated that one or more components of digital pathology image generation system 220 can, in some instances, operate in connection with human operators. For example, human operators can move the sample across various sub-systems (e.g., of sample preparation system 221 or of digital pathology image generation system 220) and/or initiate or terminate operation of one or more sub-systems, systems, or components of digital pathology image generation system 220. As another example, part or all of one or more components of digital pathology image generation system (e.g., one or more subsystems of the sample preparation system 221) can be partly or entirely replaced with actions of a human operator.

Further, it will be appreciated that, while various described and depicted functions and components of digital pathology image generation system 220 pertain to processing of a solid and/or biopsy sample, other embodiments can relate to a liquid sample (e.g., a blood sample). For example, digital pathology image generation system 220 can receive a liquid-sample (e.g., blood or urine) slide that includes a base slide, smeared liquid sample and cover. Image scanner 224 can then capture an image of the sample slide. Further embodiments of the digital pathology image generation system 220 can relate to capturing images of samples using advancing imaging techniques, such as FISH, described herein. For example, once a florescent probe has been introduced to a sample and allowed to bind to a target sequence appropriate imaging can be used to capture images of the sample for further analysis.

A given sample can be associated with one or more users (e.g., one or more physicians, laboratory technicians and/or medical providers) during processing and imaging. An associated user can include, by way of example and not of limitation, a person who ordered a test or biopsy that produced a sample being imaged, a person with permission to receive results of a test or biopsy, or a person who conducted analysis of the test or biopsy sample, among others. For example, a user can correspond to a physician, a pathologist, a clinician, or a subject. A user can use one or one user devices 230 to submit one or more requests (e.g., that identify a subject) that a sample be processed by digital pathology image generation system 220 and that a resulting image be processed by a digital pathology image processing system 210.

Digital pathology image generation system 220 can transmit an image produced by image scanner 224 back to user device 230. User device 230 then communicates with the digital pathology image processing system 210 to initiate automated processing of the image. In some instances, digital pathology image generation system 220 provides an image produced by image scanner 224 to the digital pathology image processing system 210 directly, e.g., at the direction of the user of a user device 230. Although not illustrated, other intermediary devices (e.g., data stores of a server connected to the digital pathology image generation system 220 or digital pathology image processing system 210) can also be used. Additionally, for the sake of simplicity only one digital pathology image processing system 210, image generating system 220, and user device 230 is illustrated in the network 200. This disclosure anticipates the use of one or more of each type of system and component thereof without necessarily deviating from the teachings of this disclosure.

The network 200 and associated systems shown in FIG. 2 can be used in a variety of contexts where scanning and evaluation of digital pathology images, such as WSIs, are an essential component of the work. As an example, the network 200 can be associated with a clinical environment, where a user is evaluating the sample for possible diagnostic purposes. The user can review the image using the user device 230 prior to providing the image to the digital pathology image processing system 210. The user can provide additional information to the digital pathology image processing system 210 that can be used to guide or direct the analysis of the image by the digital pathology image processing system 210. For example, the user can provide a prospective diagnosis or preliminary assessment of features within the scan. The user can also provide additional context, such as the type of tissue being reviewed. As another example, the network 200 can be associated with a laboratory environment were tissues are being examined, for example, to determine the efficacy or potential side effects of a drug. In this context, it can be commonplace for multiple types of tissues to be submitted for review to determine the effects on the whole body of said drug. This can present a particular challenge to human scan reviewers, who may need to determine the various contexts of the images, which can be highly dependent on the type of tissue being imaged. These contexts can optionally be provided to the digital pathology image processing system 210.

Digital pathology image processing system 210 can process digital pathology images, including WSIs, to classify the digital pathology images and generate annotations for the digital pathology images and related output. As an example, the digital pathology image processing system 210 can process WSIs of tissue samples, or image patches of the WSIs generated by the digital pathology image processing system 210, to identify morphological traits that may be observed in clusters of tumor cells, and determine occurrences of gene alteration events, such as gene fusions based on the identified morphological traits. The digital pathology image processing system 210 may use sliding windows to generate a mask over the cluster of tumor cells. In addition to its use for identifying clusters of tumor cells in the WSI, the mask may be also used for measuring thickness, determining lengths for different endpoints, determining curviness for tortuosity, and measuring volume in a three-dimensional imaging or processing scenario. The digital pathology image processing system 210 may then crop the querying image into a plurality of image patches. A patch-generating module 211 can define a set of image patches for each digital pathology image. To define the set of image patches, the patch-generating module 211 can segment the digital pathology image into the set of image patches. As embodied herein, the image patches can be non-overlapping (e.g., each image patch includes pixels of the image not included in any other image patch) or overlapping (e.g., each image patch includes some portion of pixels of the image that are included in at least one other image patch). Features such as whether or not image patches overlap, in addition to the size of each image patch and the stride of the window (e.g., the image distance or number of pixels between an image patch and a subsequent image patch) can increase or decrease the data set for analysis, with more image patches (e.g., achieved through the use of overlapping or smaller image patches) increasing the potential resolution of eventual output and visualizations. In some instances, patch-generating module 211 defines a set of image patches for an image where each image patch is of a predefined size and/or an offset between image patches is predefined. Continuing with the example of detecting gene fusions or other gene alterations, each pathology slide image may be cropped into image patches with width and height of certain number of pixels. Furthermore, in some instances, the patch-generating module 211 can create multiple sets of image patches of varying size, overlap, step size, etc., for each WSI. As an example, in some instances, the width and height of each image patch (in terms of a number of pixels) may be dynamically determined (i.e., not fixed) based on factors such as the evaluation task at hand, the query image itself, or any suitable factor. In some embodiments, the digital pathology image itself can contain image patch overlap, which may result from the imaging technique. In some instances, even segmentation performed without image patch overlapping may be a preferable to balance image patch processing requirements and avoid influencing the embedding generation and weighting value generation discussed herein. An image patch size or image patch offset can be determined, for example, by calculating one or more performance metrics (e.g., precision, recall, accuracy, and/or error) for each size/offset and by selecting an image patch size and/or offset associated with one or more performance metrics above a predetermined threshold and/or associated with one or more performance metric(s) (e.g., high precision, high recall, high accuracy, and/or low error).

The patch-generating module 211 may further define an image patch size depending on the type of abnormality being detected. For example, the patch-generating module 211 can be configured with awareness of the type(s) of tissue phenotypic traits or abnormalities that the digital pathology image processing system 210 will be searching for, and can customize the image patch size according to the tissue phenotypes or abnormalities (and according to tissue sample type, in some instances) to improve detection. For example, the image generating module 211 can determine that, when the tissue phenotypes or abnormalities include searching for inflammation or necrosis in lung tissue, the image patch size should be reduced to increase the scanning rate, while when the tissue abnormalities include abnormalities with Kupffer cells in liver tissues, the image patch size should be increased to increase the opportunities for the digital pathology image processing system 210 to analyze the Kupffer cells holistically. In some instances, patch-generating module 211 defines a set of image patches where a number of image patches in the set, a size of the image patches of the set, the resolution of the image patches for the set, or other related properties, for each WSI is defined and held constant for each of one or more images.

As embodied herein, the patch-generating module 211 can further define the set of image patches for each digital pathology image along one or more color channels or color combinations. As an example, digital pathology images received by digital pathology image processing system 210 can include large-format multi-color channel images having pixel color values (e.g., bit values corresponding to intensities) specified for each pixel of the image for one of several color channels. Example color specifications or color spaces that can be used include the RGB, CMYK, HSL, HSV, or HSB color specifications. The set of image patches can be defined based on segmenting the color channels and/or generating a brightness map or greyscale equivalent of each image patch. For example, for each segment of an image, the patch-generating module 211 can provide a red image patch, blue image patch, green image patch, and/or brightness image patch, or the equivalent for the color specification used. As explained herein, segmenting the digital pathology images based on segments of the image and/or color values of the segments can improve the accuracy and recognition rates of the models/networks used to generating embeddings (e.g., lower-dimensional space) for the image patches and digital pathology image and to produce classifications of the digital pathology image. Additionally, the digital pathology image processing system 210, e.g., using patch-generating module 211, can convert between color specifications and/or prepare copies of the image patches using multiple color specifications. Color specification conversions can be selected based on a desired type of image augmentation (e.g., accentuating or boosting particular color channels, saturation levels, brightness levels, etc.). Color specification conversions can also be selected to improve compatibility between digital pathology image generation systems 220 and the digital pathology image processing system 210. For example, a particular image scanning component can provide output in the HSL color specification and the models used in the digital pathology image processing system 210, as described herein, can be trained using RGB images. Converting the image patches to the compatible color specification can ensure the image patches can still be analyzed. Additionally, the digital pathology image processing system can up-sample or down-sample images that are provided in particular color depth (e.g., 8-bit, 1-bit, etc.) to be usable by the digital pathology image processing system. Furthermore, the digital pathology image processing system 210 can cause image patches to be converted according to the type of image that has been captured (e.g., fluorescent images may include greater detail on color intensity or a wider range of colors).

In some instances, the digital pathology image processing system 210 may detect one or more features from each of the plurality of image patches. The one or more features may comprise, for example, one or more of a clinical feature or a histologic feature, such as a cell type. Accordingly, generating the label for each of the plurality of image patches may be based on the one or more features. As an example, and not by way of limitation, clinical features may comprise one or more of patient age at diagnosis, patient sex, patient height, patient weight, patient clinical history, patient sample type, or patient smoking history. As another example, and not by way of limitation, histologic features may comprise, for example, growth patterns such as solid, cribriform, micropapillary, papillary, acinar, or lepidic.

As described herein, a patch-embedding module 212 can generate an embedding (e.g., a lower-dimensional representation space) for each image patch in a corresponding feature embedding space. The embedding can be represented by the digital pathology image processing system 210 as a feature vector for the image patch. In some instances, the patch-embedding module 212 may use a neural network (e.g., a convolutional neural network) to generate a feature vector that represents each image patch of the image. In particular embodiments, the patch-embedding neural network can be based on, e.g., the ResNet image network trained on a dataset based on natural (e.g., non-medical) images, such as the ImageNet dataset. By using a non-specialized patch-embedding network, the patch-embedding module 212 can leverage known advances in efficiently processing images to generating embeddings. Furthermore, using a natural image dataset allows the embedding neural network to learn to discern differences between image patch segments on a holistic level.

In other embodiments, the patch-embedding network used by the patch-embedding module 212 can be an embedding network customized to handle large numbers of image patches of large format images, such as digital pathology WSIs. Additionally, the patch-embedding network used by the patch-embedding module 212 can be trained using a custom dataset. For example, the patch-embedding network can be trained using a variety of samples of WSIs or even trained using samples relevant to the subject matter for which the embedding network will be generating embeddings (e.g., scans of particular tissue types). Training the patch-embedding network using specialized or customized sets of images can allow the patch-embedding network to identify finer (e.g., more subtle) differences between image patches, which can result in more detailed and accurate distances between image patches in the feature embedding space at the potential cost of additional time to acquire the images and/or the computational and economic cost of training multiple patch-generating networks for use by the patch-embedding module 212. In some instances, the patch-embedding module 212 can select from a library of patch-embedding networks based on the type of images being processed by the digital pathology image processing system 210.

As described herein, image patch embeddings (e.g., lower-dimensional space) may be generated using a machine-learning model, e.g., a deep learning neural network, based on using visual features of the image patches. In some instances, the trained machine-learning model may thus function as, e.g., an image feature extraction model. Image patch embeddings can be further generated from contextual information associated with the image patches or from the content shown in the image patch. For example, an image patch embedding can include one or more features that indicate and/or correspond to a size of depicted objects (e.g., sizes of depicted cells or aberrations) and/or density of depicted objects (e.g., a density of depicted cells or aberrations). Size and density can be measured absolutely (e.g., based on dimensions expressed in pixels or converted from pixels to nanometers) or relative to other image patches from the same digital pathology image, from a class of digital pathology images (e.g., produced using similar techniques or by a single digital pathology image generation system or scanner), or from a related family of digital pathology images. Furthermore, image patches can be classified prior to the patch-embedding module 212 to generate embeddings for the image patches such that the patch-embedding module 212 considers the classification when preparing the embeddings.

For consistency, in some instances, the patch-embedding module 212 may produce embeddings of a predefined size (e.g., feature vectors of 512 elements, feature vectors of 2048 bytes, etc.). In some instances, the patch-embedding module 212 may produce embeddings of various and arbitrary sizes. The patch-embedding module 212 can adjust the sizes of the embeddings based on user direction, or size can be selected, for example, based on computation efficiency, accuracy, or other parameters. In particular embodiments, the embedding size can be based on the limitations or specifications of the deep learning neural network that generated the embeddings. Larger embedding sizes can be used to increase the amount of information captured in the embedding and improve the quality and accuracy of results, while smaller embedding sizes can be used to improve computational efficiency.

The digital pathology image processing system 210 can derive different inferences by apply one or more machine-learning models to the embeddings, i.e., inputting the embeddings to a machine-learning model. As an example, the digital pathology image processing system 210 can identify clusters of tumor cells, based on a machine-learning model trained to identify such structures. In some embodiments, it may be not necessary to crop the image into image patches, generate embeddings for these image patches, and then derive inferences based on such embeddings. Instead, in some instances, the digital pathology image processing system 210 with sufficient graphics processing unit (GPU) memory can directly apply the machine-learning model to the embedding of a WSI to make inferences. In some instances, the output of the machine-learning model may be resized into the shape of the input image.

A WSI access module 213 can manage requests to access WSIs from other modules of the digital pathology image processing system 210 and the user device 230. For example, the WSI access module 213 receive requests to identify a WSI based on a particular image patch, an identifier for the image patch, or an identifier for the WSI. The WSI access module 213 can perform tasks of confirming that the WSI is available to the requesting user or module, identifying the appropriate databases from which to retrieve the requested WSI, and retrieving any additional metadata that may be of interest to the requesting user or module. Additionally, the WSI access module 213 can handle efficient streaming the appropriate data to the requesting device. As described herein, in some instances, WSIs may be provided to user devices in portions, based on the likelihood that a user will wish to see the entire WSI or a portion of the WSI. In some instances, the WSI access module 213 may determine which regions of the WSI to provide and determine how to provide them. Furthermore, in some instances, the WSI access module 213 may be empowered within the digital pathology image processing system 210 to ensure that no individual component locks up or otherwise misuses a database or WSI to the detriment of other components or users.

A tumor heterogeneity assessment module 214 of the digital pathology image processing system 210 may apply one or more techniques to assess heterogeneity of tumor cells identified in one or more of the WSIs. In some embodiments, assessing tumor heterogeneity comprises classifying mutated tumor cells into phenotypes by identifying morphologically similar cells, e.g., by assessing nuclear heterogeneity. In some embodiments, assessing nuclear heterogeneity comprises quantifying certain features of cell nuclei to distinguish mutated cells based on nuclear morphologic heterogeneity.

In some embodiments, identifying tumor heterogeneity comprises identifying regions of clonal cells by conducting a cell-level spatial analysis to assess spatial distribution. In some embodiments, assessing spatial distribution comprises measuring spectral distances within subgraphs of a minimum spanning tree of tumor cells, wherein each of the subgraphs represents a cluster of adjacent cells (e.g., a tumor nest), and computing adjacency spectral distances pairwise across all of the subgraphs. In some embodiments, each of the subgraphs may be defined by performing outlier detection. In some embodiments, each of the subgraphs may be defined based on segmentation of detected tumor nests.

In some embodiments, identifying tumor heterogeneity comprises identifying regions of closely adjacent clonal cells by conducting a cell-level spatial analysis to assess spatial entropy. In some embodiments, assessing spatial entropy comprises computing, for each of a predefined number of distance bins, a frequency of pairs of cells identified as being morphologically similar.

A gene fusion prediction module 215 of the digital pathology image processing system 210 may apply one or more techniques to predict a likelihood (e.g., a binary output or a percentage output) that a gene fusion is present. In some embodiments, the gene fusion prediction module 215 may assess and/or aggregate results of assessing tumor heterogeneity, results of end-to-end prediction of gene fusions, results of assessing tumor morphology, and/or results of other approaches to arrive at a prediction (e.g., a score).

An output generating module 216 of the digital pathology image processing system 210 can generate output corresponding to one or more of image patches and one or more WSI datasets based on a user request. As described herein, the output can include a variety of visualizations, interactive graphics, and reports based upon the type of request and the type of data that is available. In some embodiments, the output will be provided to the user device 230 for display, but in certain embodiments the output may be accessed directly from the digital pathology image processing system 210. The output will be based on existence of and access to the appropriate data, so the output generating module will be empowered to access necessary metadata and anonymized patient information as needed. As with the other modules of the digital pathology image processing system 210, the output generating module 214 can be updated and improved in a modular fashion, so that new output features can be provided to users without requiring significant downtime.

The general techniques described herein can be integrated into a variety of tools and use cases. For example, as described, a user (e.g., pathology or clinician) can access a user device 230 that is in communication with the digital pathology image processing system 210 and provide a query image for analysis. The digital pathology image processing system 210, or the connection to the digital pathology image processing system can be provided as a standalone software tool or package that searches for corresponding matches, identifies similar features, and generates appropriate output for the user upon request. As a standalone tool or plug-in that can be purchased or licensed on a streamlined basis, the tool can be used to augment the capabilities of a research or clinical lab. Additionally, the tool can be integrated into the services made available to the customer of digital pathology image generation systems. For example, the tool can be provided as a unified workflow, where a user who conducts or requests a WSI to be created for a submitted sample automatically receives a report of noteworthy features within the image and/or similar WSIs that have been previously indexed. Therefore, in addition to improving WSI analysis, the techniques can be integrated into existing systems to provide additional features not previously considered or possible.

Moreover, the digital pathology image processing system 210 can be trained and customized for use in particular settings. For example, the digital pathology image processing system 210 can be specifically trained for use in providing insights relating to specific types of tissue (e.g., lung, heart, blood, liver, etc.). As another example, the digital pathology image processing system 210 can be trained to assist with safety assessment, for example in determining levels or degrees of toxicity associated with drugs or other potential therapeutic treatments. Once trained for use in a specific subject matter or use case, the digital pathology image processing system 210 is not necessarily limited to that use case. Training may be performed in a particular context, e.g., toxicity assessment, due to a relatively larger set of at least partially labeled or annotated images.

The methods and systems disclosed herein may enable users to easily request prognostic predictions based on digital pathology images provided by the user. In some instances, the digital pathology image processing system 210 may transmit, from a client computing system to a remote computing system, a request communication to process a digital pathology image that depicts cancer cells in a particular section of a biological sample from a subject. In response to receiving the request communication from the client computing system, the remote computing system may perform operations comprising the following steps. The remote computing system may first access the digital pathology image. The remote computing system may then segment the digital pathology image into a plurality of image patches, each depicting one or more clusters of tumor cells. The remote computing system may then generate, for each of the plurality of image patches, a label indicating a likelihood that the image patch depicts tumor heterogeneity. The remote computing system may then determine, based on the labels generated for each image patch, that the digital pathology image comprises a depiction of an occurrence of an actionable mutation with respect to the cancer cells. The remote computing system may then generate, based on the occurrence of gene fusion with response to the cancer cells, a prognostic prediction for the subject. In some instances, the prognostic prediction may comprise a prediction of applicability of one or more treatment regimens for the subject. The remote computing system may further provide the prognostic prediction to the client computing system via a response communication. In some instances, the client computing system may output the prognostic prediction in response to receiving the response communication.

FIG. 3 illustrates an example method 300 for detecting gene alterations, e.g., gene fusions. The method may include step 310, where the digital pathology image processing system 210 depicted in FIG. 3 may access a digital pathology image that depicts cancer cells in a particular section of a biological sample from a subject. As an example and not by way of limitation, the digital pathology image may be a scanned, stained (e.g., hematoxylin and eosin stained) WSI including tumorous cells (e.g., lung adenocarcinoma).

At step 320 in FIG. 3, the digital pathology image processing system 210 may segment the digital pathology image into a plurality of image patches, each depicting at least one cluster of tumor cells. In particular embodiments, the patch-generating module 211 depicted in FIG. 3 may be used to generate the image patches. The image patches may be non-overlapping or overlapping. Features such as whether or not image patches overlap, in addition to the size of each image patch and the step-wise displacement of the window used to create image patches can increase or decrease the data set for analysis, with more image patches increasing the potential resolution of eventual output and visualizations. In particular embodiments, each image patch may be of a predefined size and/or an offset between image patches may be predefined. Furthermore, the patch-generating module 211 may create multiple sets of image patches of varying size, overlap, step size, etc., for each image. The patch-generating module 211 may generate image patches for each digital pathology image in one or more color channels or for one or more color combinations. The image patches may be generated based on segmenting the color channels and/or generating a brightness map or greyscale equivalent of each image patch. Additionally, the digital pathology image processing system 210 can up-sample or down-sample images that are provided in particular color depth to be usable by the digital pathology image processing system 210. Furthermore, the digital pathology image processing system 210 can cause image patches to be converted according to the type of image that has been captured.

At step 330 in FIG. 3, the digital pathology image processing system 210 may generate, for each of the plurality of image patches, a label indicating a likelihood that the image patch depicts a cluster of tumor cells (e.g., tumor region or a tumor nest structure), such as one depicting an actionable mutation. As an example and not by way of limitation, the digital pathology image processing system 210 may detect one or more features from each of the plurality of image patches. The one or more features may comprise, e.g., one or more of a histologic feature, such as a cell type or cell grouping, a clinical feature, or a genomic feature. Accordingly, generating the label for each of the plurality of image patches may be based on the one or more features. In particular embodiments, generating the label for each of the plurality of image patches may be based on one or more of image patch-based classification or multi-instance learning (MIL) classification. Generating the label for each of the plurality of image patches may be based on the use of one or more trained machine-learning models. In particular embodiments, the digital pathology image processing system 210 may train the one or more machine-learning models based on a plurality of training data comprising one or more labeled depictions of a sample comprising, e.g., a tumor region or tumor nest structure, and one or more labeled depictions of a sample that does not include a tumor region or tumor nest structure. In particular embodiments, generating the label for each of the plurality of image patches may be based on tissue morphology, e.g., tumor morphology. The tumor morphology may be based on, for example, an analysis of one or more of the following histologic features: the presence or number of signet ring cells, the presence or number of hepatoid cells, extracellular mucin, or a tumor growth pattern.

At step 340 in FIG. 3, the digital pathology image processing system 210 may determine, based on the labels generated for each image patch, that the digital pathology image comprises a depiction of an occurrence of gene fusion with respect to the cancer cells in the image. In particular embodiments, the digital pathology image processing system 210 may use any of a variety of different approaches for effectively determining gene fusions that are present. One approach, for example, may comprise combining a target gene fusion (e.g., an NTRK fusion) with other gene fusions, such as ROS1, ALK, and RET fusions, into a single actionable gene fusion cluster. The cluster may be treated as a single category of gene fusion to facilitate detection. In this approach, rather than trying to identify each gene fusion individually, the digital pathology image processing system 210 instead treats them as a single group and thus is no longer required to detect gene fusions that occur individually with a frequency of less than half a percent. As an example, and not by way of limitation, the combined frequency of occurrence for these gene fusions may be about 15%.

The detection of actionable gene fusions may be based on one or more of: (i) automatic detection of histologic features, (ii) identification of mutually exclusive gene mutations (thereby identifying a lack of (or an absence) of a gene fusion), (iii) detection of NTRK gene fusions by grouping NTRK with ALK, ROS1, and RET into a single "actionable gene fusion cluster" and identifying the cluster, (iv) automatic detection of histologic features associated with ALK, ROS1, and RET (including solid and cribriform growth patterns, extracellular mucin, signet ring cells, goblet cells, and hepatoid cells), (v) identification and elimination of smoking-related mutational signatures, (vi) identification of low tumor mutation burden, (vii) assessment of tumor heterogeneity, or (viii) identification of pan-tumor or tumor-agnostic actionable gene fusion clusters using one or more end-to-end data-driven machine-learning model(s).

Another approach may comprise using the molecular landscape and molecular features of these tumors. In particular embodiments, signals for fusions may be primarily in tumor nests/cells and strong and diffuse across tumor area. Therefore, in addition to identifying gene fusions directly from the slide, the digital pathology image processing system 210 may identify gene fusions based on the mutually-exclusive distribution of molecular features across tumors.

In particular embodiments, the digital pathology image processing system 210 may indicate the occurrence of gene fusion to a pathologist as, for example, a comparison between a fusion positive slide image and the same field of view from this slide with an overlaid heatmap of gene fusion prediction. When comparing the two, the pathologist may see how a tumor detection algorithm in some embodiments disclosed herein rejected the image patches containing no tumor. In addition, confidence metric(s) of the prediction of gene fusion (as depicted, for example, by the intensity of the heatmap) may vary across the tumor area. Confidence metrics may be highest in areas with signet ring cells.

At step 350, the digital pathology image processing system 210 may generate, based on the detected occurrence of gene fusion with respect to the cancer cells, a prognostic prediction for the subject, wherein the prognostic prediction comprises a prediction of applicability of one or more treatment regimens for the subject. The digital pathology image processing system 210 may output, e.g., via a graphical user interface, the prognostic prediction. As an example and not by way of limitation, the digital pathology image processing system 210 may output a treatment regimen assessment. The digital pathology image processing system 210 may generate a recommendation associated with use of the one or more treatment regimens. For instance, the assessment may be that this patient is likely to have a gene fusion. As a subsequent or further step, digital pathology image processing system 210 may prompt a recommendation to perform a follow-up molecular test, such as a next-generation sequencing assay. In some embodiments, one or more steps of the method depicted in FIG. 3 may be repeated where appropriate. Although this disclosure describes and illustrates particular steps of the method of FIG. 3 as occurring in a particular order, this disclosure contemplates any suitable steps of the method of FIG. 3 occurring in any suitable order. Moreover, although this disclosure describes and illustrates an example method for detecting gene fusions (or other gene alterations), including the particular steps of the method depicted in FIG. 3, this disclosure contemplates any suitable method for detecting gene fusion, including any suitable steps, which may include all, some, or none of the steps of the method of FIG. 3, where appropriate. Furthermore, although this disclosure describes and illustrates particular components, devices, or systems carrying out particular steps of the method of FIG. 3, this disclosure contemplates any suitable combination of any suitable components, devices, or systems carrying out any suitable steps of the method of FIG. 3.

In some instances, the disclosed methods and systems may be applied to the detection of gene fusions/rearrangements, a specific type of rare, druggable oncogenic mutation event that can be identified across many different cancer types, that if present in a tumor tissue sample may indicate a robust response to certain targeted therapies. Gene fusions include rare, druggable mutation events that can occur across many different tumor types and are increasingly targeted by novel therapies. The identification of gene fusions can be a technically difficult, expensive, and time-consuming process that in the end may only benefit a minority of patients that carry such genetic alterations; for these reasons, widespread testing may be limited to the few hospitals that can afford to absorb and provide the technical and financial resources involved in this process. The embodiments disclosed herein may address this disparity through the creation, training, and use of machine-learning models (e.g., digital pathology screening models) that can predict the presence of oncogenic fusions from digital pathology images such as scanned, stained (e.g., hematoxylin and eosin stained) WSIs depicting cancer tissue/cells (e.g., lung adenocarcinoma). In addition, the embodiments disclosed herein may include fast, cheap, and sufficiently-accurate screening tools that may be used to guide molecular testing and decision-making regarding the use of targeted therapies for individual patients (including, but not limited to, lung adenocarcinoma patients).

In some instances, as noted elsewhere herein, the disclosed methods and systems may be used to identify gene fusions that are increasingly targeted by novel therapies. Targeted therapies for patients with tumors may include medicines that target epidermal growth factor receptor (EGFR), as well as the gene fusions involving anaplastic lymphoma kinase (ALK), RET, ROS1, and neurotrophic tyrosine receptor kinase (NTRK). For EGFR, although immunohistochemical stains can be used to identify the most common variants (e.g., with coverage of up to 97% of EGFR-positive lung adenocarcinoma patients), molecular testing may be required to identify resistance mutations in patients who have failed EGFR-targeted therapy. No such immunohistochemical stain has been developed for RET and ROS1, and the immunohistochemical stains for ALK and NTRK may be highly variable and difficult to interpret. Furthermore, gene fusions often require more sophisticated molecular assays with greater coverage of the genome than the more commonly used "hot spot" assays that test for a limited number of loci. To target gene fusions, one may need a much wider coverage resulting in a much more expensive test, which requires much more technical capacity for a laboratory to perform. As a result, a significant proportion of patients may be unlikely to receive the correct test to determine a likelihood that their tumors carry gene fusions. Aside from that, some gene fusions (e.g., NTRK fusion) may be exceedingly rare. Although NTRK fusions have been identified in a wide variety of tumor types, the frequency of this specific fusion may be less than 1% in the most common cancer indications (such as in lung adenocarcinoma, colorectal cancer, and non-secretory breast cancer). The relative rarity of gene fusions (e.g., ranging from 7% for ALK to less than 0.3% for NTRK in lung adenocarcinomas) constitute a significant technical and financial disincentive to widespread testing. Indeed, studies have shown that the patient populations who benefit most from these drugs are those who live close to academic institutions who have the expertise, infrastructure, and budget to perform complex laboratory tests. Currently, molecular testing is the only method available so far to determine a likelihood that gene fusion exists in patients. However, molecular testing is expensive and patients sometimes avoid scheduling molecular testing due to the expense and/or unnecessary expense is incurred for patients who may not benefit from molecular testing. The current embodiments present an improvement over current systems, in that the current embodiments may be used to identify patients that may benefit from molecular testing. In particular, the digital pathology image processing systems described herein may use a digital pathology machine-learning model to screen for patients who are likely to have gene fusions, and may then provide a recommendation that those patients get tested using molecular assays. As a result, the disclosed digital pathology image processing systems may improve the likelihood of detecting the gene fusions among patients, and may reduce the cost for follow-up molecular testing, thereby further benefiting and improving healthcare outcomes for those patients exhibiting gene fusions for which targeted therapies exist. The digital pathology model may be applicable to any suitable tumor type, although the embodiments disclosed herein contemplates applying the digital pathology model on lung adenocarcinoma as an example tumor type.

In particular embodiments, the digital pathology image processing system 210 may use different solutions for effectively detecting gene fusions. One solution may be combining a target gene fusion (e.g., NTRK fusion) with other gene fusions such as ROS1, ALK, and RET into a single actionable gene fusion cluster. The cluster may be then treated as a single category of gene fusion. Since the digital pathology image processing system 210 is not trying to identify each of these gene fusions individually but instead dealing with them as a single group, the digital pathology image processing system 210 may no longer deal with a frequency of less than half a percent of each gene fusion. As an example and not by way of limitation, the combined frequency of these gene fusions may be about 15%.

Another approach may comprise using the molecular landscape and molecular features of these tumors. In particular instances, signals for fusions may arise primarily in tumor nests/cells and may be strong and diffuse across the tumor area. Therefore, in addition to identifying fusions directly from the slide, the digital pathology image processing system 210 may identify gene fusions based on the mutually-exclusive distribution of molecular features across tumors. As an example and not by way of limitation, the morphology of lung adenocarcinoma may be mapped onto the molecular landscape, which may comprise, by way of example and not limitation, 17% EGFR-sensitizing, 7% ALK, 4% EGFR other, 3% having >1 mutation, 2% HER2, 2% ROS1, 2% BRAF, 2% RET, 1% NTRK1, 1% PIK3CA, 1% MEK1, 31% unknown oncogenic driver, and 25% KRAS alternations. Among the most common driver mutations of lung adenocarcinoma, only three percent may have greater than one mutation, which means that 97% of lung cancer patients carry a single mutation. It is therefore significantly more common for driver mutations to display mutual exclusivity, and this feature may be used in a variety of contexts to inform clinical decision making in the treatment of cancer patients. In some embodiments, the digital pathology image processing system 210 may access a digital pathology image that depicts cancer cells in a particular section of a biological sample from a subject. The digital pathology image processing system 210 may then determine that the digital pathology image comprises a depiction of one or more mutations that are mutually exclusive with an occurrence of gene fusion, and thus determine an absence of gene fusion with respect to the cancer cells. In some instances, the digital pathology image processing system 210 may further generate, based on the absence of gene fusion with respect to the cancer cells, a prognostic prediction for the subject. In particular embodiments, the digital pathology image processing system 210 may further generate, based on the absence of gene fusion with respect to the cancer, a prognostic prediction for the subject. The prognostic prediction may comprise, for example, a prediction of the applicability of one or more treatment regimens for the subject. Because of this mutual exclusivity, aside from positively identifying the gene fusion, the digital pathology model may identify more common mutations such as KRAS and EGFR and in doing so, rule out the presence of a gene fusion.

In particular embodiments, the digital pathology image processing system 210 may detect one or more features from each of the plurality of image patches. The one or more features may comprise one or more of a clinical feature or a histologic feature, such as a cell type. Accordingly, generating the label for each of the plurality of image patches may be based on the one or more features. As an example and not by way of limitation, clinical features may comprise one or more of younger age at diagnosis or an estimation of smoking history. In particular embodiments, predicting actionable gene fusion may be based on identifying and ruling out a smoking-related mutational signature. As another example and not by way of limitation, histologic features may comprise growth patterns such as solid, cribriform, micropapillary, papillary, acinar, or lepidic. In particular embodiments, predicting or determining that an actionable gene fusion is present may be based on the detection of histologic features associated with ALK, ROS1, and RET, including solid and cribriform growth patterns, and/or extracellular mucin. As another example and not by way of limitation, predicting or determining that an actionable gene fusion may be based on the detection of cell types associated with ALK, ROS1, and RET. These cell types may comprise one or more of signet ring cells, goblet cells, or hepatoid cells. Different features may have different levels of importance to different tumor types. Automatic detection and quantification of each of these visual features may allow for prediction of, for example, ALK, ROS1, RET and NTRK in, for example, lung adenocarcinoma.

In particular embodiments, another feature of fusions and tumors that may be used by the digital pathology image processing system 210 (or the digital pathology machine-learning model residing therein) for determining the presence of gene alterations, e.g., gene fusions, may be tumor mutational burden (TMB). In some instances, for example, kinase or oncogene fusions may be associated with low tumor mutational burden. A tumor's main oncogenic driver may be a single gene fusion. Therefore, one may expect that the morphologic signal derived from a single oncogenic driver would be present across the majority of tumor cells/ areas in a tissue specimen on a slide. End-to-end gene fusion status prediction may also show strong uniform signal across the whole slide.

In some instances, low tumor mutational burden may suggest decreased tumor morphologic heterogeneity. Patients may be characterized as having a driver mutation, a mutation in a driver gene, and/or a driver fusion (e.g., a gene fusion involving a driver gene). In some instances, the tumor mutational burden in cancers may be driven by a driver mutation. In some instances, the tumor mutational burden of cancers may be also driven by a gene fusion. In some instances, cancer driven by a gene fusion may have a significantly lower tumor mutational burden. Therefore, a low tumor mutational burden may be associated with a low tumor heterogeneity.

The digital pathology model may be generic across different tumor types. Therefore, the digital pathology image processing system 210 may identify and predict pan-tumor or tumor-agnostic actionable gene fusion based on the digital pathology model. As an example and not by way of limitation, the digital pathology image processing system 210 trained a digital pathology model on ALK fusion and ROS1 fusion, respectively, and the performance was the same. As another example, signal for NTRK may sort with ALK, ROS1, and RET. For instance, even though the digital pathology model has never used NTRK-based training data in training, it was able to identify NTRK fusion with the same accuracy as it has with the ROS1 fusion in the experiments of the embodiments disclosed herein. The generality of the digital pathology model may suggest that the features are consistent across different gene fusions as well as across different tumor types.

The embodiments disclosed herein may have a technical advantage of using easily accessible and less expensive material for analysis than corresponding molecular tests. In some embodiments, a section of the biological sample may be stained with one or more stains. As an example and not by way of limitation, the digital pathology image processing system may be used to scan, e.g., hematoxylin and eosin (H&E) stained slides; the original tissue specimen slides are readily available for use in any new or follow-up diagnostic analyses. By contrast, a molecular test may require cutting into the tissue block to sacrifice some tissue and use in sequencing, which would result in consumption of diagnostic tissue material. As can be seen, no tissue would be destroyed by using a digital pathology machine-learning model to analyze image data. In some instances, one may use the digital pathology image of a primary diagnostic slide for analysis without requiring extra slides. In some embodiments, a prognostic prediction may be generated based on further analysis of one or more additional digital pathology images. In some instances, each of the one or more additional digital pathology images may depict an additional section of the biological sample from the subject. In some embodiments, the analysis may comprise determining a likelihood that each of the one or more additional digital pathology images comprises a depiction of an occurrence of gene fusion with respect to the cancer cells, and combining the determination for each of the one or more additional digital pathology images. In some instances, after making a diagnosis with an H&E stained specimen slide, one may require additional unstained specimen slides (e.g., at least 5, 6, 7, 8, 9, 10 or more than 10 unstained specimen slides) to be sacrificed to perform the molecular test.

The embodiments disclosed herein may have another technical advantage of ease-of-use. One may scan the pathology specimen slide and input the scanned image, or image patch data derived therefrom, to the digital pathology machine-learning model. The digital pathology machine-learning model may then be used to make a prediction of a likelihood that a gene alteration, e.g., a gene fusion, is present in the biological sample. In some instances, the process may not require any annotation by a pathologist. In some instances, the pathologist may only have to correctly identify the slide as a target tumor type, e.g., lung adenocarcinoma. The embodiments disclosed herein may have another technical advantage of efficiency. As an example and not by way of limitation, the prediction of gene fusion may be completed in a matter of minutes, hours, or days, e.g., in less than 60 minutes, less than 50 minutes, less than 40 minutes, less than 30 minutes, less than 25 minutes, less than 20 minutes, less than 15 minutes, or less than 10 minutes.

In some instances, predicting or determining that an actionable gene fusion is present may be based, at least in part, on the detection of extracellular mucin. Excess extracellular mucin is reported to be indicative of fusion status and the disclosed methods for gene fusion status prediction may substantiate these findings. In some instances, the digital pathology image processing system 210 may predict gene fusion status in detail, identify differences between, e.g., resections and biopsies, determine precise segmentation of area, perform coarse detection of image patches containing extracellular mucin, and transition from tumor area detection to actual gene fusion status prediction. As an example and not by way of limitation, in some instances transitioning from tumor area detection to actual gene fusion status prediction may comprise determining a fraction of mucin detected versus tissue, or determining a fraction of mucin detected versus tumor.

In some instances, the digital pathology machine-learning model may be generically applicable across different tumor types. Therefore, the digital pathology image processing system 210 may be used to identify and predict pan-tumor or tumor-agnostic actionable gene fusion based on the use of the digital pathology machine-learning model. For example, the performance of a digital pathology image processing system 210 comprising a digital pathology machine-learning model trained on ALK fusion or on ROS1 fusion, respectively, was the same. As another example, the signal for NTRK fusions may sort with ALK, ROS1, and RET. For instance, even though a digital pathology machine-learning model was trained without using NTRK-based training data, it was able to identify NTRK fusions with the same accuracy as it had for detection of ROS1 fusions in experiments to test the methods disclosed herein. The general applicability of the digital pathology machine-learning model may suggest that the underlying image patch features used for prediction are consistent across different gene fusions as well as across different tumor types.

Figure 4:
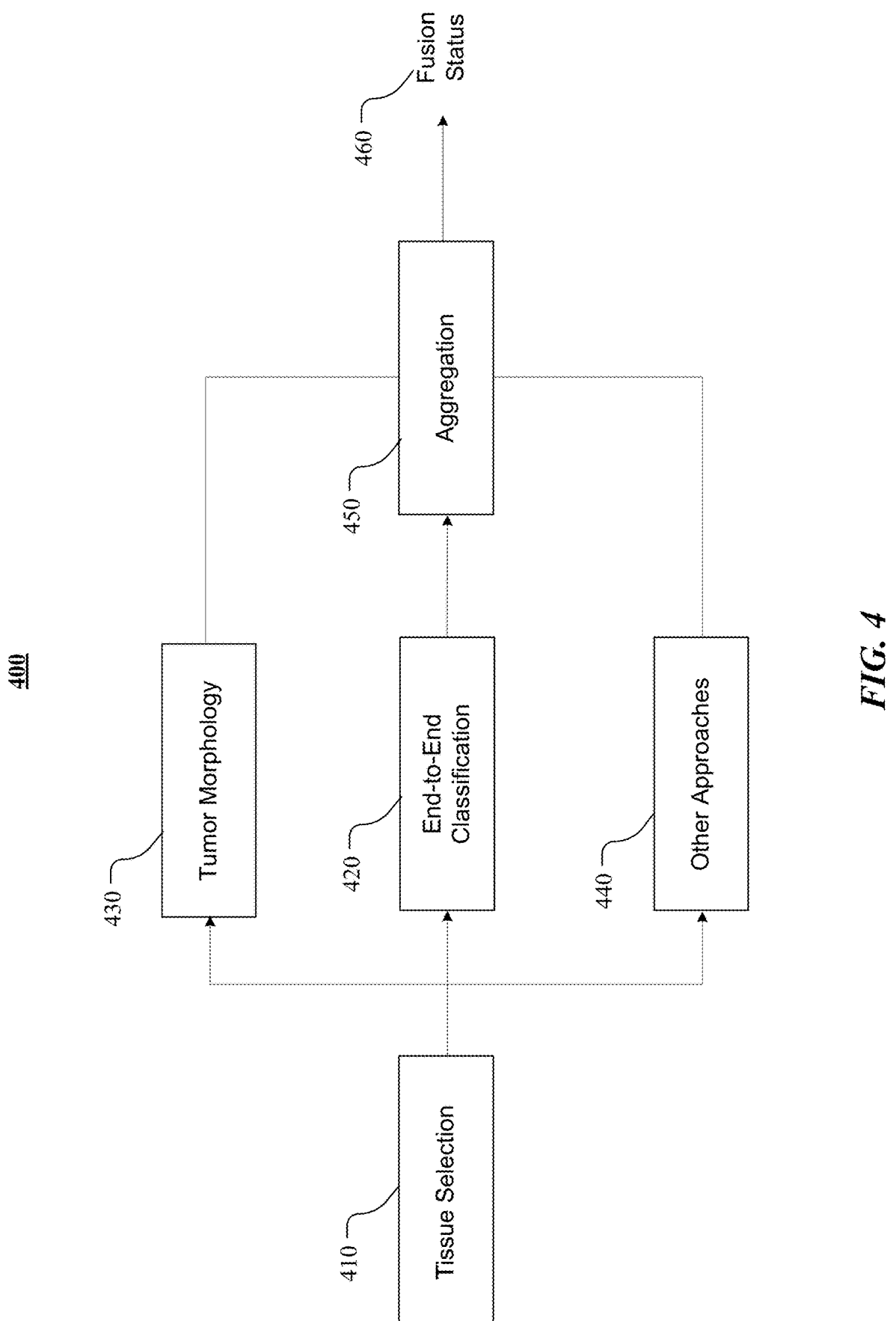
FIG. 4 is a workflow diagram for a non-limiting example pipeline for detecting gene fusion.

FIG. 4 illustrates an example workflow diagram for a process 400 for detecting gene fusion in a biological sample, e.g., a tissue specimen. The workflow 400 may start with tissue selection 410. In tissue selection 410, the digital pathology image processing system 210 may perform quality control and/or tumor detection. In particular embodiments, quality control and tumor region detection may comprise performing supervised classification tasks. For such tasks, the image patch-level accuracy may be sufficient and the digital pathology image processing system 210 may use, e.g., one binary classifier per task. The results of tissue selection 410 may then be provided as input to an end-to-end classification step 420. In some embodiments, the end-to-end classification 420 may be based on one or more of image patch-based classification or multi-instance learning (MIL) classification techniques as described above. As part of the end-to-end classification 420, generating a label for each of the plurality of image patches may be based on one or more machine-learning models. In some embodiments, the digital pathology image processing system 210 may train the one or more machine-learning models based on a plurality of training data comprising, e.g., one or more labeled depictions of a tumor region or tumor nest structure and one or more labeled depictions of other histologic or clinical features.

While the end-to-end classification 420 is being performed, the digital pathology image processing system 210 may perform a tumor morphology analysis 430. In some embodiments, generating the label for each of the plurality of image patches may be based on tumor morphology. The tumor morphology analysis 430 may comprise an analysis to identify of one or more of a signet ring cell, a hepatoid cell, extracellular mucin, or a tumor growth pattern. In some instances, growth pattern analysis may be helpful for gene fusion detection. As an example and not by way of limitation, lung adenocarcinomas may present with a number of growth patterns and with varying proportions of each. As another example and not by way of limitation, in some instances, solid and cribriform patterns may be associated with gene fusions. In some instances, the digital pathology image processing system 210 may determine influence of sample collection type (e.g., resection versus biopsy) on growth patterns. Since growth patterns are often large and homogeneous regions, image patch-level classification may be sufficiently accurate. In some embodiments, signet ring cell detection and hepatoid cell detection may both be associated with the presence of gene fusions. To detect such cells of interest, the digital pathology image processing system 210 may rely on object detection and localization. In some instances involving cell of interest detection, the digital pathology image processing system 210 may determine a relationship between detected cells and fusion status, e.g., based on the number or type of cells detected. In some instances, the digital pathology image processing system 210 may further perform fine-grained localization or image patch-level detection of cells.

The digital pathology image processing system 210 may also use other approaches 440 for gene fusion detection. As an example and not by way of limitation, in some instances, the digital pathology image processing system 210 may identify tumor heterogeneity (variability in the size, shape and staining of tumor cells) from the digital pathology image and measure the identified tumor heterogeneity. Correspondingly, in some instances, determining that the digital pathology image may comprise a depiction of the occurrence of gene fusion may be further based on the measured tumor heterogeneity.

The digital pathology image processing system 210 may then perform aggregation step 450 on the results from tumor morphology analysis 430, end-to-end classification 420, and other approaches 440. Aggregation of results may be performed using any suitable approach (e.g., using ensemble classification or by generating all intermediate results by all sub-tasks and subsequently training another classification model that consumes all of the intermediate results to output a joint prediction). The aggregated results may be used to predict the fusion status 460 for the tissue specimen. In some embodiments, the fusion status prediction may be a weakly-supervised classification task (e.g., in which slide-level labels may be available). In some instances, the digital pathology image processing system 210 may use a multi-instance learning (MIL) approach to classify a plurality of image patches. In some instances, the digital pathology image processing system 210 may use a simplified strategy comprising the assignment of a slide label to all image patches. In particular embodiments, determining that the digital pathology image comprises the depiction of the occurrence of gene fusion with respect to the cancer cells may be further based on a weighted combination of the labels generated for each image patch. As an example and not by way of limitation, in some instances, the digital pathology image processing system 210 may use a binary classifier to classify image patches and then determine slide-level prediction by combining (e.g., averaging) all image patch predictions.

In particular embodiments, the digital pathology image processing system 210 may output, via a graphical user interface, the prognostic prediction. In some instances, the graphical user interface may comprise a graphical representation of the digital pathology image. In some instances, the graphical representation may comprise an indication of the label generated for each of a plurality of image patches and a predicted level of confidence associated with the respective label. In some instances, the output of the digital pathology image processing system 210 may also comprise other information as follows. As an example and not by way of limitation, the digital pathology image processing system 210 may output a treatment regimen assessment. The digital pathology image processing system 210 may generate a recommendation associated with use of one or more treatment regimens for the subject or patient from which the biological sample was derived. For instance, the assessment may be that a sample from a given subject or patient is likely to have a gene fusion, so confirmation by a follow-up molecular assay is recommended. As another example and not by way of limitation, the digital pathology image processing system 210 may output a negative result, i.e., there is no gene fusion predicted or detected. As yet another example and not by way of limitation, the digital pathology image processing system 210 may output "insufficient for analysis". For example, "insufficient for analysis" may be due to either the tumor size or the slide (e.g., the tumor specimen was too small and/or the pathology slide quality was hampered by the amount of tissue handling artifacts). For instance, the microtome blade used in cutting a tissue section may produce a series of parallel tears across the slide. These types of sampling processing artifacts may prevent the digital pathology machine-learning model(s) used to analyze the pathology slide image from making an accurate prediction.

The embodiments disclosed herein may enable users to easily request prognostic predictions based on digital pathology images from the user end. In particular embodiments, the digital pathology image processing system 210 may transmit, from a client computing system to a remote computing system, a request communication to process a digital pathology image that depicts cancer cells in a particular section of a biological sample from a subject. In response to receiving the request communication from the client computing system, the remote computing system may perform operations comprising the following steps. The remote computing system may first access the digital pathology image. The remote computing system may then segment the digital pathology image into a plurality of image patches, each depicting one or more clusters of tumor cells. The remote computing system may then generate, for each of the plurality of image patches, a label indicating a likelihood that the image patch depicts a tumor region or a tumor nest structure. The remote computing system may then determine, based on the labels generated for each image patch, that the digital pathology image comprises a depiction of an occurrence of gene fusion with respect to the cancer cells. The remote computing system may then generate, based on the occurrence of gene fusion with response to the cancer cells, a prognostic prediction for the subject. In particular embodiments, the prognostic prediction may comprise a prediction of applicability of one or more treatment regimens for the subject. The remote computing system may further provide the prognostic prediction to the client computing system via a response communication. Particular embodiments may further output, by the client computing system in response to receiving the response communication, the prognostic prediction.

FIGS. 5A-5D illustrate example actionable fusion prediction in lung adenocarcinoma. FIG. 5A illustrates a non-limiting example of pathology slide images for lung adenocarcinoma. The left image 505 is a slide for metastatic lung adenocarcinoma with ROS1 fusion. The right image 510 is a slide for lung adenocarcinoma with an EGFR mutation. FIG. 5B illustrates a non-limiting example of results from quality control. As illustrated in FIG. 5B, the quality control process may identify tissue 515, marker 520, blur 525, and combined image features 550. FIG. 5C illustrates a non-limiting example of tumor region detection. As illustrated in FIG. 5C, the darker the region, the more likely it is a tumor region. FIG. 5D illustrates a non-limiting example of prediction of fusion status. As illustrated in FIG. 5D, the darker the region the more likely it comprises a gene fusion.

FIG. 6 illustrates a non-limiting example of prediction of ROS1 gene fusion status. The images shown in FIG. 6 are examples of the final output that may be provided to the pathologist. The left image 610 indicates a fusion positive slide for metastatic lung adenocarcinoma comprising a ROS1 fusion. The right image 620 indicates the same field of view from image 610 with an overlaid heatmap of gene fusion prediction. When comparing the two images, one can see how the tumor detection algorithm rejected the image patches containing no tumor. In addition, confidence metric(s) of the prediction (as depicted by the intensity of the heatmap) may vary across the tumor area. Confidence metrics may be highest in areas with signet ring cells. As can be seen, the digital pathology image processing system 210 may provide output in formats that make clear to the pathologist that the digital pathology model is based on interpretable morphologic features.

Figure 7:
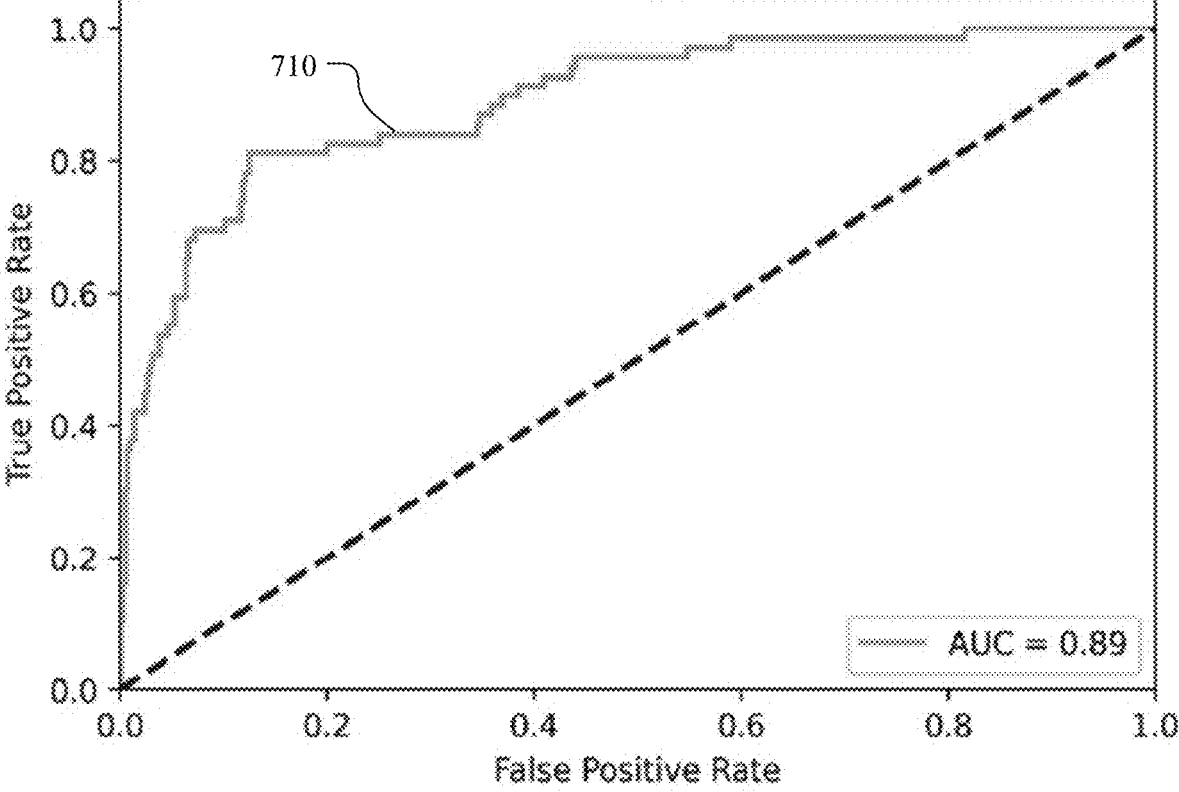
FIG. 7 illustrates a non-limiting example of an ROC curve for image patch-based fusion prediction.

Experiments on actionable fusion prediction in lung adenocarcinoma were conducted to validate the digital pathology model and methods disclosed herein. FIG. 7 illustrates a non-limiting example of a receiver operating characteristic (ROC) curve 710 for image patch-based fusion prediction. The training set for the digital pathology model comprises 270 resections. 18.5% of them are fusion positive, i.e., 50 slides derived from 5 patients. Among these fusion positive slides, 5 slides are ALK fusion positive and 45 slides are ROS1 fusion positive. The test set comprises 598 resections and biopsies. 11% of them are fusion positive, i.e., 68 slides. Among these fusion positive slides, 8 slides were NTRK fusion positive and 60 slides were ROS1 fusion positive. For a cut-off set at 0.5, the performance statistics are as follows: the positive predictive value (PPV) is 0.46 and negative predictive value (NPV) is 0.97, with an overall area under the curve (AUC) of 0.89.

In particular embodiments, extracellular mucin signal in end-to-end results may be as follows. Excess extracellular mucin is reported to be indicative of fusion status and end-to-end fusion status prediction may substantiate this assumption. Strong signal in mucin pools may be observable. In particular embodiments, the digital pathology image processing system 210 may additionally predict fusion status in detail, identify differences between resections and biopsies, determine precise segmentation of area, perform coarse detection of extracellular mucin containing image patches, and transition from area to actual fusion status prediction. As an example and not by way of limitation, transitioning from area to actual fusion status prediction may comprise determining fraction of mucin versus tissue or determining fraction of mucin versus tumor.

In particular embodiments, diffuse fusion signal in end-to-end predictions may be as follows. Kinase or oncogene fusions may be associated with low tumor mutational burden. A tumor's main oncogenic driver may be a single gene fusion. Therefore, one would expect that the morphologic signal derived from a single oncogenic driver would be present across the majority of tumor cells/areas on a slide. End-to-end fusion status prediction may also show strong uniform signal across the whole slide.

FIG. 8 illustrates an example method 800 for enabling end users utilizing a client computing system to request prognostic predictions from a digital pathology image processing system 210 based on processing of digital pathology images (by a remote computing system performing the steps in method 300). The method may begin at step 810, where the digital pathology image processing system 210 depicted in FIG. 2 may transmit, from a client computing system to a remote computing system, a request communication to process a digital pathology image that depicts cancer cells in a particular section of a biological sample from a subject, wherein in response to receiving the request communication from the client computing system, the remote computing system performs operations comprising the following sub-steps. At sub-step 810*a*, the remote computing system may access the digital pathology image. At sub-step 810*b*, the remote computing system may segment the digital pathology image into a plurality of image patches. At sub-step 810*c*, the remote computing system may generate, for each of the plurality of image patches, a label indicating a likelihood that the image patch depicts, e.g., a tumor region or a tumor nest structure. At sub-step 810*d*, the remote computing system may determine, based on the labels generated for each image patch, that the digital pathology image comprises a depiction of an occurrence of gene fusion with respect to the cancer cells. At sub-step 810*e*, the remote computing system may generate, based on the occurrence of gene fusion with respect to the cancer cells, a prognostic prediction for the subject, wherein the prognostic prediction comprises a prediction of applicability of one or more treatment regimens for the subject. At sub-step 810*f*, the remote computing system may provide the prognostic prediction to the client computing system via a response communication. At step 820, the computing system may output, in response to receiving the response communication, the prognostic prediction. In some instances, one or more steps of the method depicted in FIG. 8 may be repeated where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for enabling end users to request prognostic predictions, including the particular steps of the method of FIG. 8, this disclosure contemplates any suitable method for enabling end users to request prognostic predictions, including any suitable steps, which may include all, some, or none of the steps of the method of FIG. 8, where appropriate. Furthermore, although this disclosure describes and illustrates particular components, devices, or systems carrying out particular steps of the method of FIG. 8, this disclosure contemplates any suitable combination of any suitable components, devices, or systems carrying out any suitable steps of the method of FIG. 8.

FIG. 9 illustrates an example method 900 for predicting an alternate treatment based on identifying a lack of gene fusion with respect to a set of detected cancer cells. The method may begin at step 910, where the digital pathology image processing system 210 shown in FIG. 2 may access a digital pathology image that depicts cancer cells in a particular section of a biological sample from a subject. At step 920, the digital pathology image processing system 210 may determine that the digital pathology image comprises a depiction of one or more mutations that are mutually exclusive with an occurrence of gene fusion. At step 930, the digital pathology image processing system 210 may determine an absence of gene fusion with respect to the cancer cells. At step 940, the digital pathology image processing system 210 may generate, based on the absence of gene fusion with respect to the cancer cells, a prognostic prediction for the subject, wherein the prognostic prediction comprises a prediction of applicability of one or more treatment regimens for the subject. In some instances, one or more steps of the method of FIG. 9 may be repeated, where appropriate. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates an example method for ruling out gene fusion, including the particular steps of the method of FIG. 9, this disclosure contemplates any suitable method for identifying a lack (or an absence) of gene fusion, including any suitable steps, which may include all, some, or none of the steps of the method of FIG. 9, where appropriate. Furthermore, although this disclosure describes and illustrates particular components, devices, or systems carrying out particular steps of the method of FIG. 9, this disclosure contemplates any suitable combination of any suitable components, devices, or systems carrying out any suitable steps of the method of FIG. 9.

In some embodiments, identifying tumor heterogeneity comprises classifying mutated tumor cells into phenotypes based on morphologic features of the mutated tumor cells and an assessment of a spatial distribution of the mutated tumor cells in each of the phenotypes. The mutational context, or the manner in which the tumor cells are mutating, may vary from a high heterogeneity mutational context (e.g., tumor suppressor and/or unknown driver, which may be prognostic of a response to immunotherapy) to an intermediate heterogeneity mutational context (e.g., an oncogene mutation, which may be prognostic of a response to a targeted therapy for the oncogene mutation) to a low heterogeneity, a.k.a. homogenous or clonal, mutational context (e.g., a gene fusion, which may be prognostic of a response to a specific type of targeted therapy for a particular gene fusion).

Figure 10A:
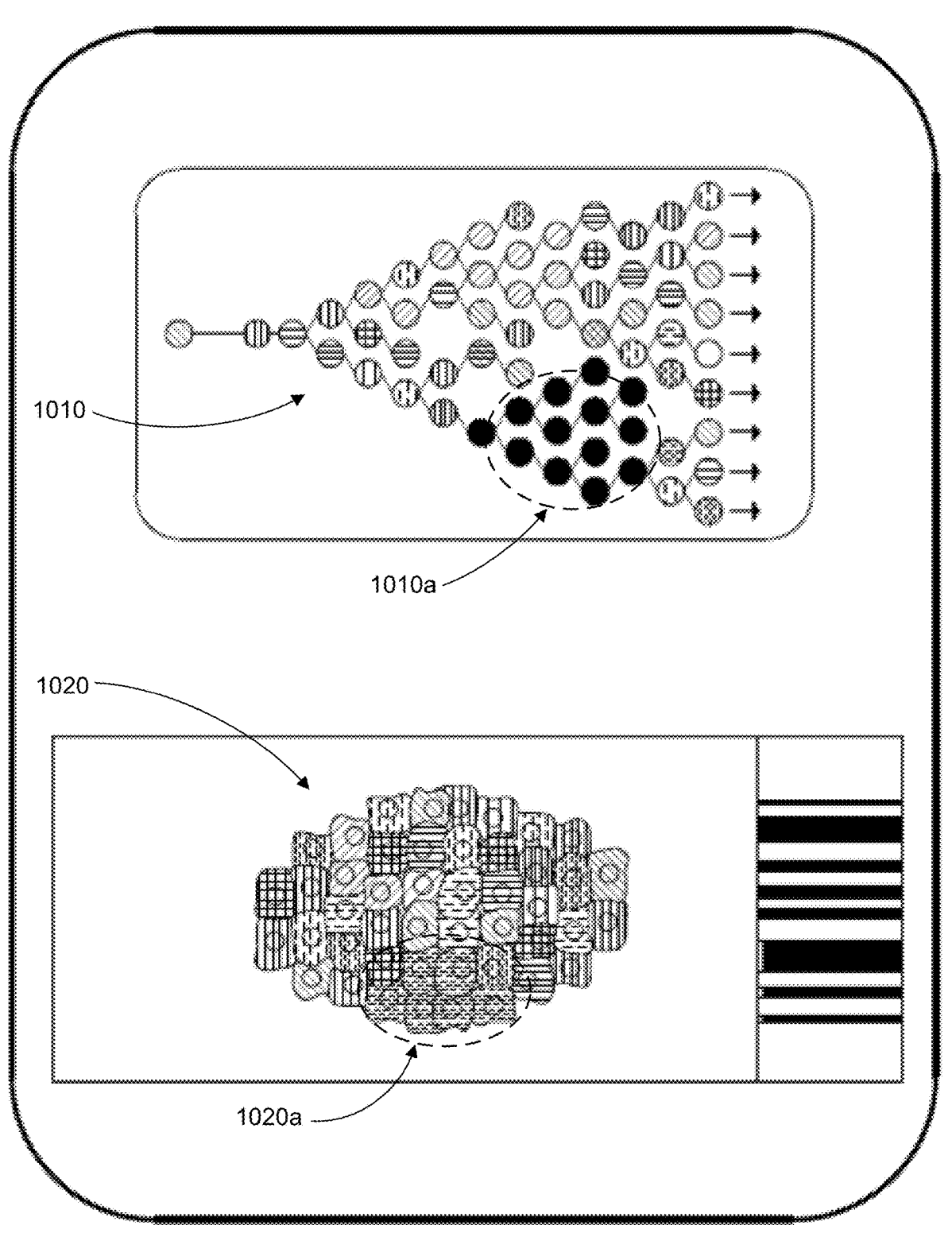
FIG. 10A is a schematic illustration of tumor heterogeneity when the mutational context corresponds to a tumor suppressor alone, such as pathogenic variants in KEAP1, STK11, or TP53; and/or unknown driver.
Figure 10B:
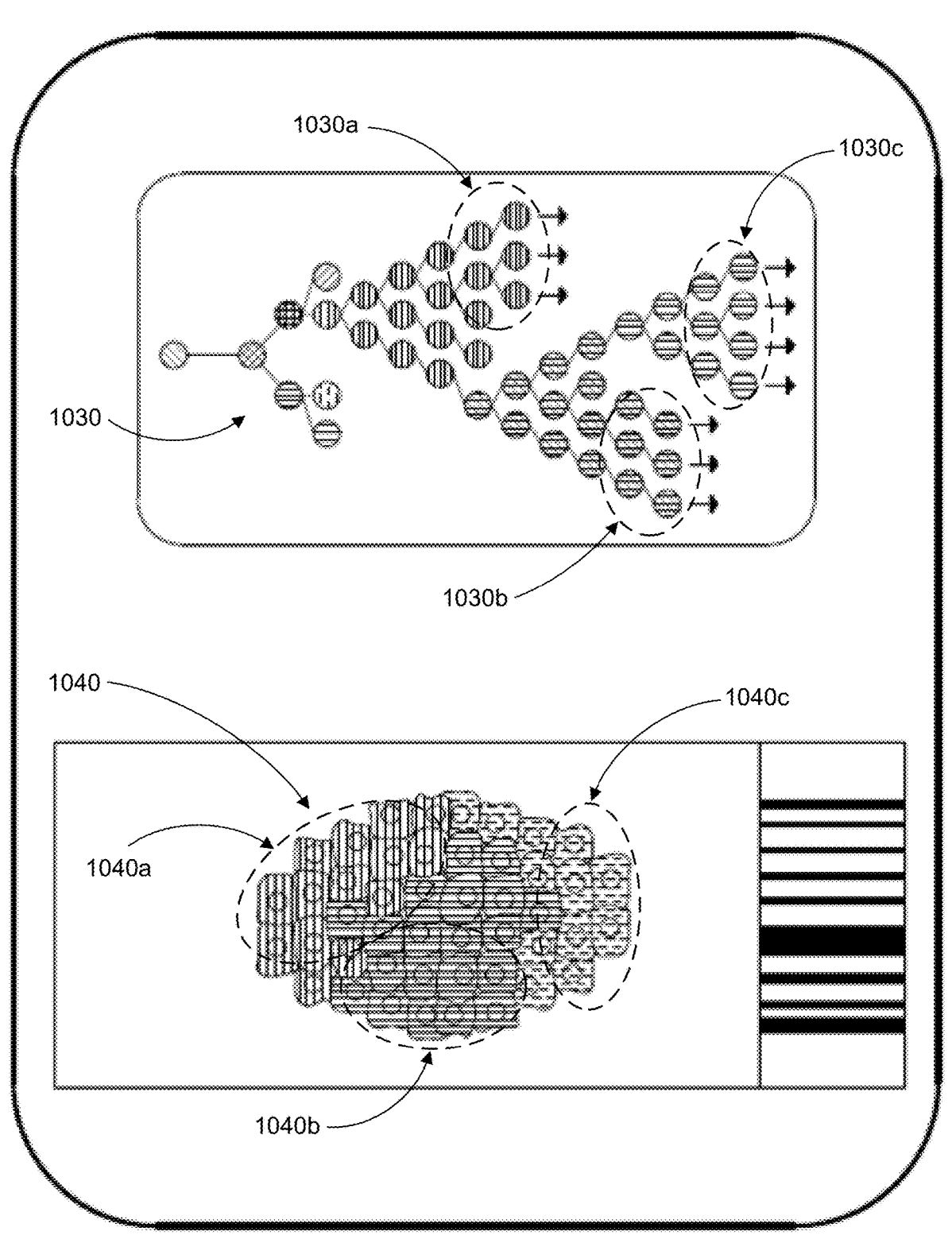
FIG. 10B is a schematic illustration of tumor heterogeneity when the mutational context corresponds to an oncogene driver mutation, such as pathogenic variants in EGFR, KRAS, or PIK3CA.
Figure 10C:
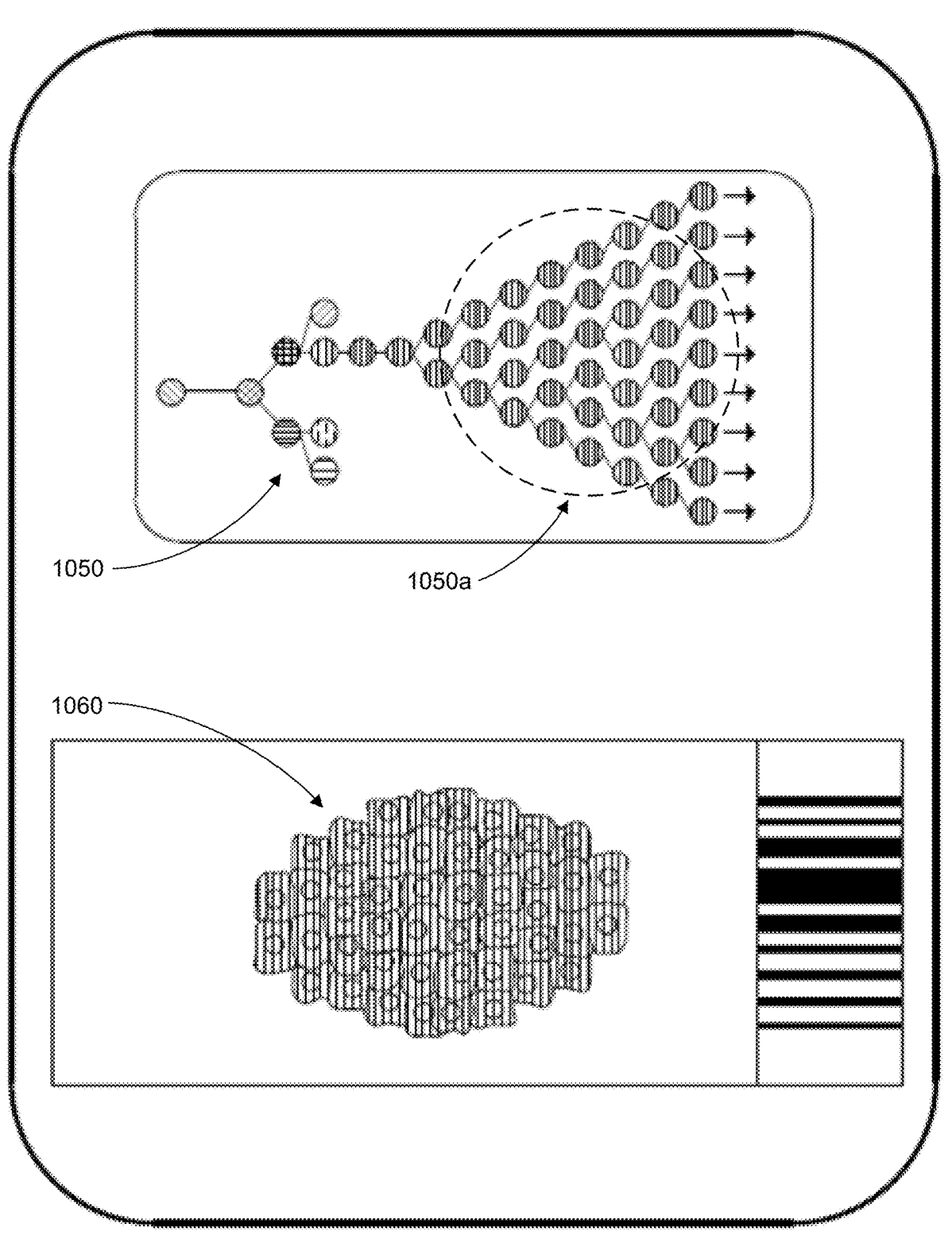
FIG. 10C is a schematic illustration of tumor heterogeneity when the mutational context corresponds to an oncogene fusion, such as ALK, RET, ROS1, or NTRK.

FIGS. 10A-10C are schematic illustrations of an example representation of a mutational context, as shown in the upper window, illustrated above an example representation of the corresponding visual signature (e.g., morphological features of a cluster of tumor cells captured in a WSI) as shown in the lower window. As illustrated, the representation of the mutational context illustrates how heterogeneity increases or decreases (both overall and within single-phenotype clusters of tumor cells) as tumor cells mutate and multiply. Different tumor cell phenotypes are represented by circles with different fill patterns.

FIG. 10A is a schematic illustration of an example representation of mutational context 1010-*a* tumor suppressor and/or unknown driver- and its corresponding visual signature 1020. The high level of heterogeneity as between the tumor cells can be observed in the morphological features. Example visual signatures distinguishing the mutational context of a tumor suppressor and/or unknown driver from other mutational contexts include a high degree of phenotype variation between tumor cells and uneven spatial distribution of tumor cells as between different phenotypes. As shown by the cluster of tumor cells 1010*a* (indicated with a dashed line), the phenotype represented by the darkened circles may be, by way of example and not limitation, tumor cells with a particular range of nucleus area as measured and a certain level of angularity to the nucleus border. Region 1020*a* of visual signature 1020 depicts the example representation of the corresponding visual signature of that example phenotype (i.e., the tumor cells with a certain nucleus area as measured and a certain level of angularity to the nucleus border).

FIG. 10B is a schematic illustration of an example representation of mutational context 1030—an oncogene driver mutation (e.g., an EGFR mutation)—and its corresponding visual signature 1040. The intermediate level of heterogeneity as between the tumor cells can be observed in the morphological features. Example visual signatures distinguishing the mutational context of an oncogene driver mutation from other mutational contexts include clusters of various phenotypes of tumor cells and variance in spatial distribution as between different clusters of tumor cells, but also close, equidistant spatial distribution as between tumor cells within a cluster. As shown by the clusters of tumor cells 1030*a*, 1030*b*, and 1030*c* (indicated with a dashed lines), the three phenotypes represented by those clusters may be, by way of example and not limitation, tumor cells with three distinct ranges of the ratio of pixels in the nucleus to pixels in a bounding box in a selected area of a field of view. Regions 1040*a*, 1040*b*, and 1040*c* of visual signature 1040 (corresponding to clusters 1030*a*, 1030*b*, and 1030*c*, respectively) depict the example representations of the corresponding visual signatures of those three example phenotypes.

FIG. 10C is a schematic illustration of an example representation of mutational context 1050—an oncogene fusion (e.g., ALK, NTRK, ROS1, RET)—and its corresponding visual signature 1060. The high degree of homogeneity (i.e., low or nonexistent heterogeneity, a.k.a. a clonal appearance) as between the tumor cells can be observed in the morphological features. Example visual signatures distinguishing the mutational context of an oncogene fusion from other mutational contexts include the low degree of (or nonexistent) phenotype variation in the tumor cells and close, equidistant spatial distribution of tumor cells. As shown by the cluster of tumor cells 1050*a* (indicated with a dashed line), the phenotype represented by that cluster may be, by way of example and not limitation, tumor cells with a particular pixel intensity value. Visual signature 1060 depicts the example representation of the corresponding visual signature of that example phenotype (i.e., a homogeneous cluster of cells of a single phenotype).

FIG. 11 is a flowchart for a non-limiting example method 1100 for identifying tumor heterogeneity. At step 1110, a digital pathology image that depicts tumor cells taken from a subject may be accessed, either through retrieval (e.g., from a database or online repository) or by scanning a WSI using a digital pathology image generation system 220. The digital pathology image may have been previously identified as one depicting tumor cells (e.g., by a human pathologist, or by a digital pathology image processing system 210). At step 1120, patches may be selected from the digital pathology image. In these patches, tumor cells may have been annotated, the nuclei segmented, and nuclei masks generated. At step 1130, the tumor cells may be classified into clusters of phenotype comprising shared nuclear morphological features based on assessing nuclear morphological features (e.g., as listed below), each of the phenotypes corresponding to a different mutation. In some embodiments, other morphological features of the tumor cells, sub-structures thereof, and/or of the stroma or other nearby cells may also be assessed. At step 1140, the tumor cells may be grouped, by phenotype and location, into clusters representing tumor regions or nests. Grouping the tumor cells by phenotype may include by the assessing the tumor cells based on morphological features. Grouping the tumor cells by location may include generating a minimum spanning tree and using outlier detection to split the tree into subgraphs, by segmenting tumor nests as depicted, or by any other suitable technique. At step 1150, spatial distances between cells in each of the clusters may be quantified. The spatial distances may be quantified by computing adjacency spectral distance, pairwise for all graphs in the WSI. The spatial distances may also be quantified by measuring spatial entropy to identifying closely adjacent clonal cells. At step 1160, a likelihood that an actionable mutation is present may be predicted based on the classified tumor cells, the identified clusters, or the quantified spatial distances. At step 1170, based on the patch-level predictions, a prognostic prediction may be generated for the subject, wherein the prognostic prediction comprises a prediction of response to one or more treatment regimens for the subject.

Figure 12A:
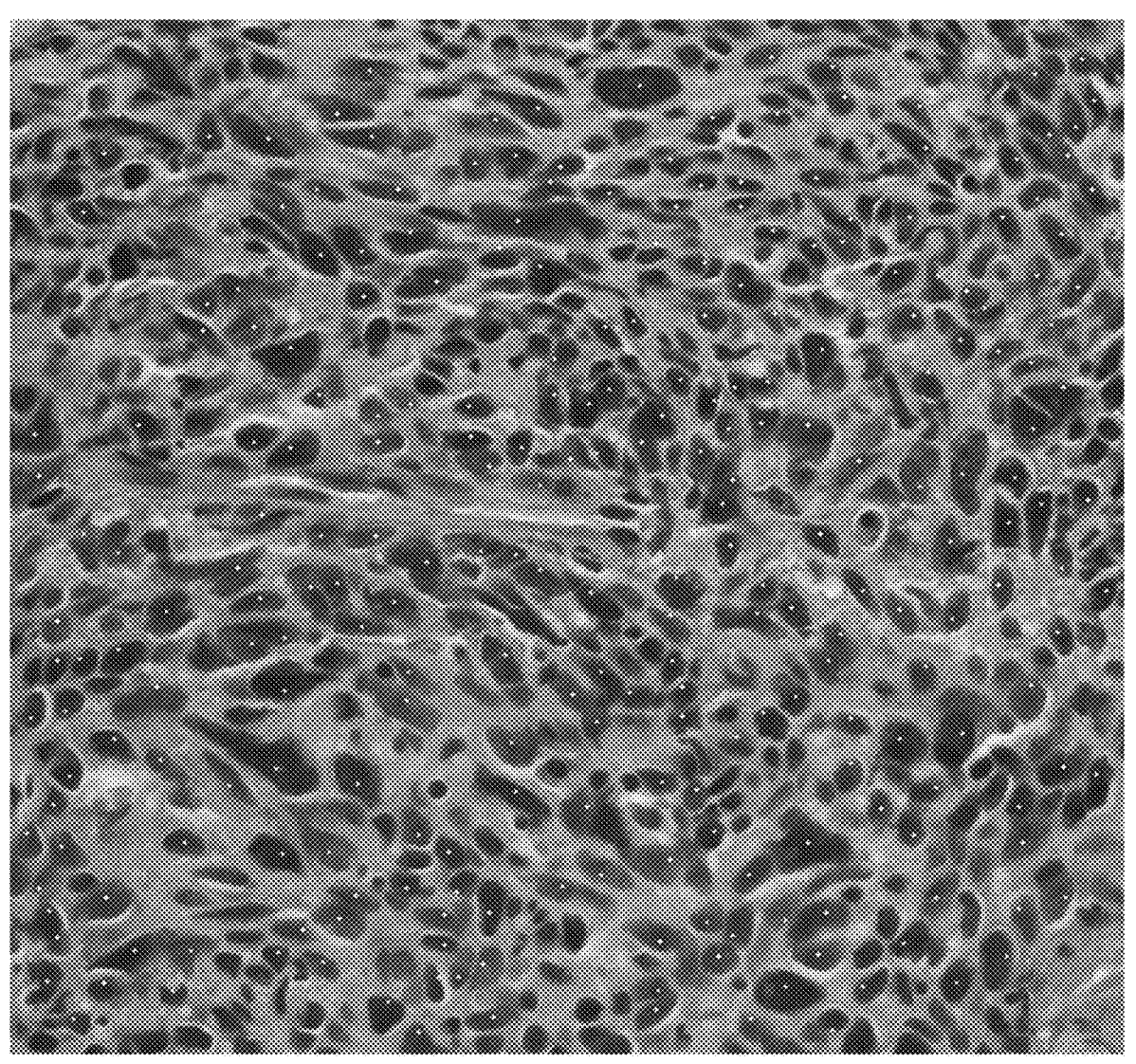
FIGS. 12A-12C depict non-limiting examples of tumor cell annotation, nuclei segmentation, and nuclei mask generation.
Figure 12B:
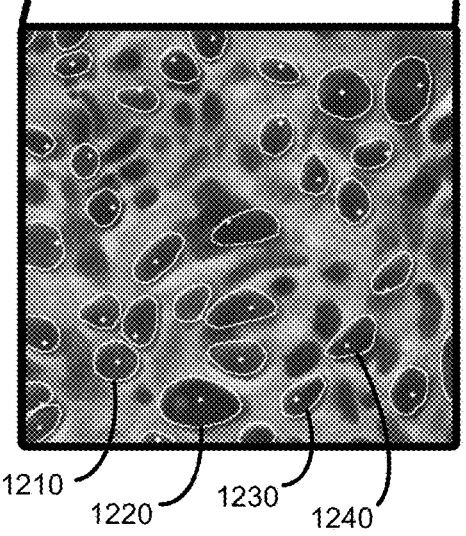
Figure 12C:
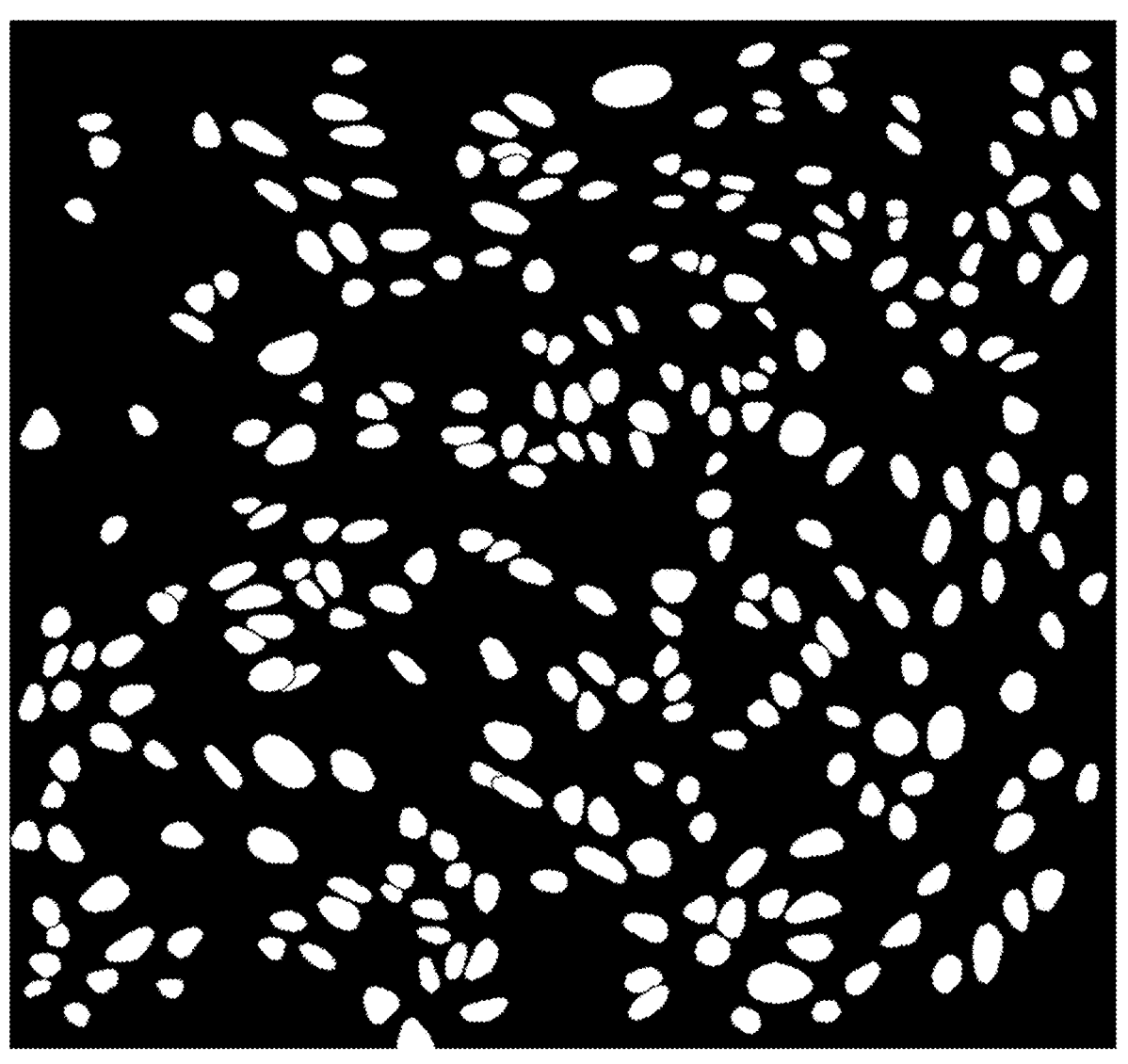
Figure 13A:
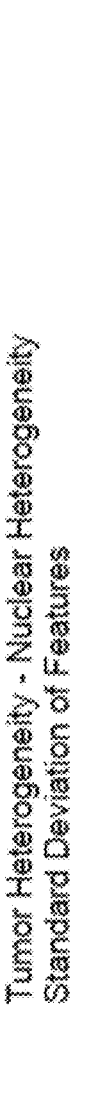
Figure 13C:
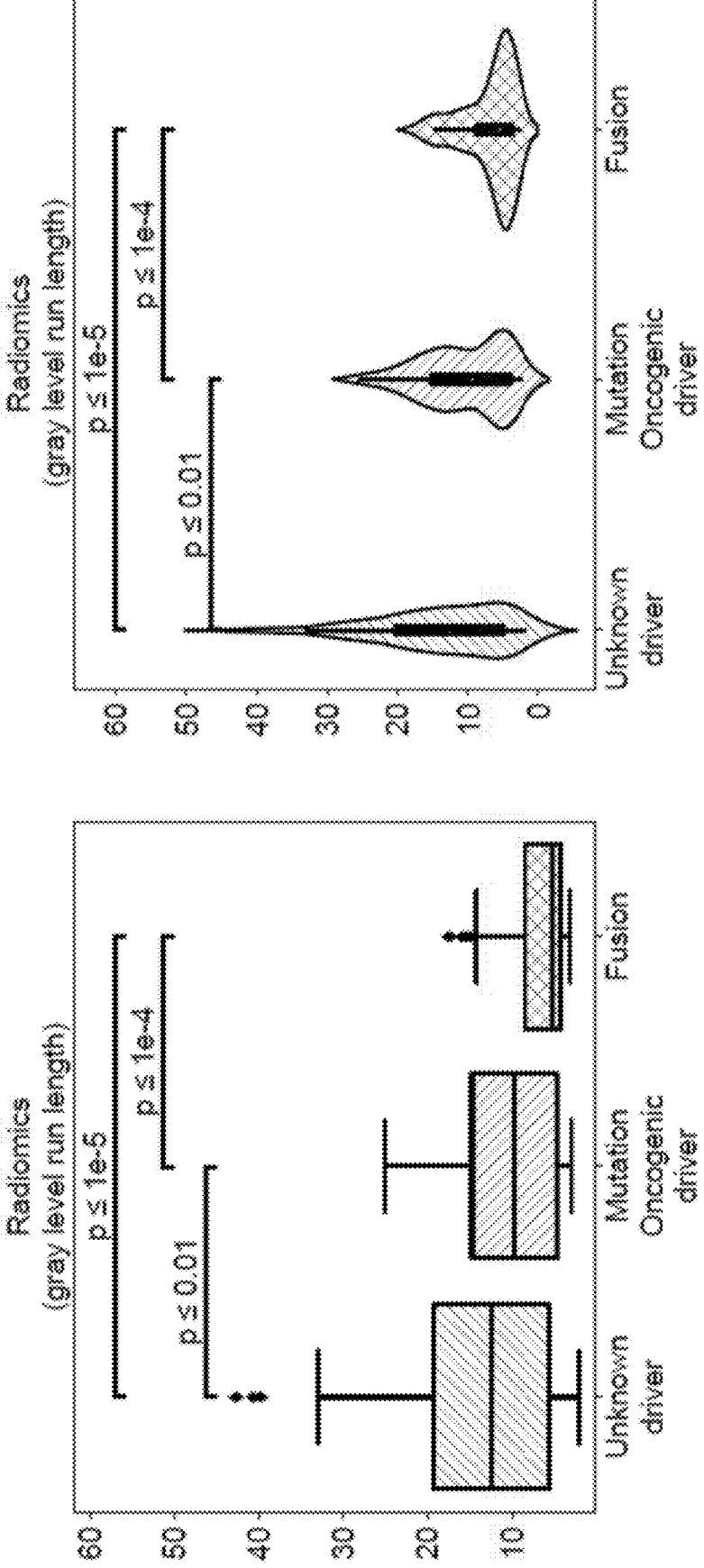
Figure 13D:
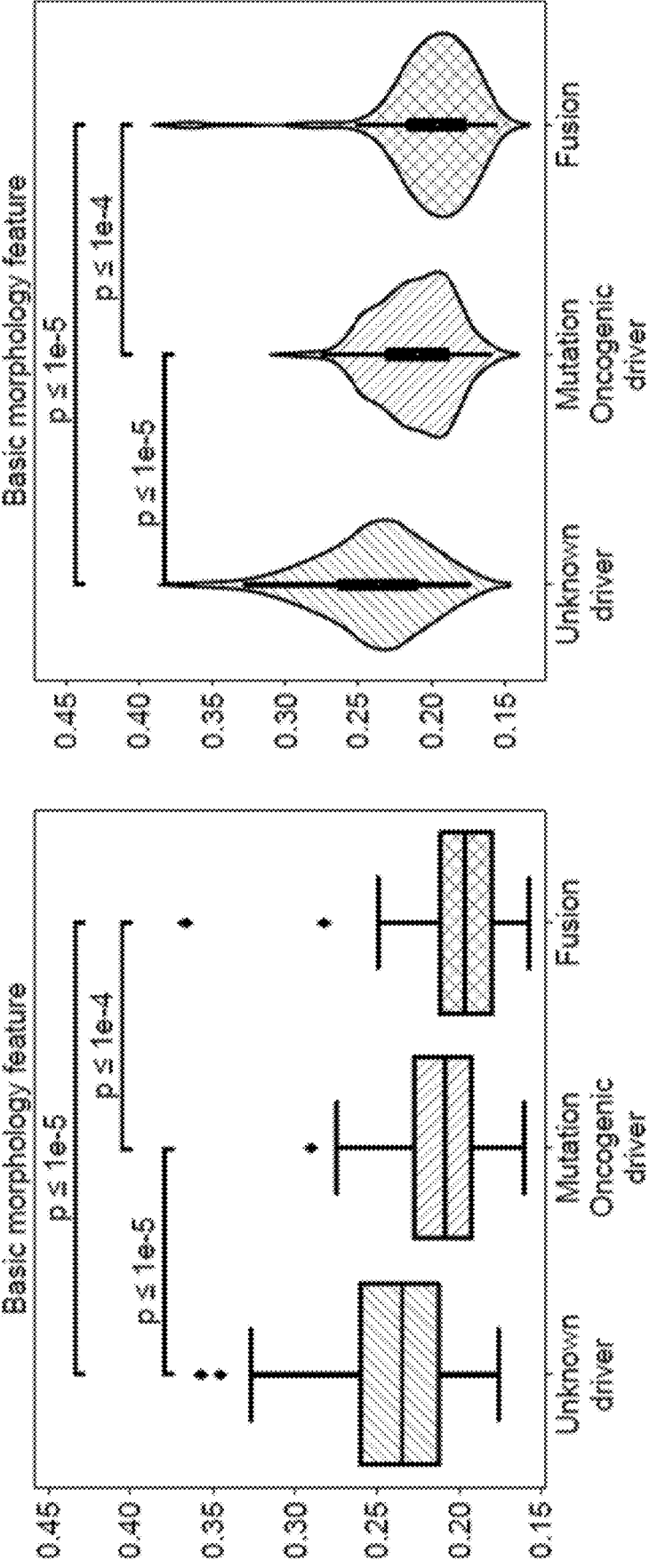
Figure 13E:
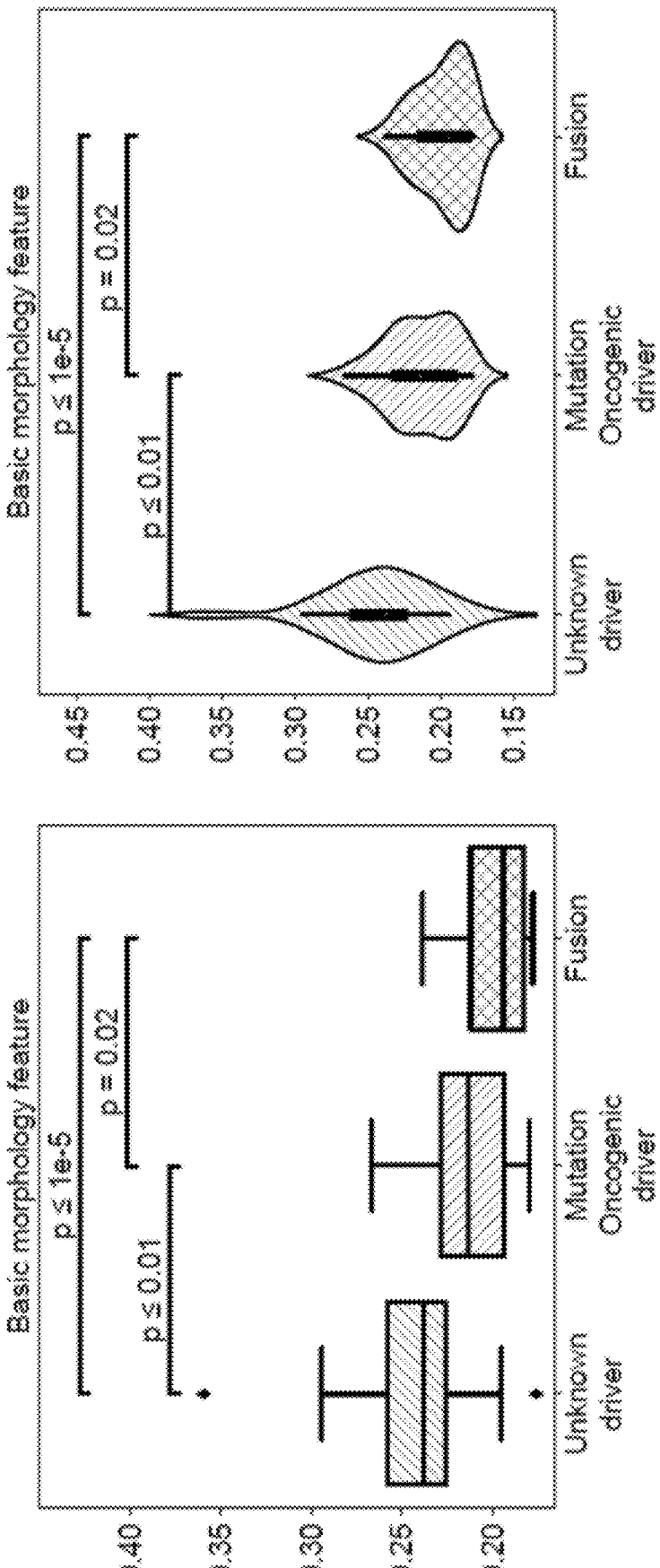

FIGS. 12A-12C depict non-limiting examples of tumor cell annotation, nuclei segmentation, and nuclei mask generation. As shown in FIG. 12A, the location of each of the tumor cell nuclei may be annotated (e.g., using a simple point), after which each nucleus is segmented, as shown in FIG. 12B. As shown in the callout in FIG. 12B, different nuclei may show different nuclear morphological features. For example, the boundary of nucleus 1210 is relatively round as compared to the egg-shaped boundary of nucleus 1220 or the irregular, partially curved, partially angular boundaries of nuclei 1230 and 1240. In addition, the relative area of nucleus 1220 appears to be approximately double that of nucleus 1210 and approximately triple the area of nucleus 1230. Next, as shown in FIG. 12C, a mask may be generated for each nucleus in order to define the bounds within each nuclear morphology feature is measured.

In some embodiments, identifying tumor heterogeneity by assessing nuclear heterogeneity. In some embodiments, assessing nuclear heterogeneity comprises quantifying certain features of cell nuclei to distinguish mutated cells based on nuclear morphologic heterogeneity. In some embodiments, the digital pathology image processing system 210 may analyze each tumor nucleus identified in the WSI using any of several different approaches. For example, in one approach, automatic tumor nuclei detection and parameterization may be performed, in which a trained machine-learning model may be used to identify each tumor nucleus, measure a set of specified parameters or features for each nucleus, as discussed below, and then compare the population-level distribution of these specified parameters or features. In another example, the approach may comprise performing tumor image segmentation, which may be an image patch-based assessment. In some instances, determination of tumor heterogeneity may be performed on a slide prediction basis (which may include, for example, calculating percentage(s) of image patches predicted to be heterogeneous, or averages of each slide's prediction scores).

In some instances, tumor heterogeneity may be driven by the type of gene involved in a gene fusion. For tumor suppressor genes, oncogenesis may be mediated by loss of function. Such mutations release the cell from cell cycle control which in turn may indirectly promote growth. Over time, this process allows for the accumulation of cancer-promoting mutations with each new generation of daughter cells. In contrast, for oncogenes, oncogenesis may be mediated by gain of function. Over-activation of growth factors, for example, may directly promote growth, thereby resulting in unrestricted growth. This process is predicted to result in an immediate growth advantage that does not require additional mutations. Based on this rationale, low tumor heterogeneity may be expected in tumors comprising a fusion involving an oncogene, such as ALK, ROS1, RET and NTRK.

One approach to assessing tumor heterogeneity may include assessment of the morphology of cellular-level structures in tumor cells, such as nuclei. The morphology of nuclei may be represented by a plurality of image features, which may be organized into categories of image features, such as, by way of example and not limitation, chromatin features, geometric coordinates, basic morphology features, two-dimensional shape features, first-order statistics, "gray-level" (e.g., where "gray" represents a spatial distribution of pixel intensity levels) co-occurrence matrix features, gray-level dependence matrix features, gray-level run length matrix features, gray-level size zone matrix features, neighboring gray-tone difference matrix features, advanced nucleus morphology features, and boundary and curvature features.

Each type may comprise one or more image features. Example image features may include, but are not limited to:
chromatin features, such as:
    heterogeneity of the nucleus (hetero),
    the size distribution of granules (clump),
    the fraction of large granules with respect to total nuclear area (condense),
    the distribution around the nuclear membrane or margin (margination);
geometric coordinates, such as:
    the region coordinates (region_coords),
    the x coordinates (x),
    the y coordinates (y);
basic morphology features, such as:
    area of the nucleus (area),
    convex area of the nucleus (convex_area),
    eccentricity of the nucleus (eccentricity),
    diameter of the nucleus (equivalent_diameter),
    the ratio of pixels in the nucleus to pixels in a bounding box, either in a total field or view or a selected area of a field of view (extent),
    perimeter of the nucleus (perimeter),
    the ratio of pixels in the nucleus to pixels of a convex hull (solidity),
    the elongation of the nucleus as measured by eigenvalues of the inertia tensor (inertia_tensor_eigvals1, inertia_tensor_eigvals2),
    the length of the major axis of the nucleus (major_axis_length),
    the length of the minor axis of the nucleus (minor_axis_length),
    Hu moments (a certain particular weighted average, a.k.a. "moment," of the image pixels' intensities, i.e., translation, rotation, and scale-invariant moments) (moments_hu0, moments_hu1, moments_hu2, moments_hu3, moments_hu4, moments_hu5, moments_hu6),
    weighted Hu moments (weighted_moments_hu0, weighted_moments_hu1, weighted_moments_hu2, weighted_moments_hu3, weighted_moments_hu4, weighted_moments_hu5, weighted_moments_hu6);
two-dimensional shape features, such as:
    two-dimensional shape elongation (original_shape2D_Elongation),
    two-dimensional shape maximum diameter (original_shape2D_MaximumDiameter), two-dimensional shape mesh surface (original_shape2D_MeshSurface),
    two-dimensional shape perimeter-to-surface ratio (original_shape2D_PerimeterSurfaceRatio),
    two-dimensional shape pixel surface (original_shape2D_PixelSurface),
    two-dimensional shape sphericity (original_shape2D_Sphericity),
    two-dimensional shape spherical disproportion (original_shape2D_SphericalDisproportion);
first-order statistics, such as:
    first-order $10^{th}$ percentile (original_firstorder_10Percentile),
    first-order $90^{th}$ percentile (original_firstorder_90Percentile),
    first-order energy (original_firstorder_Energy),
    first-order entropy, which specifies the uncertainty or randomness in the image values (original_firstorder_Entropy),
    first-order interquartile range, which measures the variability based on quartile splitting (original_firstorder_InterquartileRange),
    first-order kurtosis, which measures the "peakedness" of the distribution of values (original_firstorder_Kurtosis),
    first-order maximum (original_firstorder_Maximum),
    first-order mean absolute deviation (original_firstorder_MeanAbsoluteDeviation),
    first-order mean (original_firstorder_Mean),
    first-order median (original_firstorder_Median),
    first-order minimum (original_firstorder_Minimum),
    first-order range (original_firstorder_Range),
    first-order robust man absolute deviation, which is the mean distance of all intensity values from the mean value (original_firstorder_RobustMeanAbsoluteDeviation),
    first-order root mean squared, which is the mean of all squared intensity values (original_firstorder_RootMeanSquared),
    first-order skewness, which measures the asymmetry of the distribution of values about the mean (original_firstorder_Skewness),
    first-order total energy (original_firstorder_TotalEnergy),
    first-order uniformity (original_firstorder_Uniformity),
    first-order variance (original_firstorder_Variance);
gray-level co-occurrence matrix (GLCM) (describes the second-order joint probability function of an image region constrained by the mask) features, such as
    GLCM autocorrelation (original_glcm_Autocorrelation),
    GLCM cluster prominence (original_glcm_ClusterProminence),
    GLCM cluster shade (original_glcm_ClusterShade),
    GLCM cluster tendency (original_glcm_ClusterTendency),
    GLCM contrast (original_glcm_Contrast),
    GLCM correlation (original_glcm_Correlation),
    GLCM difference average (original_glcm_DifferenceAverage),
    GLCM difference entropy (original_glcm_DifferenceEntropy)
    GLCM difference variance (original_glcm_DifferenceVariance),
    GLCM inverse difference (original_glcm_Id),
    GLCM inverse difference moment (original_glcm_Idm), GLCM inverse difference moment normalized (original_glcm_Idmn), GLCM inverse difference normalized (original_glcm_Idn), GLCM informational measure of correlation (original_glcm_Imc1, original_glcm_Imc2), GLCM inverse variance (original_glcm_Inverse Variance), GLCM joint average (original_glcm_JointAverage), GLCM joint energy (original_glcm_JointEnergy), GLCM joint entropy (original_glcm_JointEntropy), GLCM maximal correlation coefficient (original_glcm_MCC), GLCM maximum probability (original_glcm_MaximumProbability), GLCM sum average (original_glcm_SumAverage), GLCM sum entropy (original_glcm_SumEntropy), GLCM sum squares (original_glcm_SumSquares);

gray-level dependence matrix (quantifies gray level dependencies in an image, wherein a gray level dependency is defined as the number of connected pixels within a specified distance that are dependent on the center pixel) features, such as:

GLDM gray level dependence entropy (original_gldm_DependenceEntropy),

GLDM dependence nonuniformity (original_gldm_DependenceNonUniformity),

GLDM dependence nonuniformity normalized (original_gldm_DependenceNonUniformityNormalized), GLDM dependence variance (original_gldm_DependenceVariance), GLDM gray-level nonuniformity (original_gldm_GrayLevelNonUniformity), GLDM gray-level variance (original_gldm_GrayLevelVariance), GLDM high gray-level emphasis (original_gldm_HighGrayLevelEmphasis), GLDM large dependence emphasis (original_gldm_LargeDependenceEmphasis), GLDM large dependence high gray-level emphasis (original_gldm_LargeDependenceHighGrayLevelEmphasis), GLDM large dependence low gray-level emphasis (original_gldm_LargeDependenceLowGrayLevelEmphasis), GLDM low gray-level emphasis (original_gldm_LowGrayLevelEmphasis), GLDM small dependence emphasis (original_gldm_SmallDependenceEmphasis), GLDM small dependence high gray-level emphasis (original_gldm_SmallDependenceHighGrayLevelEmphasis), GLDM small dependence low gray-level emphasis (original_gldm_SmallDependenceLowGrayLevelEmphasis);

gray-level run length matrix (GLRLM) (quantifies gray level runs, which are defined as the length in number of pixels, of consecutive pixels that have the same gray level value) features, such as:

GLRLM gray-level nonuniformity (original_glrlm_GrayLevelNonUniformity),

GLRLM gray-level nonuniformity normalized (original_glrlm_GrayLevelNonUniformityNormalized), GLRLM gray-level variance (original_glrim_GrayLevelVariance), GLRLM high gray-level run emphasis (original_glrlm_HighGrayLevelRunEmphasis), GLRLM long-run emphasis (LRE) (original_glrlm_LongRunEmphasis), GLRLM long-run high gray-level emphasis (original_glrlm_LongRunHighGrayLevelEmphasis), GLRLM long-run low gray-level emphasis (original_glrm_LongRunLowGrayLevelEmphasis), GLRLM low gray-level run emphasis (original_glrlm_LowGrayLevelRunEmphasis), GLRM run entropy (original_glrm_RunEntropy), GLRM run length nonuniformity), (original_glrm_RunLengthNonuniformity), GLRLM run length nonuniformity normalized (original_glrlm_RunLengthNonUniformityNormalized), GLRLM run percentage (original_glrlm_RunPercentage), GLRLM run variance (original_glrlm_RunVariance), GLRLM short run emphasis (original_glrlm_ShortRunEmphasis), GLRLM short run high gray-level emphasis (original_glrlm_ShortRunHighGrayLevelEmphasis), GLRLM short run low gray-level emphasis (original_glrlm_ShortRunLowGrayLevelEmphasis);

gray-level size zone (GLSZM) (describes gray-level zones in an image region) matrix features, such as:

GLSZM gray-level nonuniformity (original_glszm_GrayLevelNonUniformity),

GLSZM gray-level nonuniformity normalized (original_glszm_GrayLevelNonUniformityNormalized), GLSZM gray-level variance (original_glszm_GrayLevelVariance), GLSZM high gray-level zone emphasis (original_glszm_HighGrayLevelZoneEmphasis), GLSZM large area emphasis (original_glszm_LargeAreaEmphasis), GLSZM large area high gray-level emphasis (original_glszm_LargeAreaHighGrayLevelEmphasis), GLSZM large area low gray-level emphasis (original_glszm_LargeAreaLowGrayLevelEmphasis), GLSZM low gray-level zone emphasis (original_glszm_LowGrayLevelZoneEmphasis), GLSZM size zone nonuniformity (original_glszm_SizeZoneNonUniformity), GLSZM size zone nonuniformity normalized (original_glszm_SizeZoneNonUniformityNormalized), GLSZM small area emphasis (original_glszm_SmallAreaEmphasis), GLSZM small area emphasis high gray-level emphasis (original_glszm_SmallAreaHighGrayLevelEmphasis), GLSZM small area low gray-level emphasis (original_glszm_SmallAreaLowGrayLevelEmphasis), GLSZM zone entropy (original_glszm_ZoneEntropy), GLSZM zone percentage (original_glszm_ZonePercentage), GLSZM zone variance (original_glszm_ZoneVariance);

neighboring gray-tone difference matrix (NGTDM) (describes the difference between a gray value and the average gray value of neighbors within a certain distance) features, such as:

NGTDM busyness (original_ngtdm_Busyness),

NGTDM coarseness (original_ngtdm_Coarseness),

NGTDM complexity (original_ngtdm_Complexity),

NGTDM contrast (original_ngtdm_Contrast),

NGTDM strength (original_ngtdm_Strength);

advanced nucleus morphology features, such as:

radius of an ellipse-shaped nucleus (ellipse_R_index), major axis of an ellipse-shaped nucleus (ellipse_MA_index), convexity perimeter of a nucleus, which measures the perimeter of curvature (convexity_perimeter), circularity of a nucleus, which measures the roundness of a nucleus (circularity), normalized number of connected components that remain when a shape is subtracted from a convex hull (Ncce_index);

boundary (where a boundary signature of a nucleus is the distance profile from all boundary coordinates to the centroid points of the nucleus) features, such as:

mean (mean(R)($\equiv$ <R>)), median (median(R)), mode (mode(R)), maximum (max_v: maxR(R)), minimum (min_v: min(R)), $25^{th}$ percentile of a boundary signature (percentile_25: 25% percentile (R)), $75^{th}$ percentile of a boundary signature (percentile_75: 75% percentile (R)), below $25^{th}$ percentile of mean boundary signature (mean_below_percentile_25: mean (R(R<percentile_25))), above $75^{th}$ percentile of mean boundary signature (mean_above_percentile_75: mean (R(R>percentile_75))), sum distance of a boundary signature (sum_dist: sum (R)), harmonic mean of a boundary signature (harmonic_mean: harmonic mean(R)), 3% trimmed mean boundary signature (trimmed_mean_3_percent: 3% trimmed mean(R)), 5% trimmed mean boundary signature (trimmed_mean_5_percent: 5% trimmed mean(R)), 15% trimmed mean boundary signature (trimmed_mean_15_percent: 15% trimmed mean (R)), 25% trimmed mean boundary signature (trimmed_mean_25_percent: 25% trimmed mean (R)), standard deviation (std_dev: standard deviation (R)($\equiv$ sR)), standard deviation by mean (std_dev_by_mean: sR/|<R>|), standard deviation by median (std_dev_by_median: sR/|median(R)|), standard deviation by mode (std_dev_by_mode: sR/|mode(R)|), skewness (skewness(R)), kurtosis (kurtosis(R)), mean distance profile minus mean of a boundary signature (mean_dist_profile_minus_mean: mean (|R−<R>|)), range (range_v: range(X)), interquartile range (interquartile_range: interquartile range (X)), sum distance profile squared (sum_dist_profile_square: sum(R2)), sum distance profile cubed (sum_dist_profile_cube: sum(R3)), mean distance profile squared (mean_dist_profile_square: mean(R2)), mean distance profile cubed (mean_dist_profile_cube: mean(R3)), mean distance profile raised to four (mean_dist_profile_raise_to_four: mean(R4)), mean distance profile raised to five (mean_dist_profile_raise_to_five: mean(R5)), sum distance profile minus mean power of 2 (sum_dist_profile_minus_mean_pow2: sum(|R−<R>|2)), sum distance profile minus mean power of 3 (sum_dist_profile_minus_mean_pow3: sum(|R−<R>|3)), mean distance profile minus mean power of 2 (mean_dist_profile_minus_mean_pow2: mean(|R−<R>|2)), mean distance profile minus mean power of 3 (mean_dist_profile_minus_mean_pow3: mean(|R−<R>|3)), mean distance profile minus mean power of 4 (mean_dist_profile_minus_mean_pow4: mean(|R−<R>|4)), mean distance profile minus mean power of 5 (mean_dist_profile_minus_mean_pow5: mean(|R−<R>|5)), number of peaks (number_of_peaks), gini coefficient (gini coefficient);

curvature features, such as:

mean curvature (c_mean: mean(k) ($\equiv$ <k>)), median curvature (c_median: median(k)), mode curvature (c_mode: mode(k)), maximum curvature (c_max_v: max(k)), minimum curvature (c_min_v: min(k)), $25^{th}$ percentile curvature (c_percentile_25: 25% percentile (k)), $75^{th}$ percentile curvature (c_percentile_75: 75% percentile (k)), below $25^{th}$ percentile of the mean curvature (c_mean_below_percentile_25: mean(k (k<c_percentile_25))), above $75^{th}$ percentile of the mean curvature (c_mean_above_percentile_75: mean (k(k>c_percentile_75))), sum dance (c_sum_dist: sum(k)), harmonic mean (c_harmonic_mean: harmonic mean (k)), 3% trimmed mean curvature (c_trimmed_mean_3_percent: 3% trimmed mean (k)), 3% trimmed mean curvature (c_trimmed_mean_5_percent: 5% trimmed mean (k)), 15% trimmed mean curvature (c_trimmed_mean_15_percent: 15% trimmed mean (k)), 25% trimmed mean curvature (c_trimmed_mean_25_percent: 25% trimmed mean (k)), standard deviation (c_std_dev: standard deviation(k) ($\equiv$ sk)), standard deviation by mean (c_std_dev_by_mean: sk/|<k>|), standard deviation by median (c_std_dev_by_median: sk/|median(k)|), standard deviation by mode (c_std_dev_by_mode: sk/|mode(k)|), skewness (c_skewness: skewness(k)), kurtosis (c_kurtosis: kurtosis(k)), mean curvature (c_mean: mean(|k−<k>|)), range of curvature (c_range_v: range(k)), interquartile range (c_interquartile_range: interquartile range (k)), sum curvature profile squared (c_sum_curvature_profile_square: sum(k2), sum curvature profile cubed (c_sum_curvature_profile_cube: sum(k3)), mean curvature profile squared (c_mean_curvature_profile_square: mean(k2)), mean curvature profile cubed (c_mean_curvature_profile_cube: mean(k3)), mean curvature profile raised to four (c_mean_curvature_profile_raise_to_four: mean(k4)), mean curvature profile raised to five (c_mean_curvature_profile_raise_to_five: mean(k5)), sum curvature profile minus mean power of 2 (c_sum_curvature_profile_minus_mean_pow2: sum(|k–<k>|2)), sum curvature profile minus mean power of 3 (c_sum_curvature_profile_minus_mean_pow3: sum(|k–<k>|3)), mean curvature profile minus mean power of 2 (c_mean_curvature_profile_minus_mean_pow2: mean(|k–<k>|2)), mean curvature profile minus mean power of 3 (c_mean_curvature_profile_minus_mean_pow3: mean(|k–<k>|3)), mean curvature profile minus mean power of 4 (c_mean_curvature_profile_minus_mean_pow4: mean(|k–<k>|4)), mean curvature profile minus mean power of 5 (c_mean_curvature_profile_minus_mean_pow5: mean(|k–<k>|5)), number of peaks (c_number_of_peaks: number of peaks), gini coefficient (c_gini_coefficient: gini coefficient (k)).

The image features may be evaluated using one or more statistical metrics. One or more feature selection processes may be used to select image features that are associated with oncogenic drivers. Non-limiting example statistical metrics are standard deviation, quadratic entropy which averages the difference between two randomly-drawn samples, Kolmogorov-Smirnov which is based on the distance between the normal distribution and the empirical distribution function of a sample, and outlier percentage (e.g., percentage of values outside the range of twice the standard deviation from the mean). In some embodiments, the selected images features may have the highest relevance to oncogenic drivers amongst the plurality of image features. The oncogenic drivers may be fusion, mutation, or unknown drivers.

In some embodiments, example selected nuclear morphology image features may be comprised in four example categories. A category of shape-related features may include features targeting the geometric shape of the cell nuclei. Captured properties may include, by way of example and not limitation, the size and shape of the individual cell nuclei as well as its image moments (weighted average of image pixel intensities). Example selected features in this category may include:

area of the nucleus (area), the ratio of pixels in the nucleus to pixels in a bounding box, either in a total field or view or a selected area of a field of view (extent), the ratio of pixels in the nucleus to pixels of a convex hull (solidity), Hu moments (a certain particular weighted average, a.k.a. "moment," of the image pixels' intensities, i.e., translation, rotation, and scale-invariant moments) (moments_hu0), weighted Hu moments (weighted_moments_hu0, weighted_moments_hu1, weighted_moments_hu2);

two-dimensional shape features, such as the two-dimensional shape perimeter-to-surface ratio (original_shape2D_PerimeterSurfaceRatio);

radius of an ellipse-shaped nucleus (ellipse_R_index), major axis of an ellipse-shaped nucleus (ellipse_MA_index)

convexity perimeter of a nucleus, which measures the perimeter of curvature (convexity_perimeter), and normalized number of connected components that remain when a shape is subtracted from a convex hull (Nc-ce_index).

A category of intensity distribution-related features may include features capturing the statistical properties of the distribution of image intensities (pixel values) in the images of the individual cell nuclei. Example selected features in this category may include:

first-order $90^{th}$ percentile (original_firstorder_90Percentile), first-order minimum (original_firstorder_Minimum), and first-order entropy, which specifies the uncertainty or randomness in the image values (original_firstorder_Entropy).

A category of texture-related features may include features targeting the quantification of texture by analyzing spatial relationships among pixels and their values (in sub-regions) of the cell nuclei images. As noted below, gray-level co-occurrence matrix (GLCM) describes the second-order joint probability function of an image region constrained by the mask. Gray-level dependence matrix (GLDM) quantifies gray level dependencies in an image, wherein a gray level dependency is defined as the number of connected pixels within a specified distance that are dependent on the center pixel. Gray-level run length matrix (GLRLM) quantifies gray level runs, which are defined as the length in number of pixels, of consecutive pixels that have the same gray level value. Example selected features in this category may include:

GLCM inverse difference (original_glcm_Id),

GLCM contrast (original_glcm_contrast),

GLCM joint entropy (original_glcm_JointEntropy),

GLCM sum entropy (original_glcm_SumEntropy);

GLDM gray level dependence entropy (original_gldm_DependenceEntropy),

GLDM dependence non uniformity normalized (DNUN) which measures the similarity of dependence through the image and is normalized (original_DependenceNonUniformityNormalized), small dependence emphasis (SDE) which measures the distribution of small dependencies (original_gldm_SmallDependenceEmphasis);

GLRLM long-run emphasis (LRE) (original_glrlm_LongRunEmphasis),

GLRLM long-run low gray-level emphasis (original_glrm_LongRunLowGrayLevelEmphasis), GLRM run length nonuniformity (original_glrm_RunLengthNonuniformity), GLRM run entropy (original_glrm_RunEntropy);

A category of boundary curvature-related features may include features derived from the analysis of the curvature of the boundary of the cell nuclei with different statistical methods. Example selected features in this category may include:

mean curvature (c_mean), median curvature (c_median), $25^{th}$ percentile curvature (c_percentile_25), $75^{th}$ percentile curvature (c_percentile_75), above $75^{th}$ percentile of the mean curvature (c_mean_above_percentile_75), 3% trimmed mean curvature (c_trimmed_mean_3_percent), 5% trimmed mean curvature (c_trimmed_mean_5_percent), 15% trimmed mean curvature (c_trimmed_mean_15_percent), 25% trimmed mean curvature (c_trimmed_mean_25_percent), interquartile range curvature (c_interquartile_range), and gini coefficient of a curvature (c_gini_coefficient).

FIGS. 13A-13E illustrate non-limiting examples of experimental results of identification of gene fusions based on quantifying certain nuclear morphology features. As shown in FIGS. 13A-13E, comparison of these specific nuclear morphology features may provide a statistically significant distinction between gene fusions, oncogene driver mutations, and tumor suppressors and/or unknown drivers.

Figure 14A:
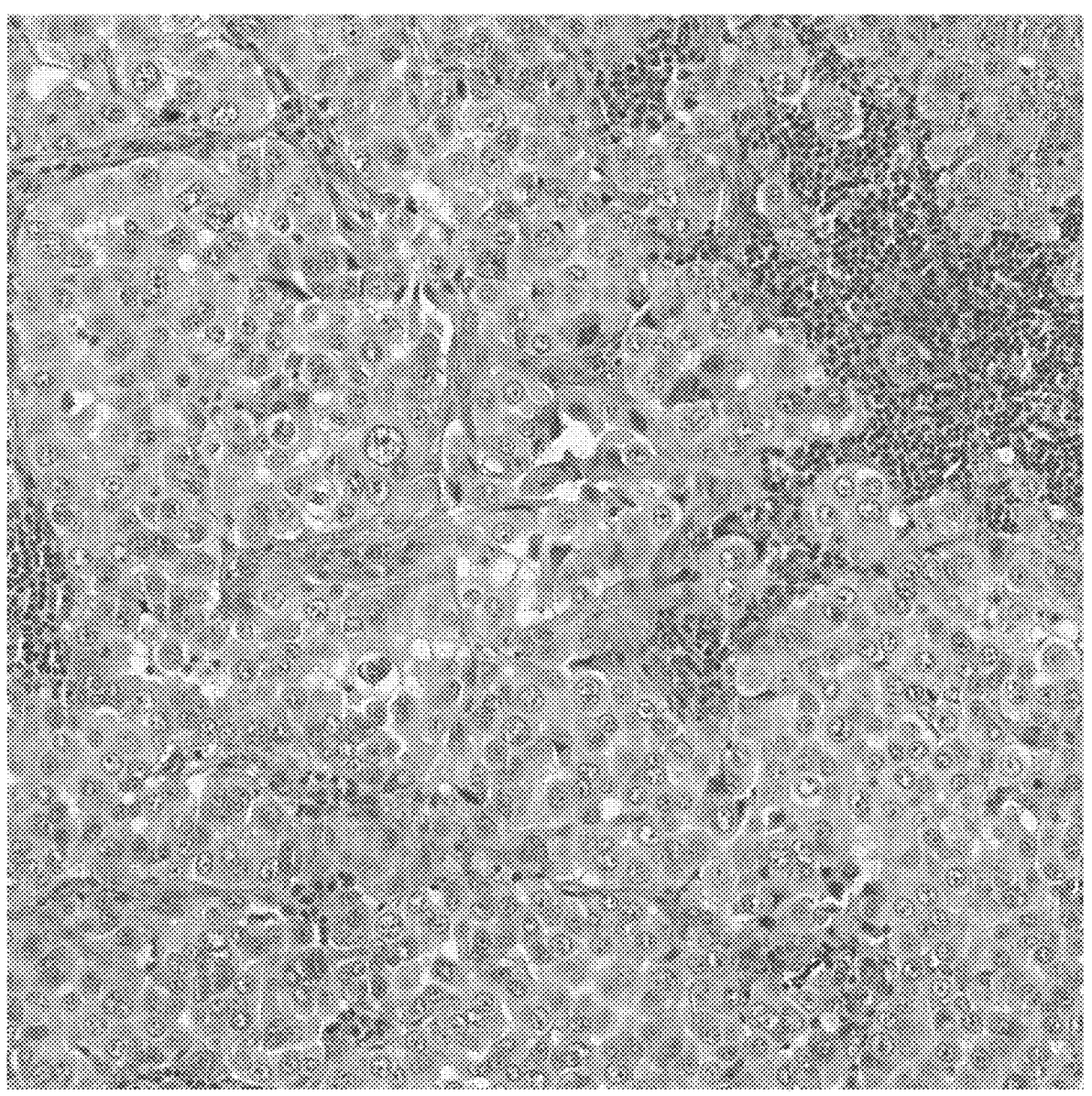
FIGS. 14A-14C illustrate non-limiting examples of digital pathology images illustrating four different nuclear morphology features corresponding to a tumor suppressor and/or unknown driver.
Figure 14B:
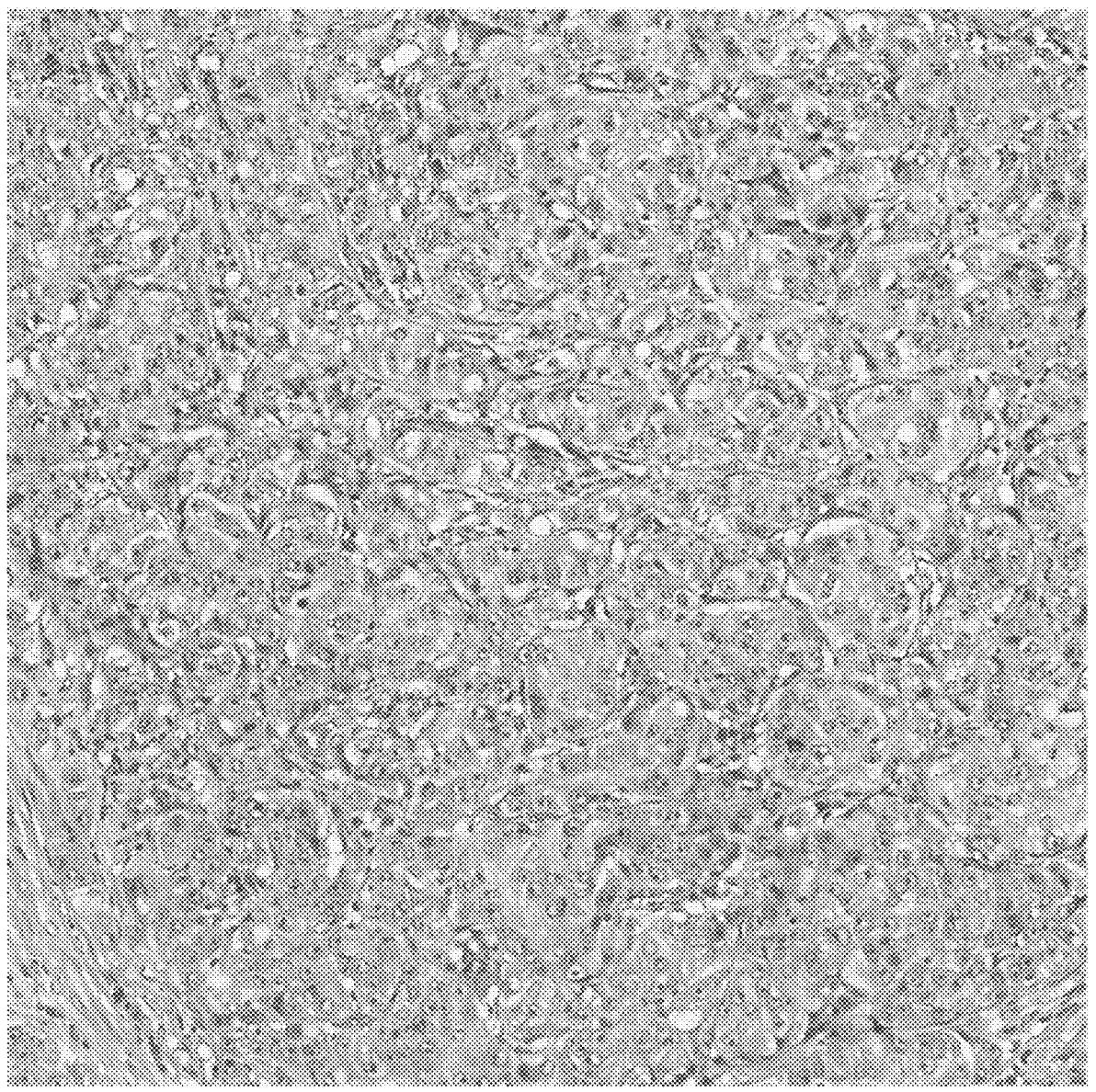
Figure 14C:
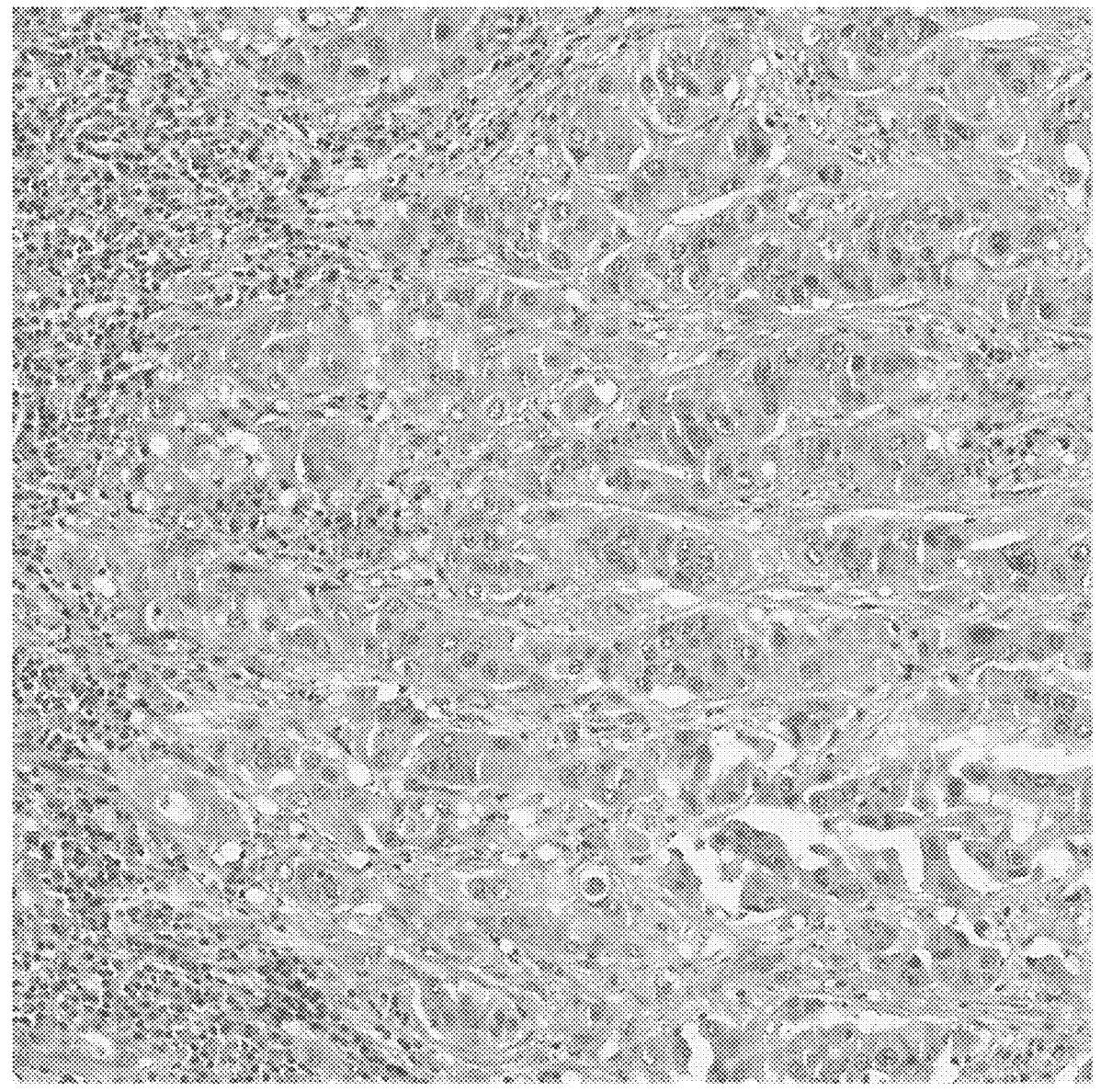

FIGS. 14A-14C illustrate non-limiting examples of digital pathology images illustrating four different nuclear morphology features corresponding to a tumor suppressor and/or unknown driver. FIGS. 14A-14C illustrate an example WSI for which the nuclear morphology features of "Area," "First Order Entropy," and "RunLengthNonUniformity," respectively, are highly indicative of the degree of tumor heterogeneity possibly present in the mutational context of a tumor suppressor and/or unknown driver. "Area" may be the surface area of the observed cell nuclei. "First Order Entropy" may be the first-order statistics describing the distribution of pixel intensities (i.e., values) within the considered image region. Thereby entropy specifies the uncertainty/randomness in the observed pixel values. "RunLengthNonUniformity" may be the run-length metrics quantifying gray-level runs in an image. A gray-level run is defined as the length in number of pixels, of consecutive pixels that have the same gray level value. In a gray-level-run length matrix p(i,j|θ), the (i,j)th element describes the number of times j a gray level i appears consecutively in the direction specified by θ. The RunLengthNonUniformity measure analyzes the distribution of the possible runs with given run lengths based on this gray-level-run-length matrix.

Figure 15A:
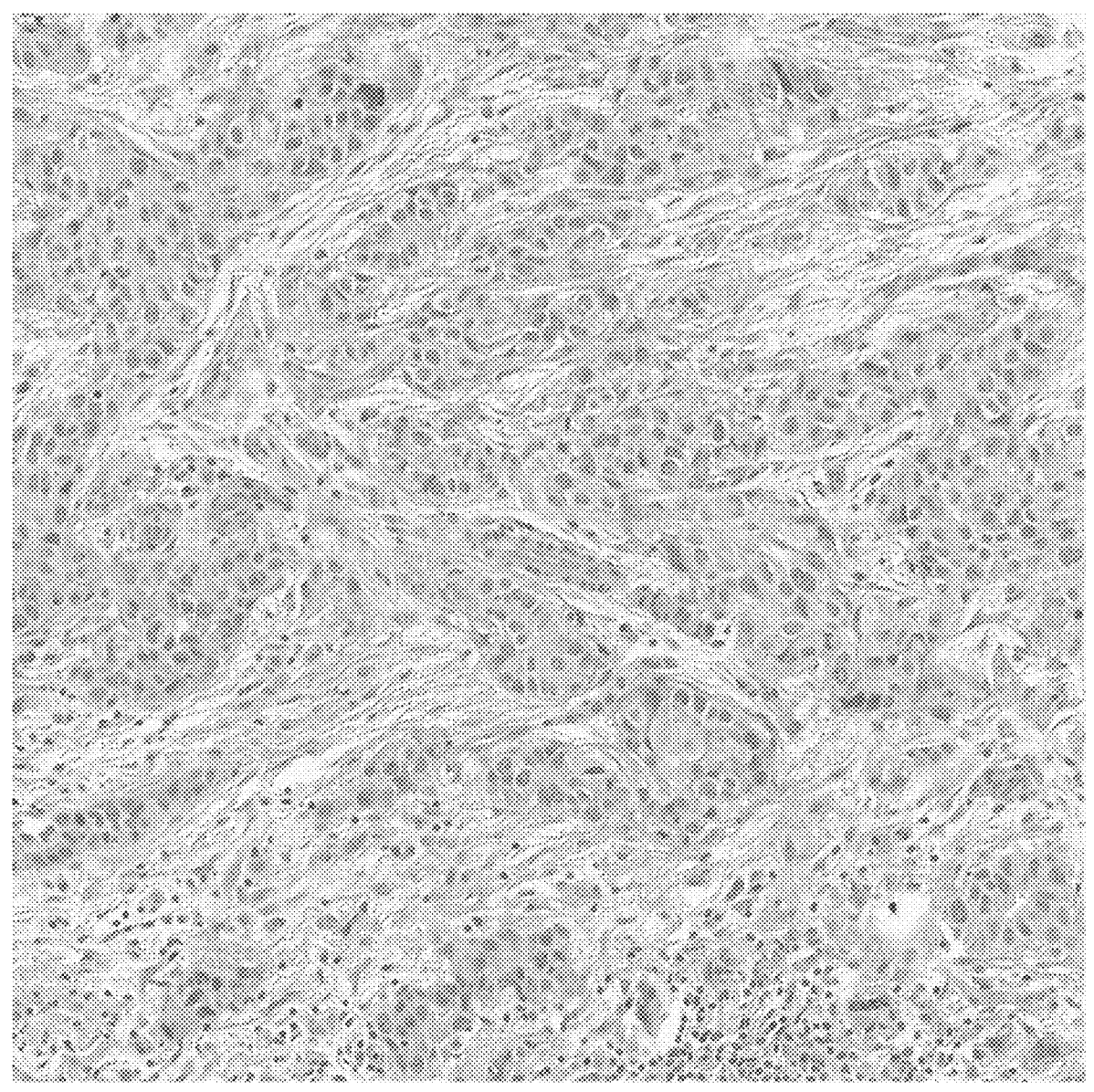
FIGS. 15A-15C illustrate non-limiting examples of digital pathology images illustrating four different nuclear morphology features corresponding to an oncogene driver mutation.
Figure 15B:
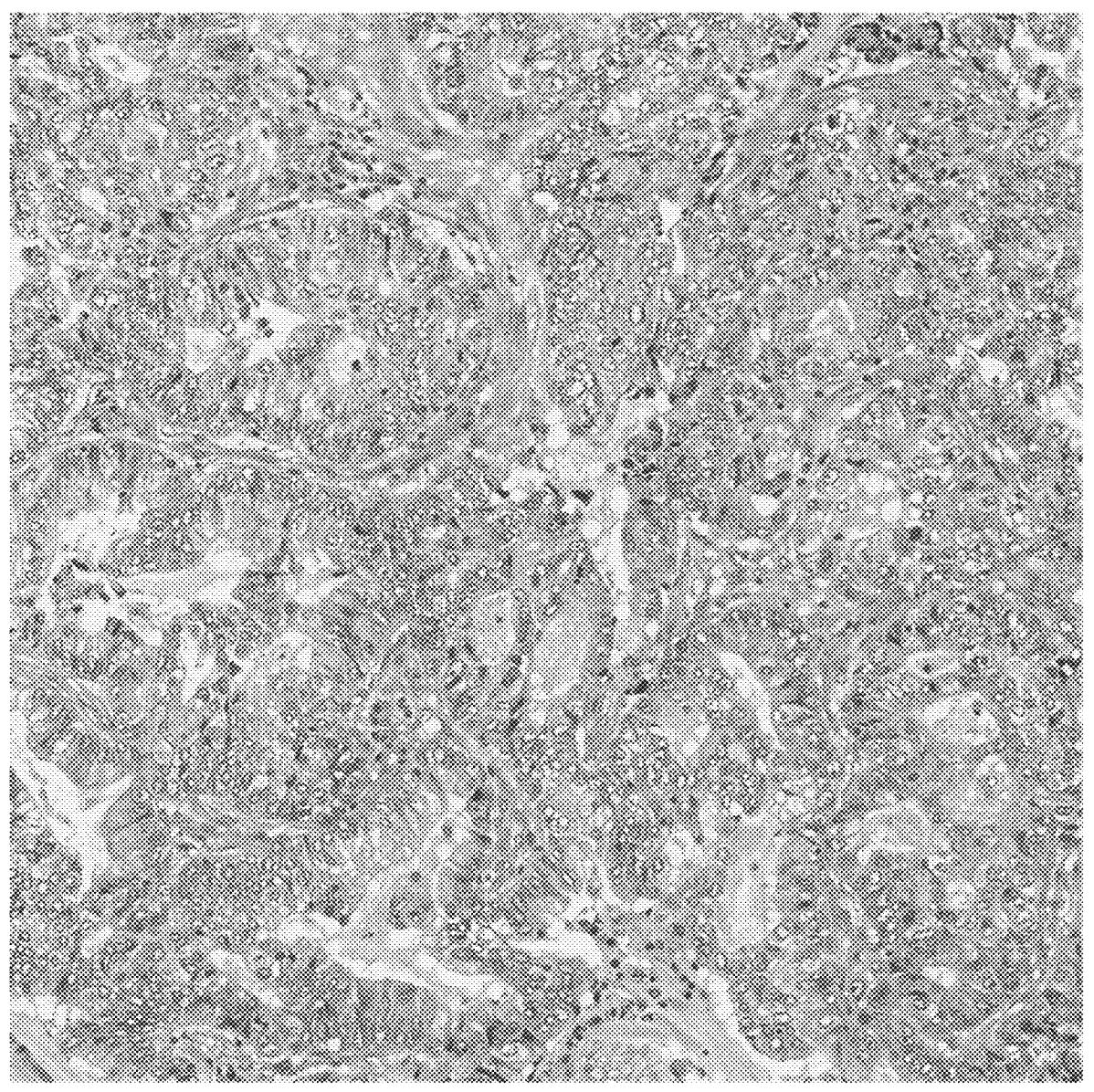
Figure 15C:
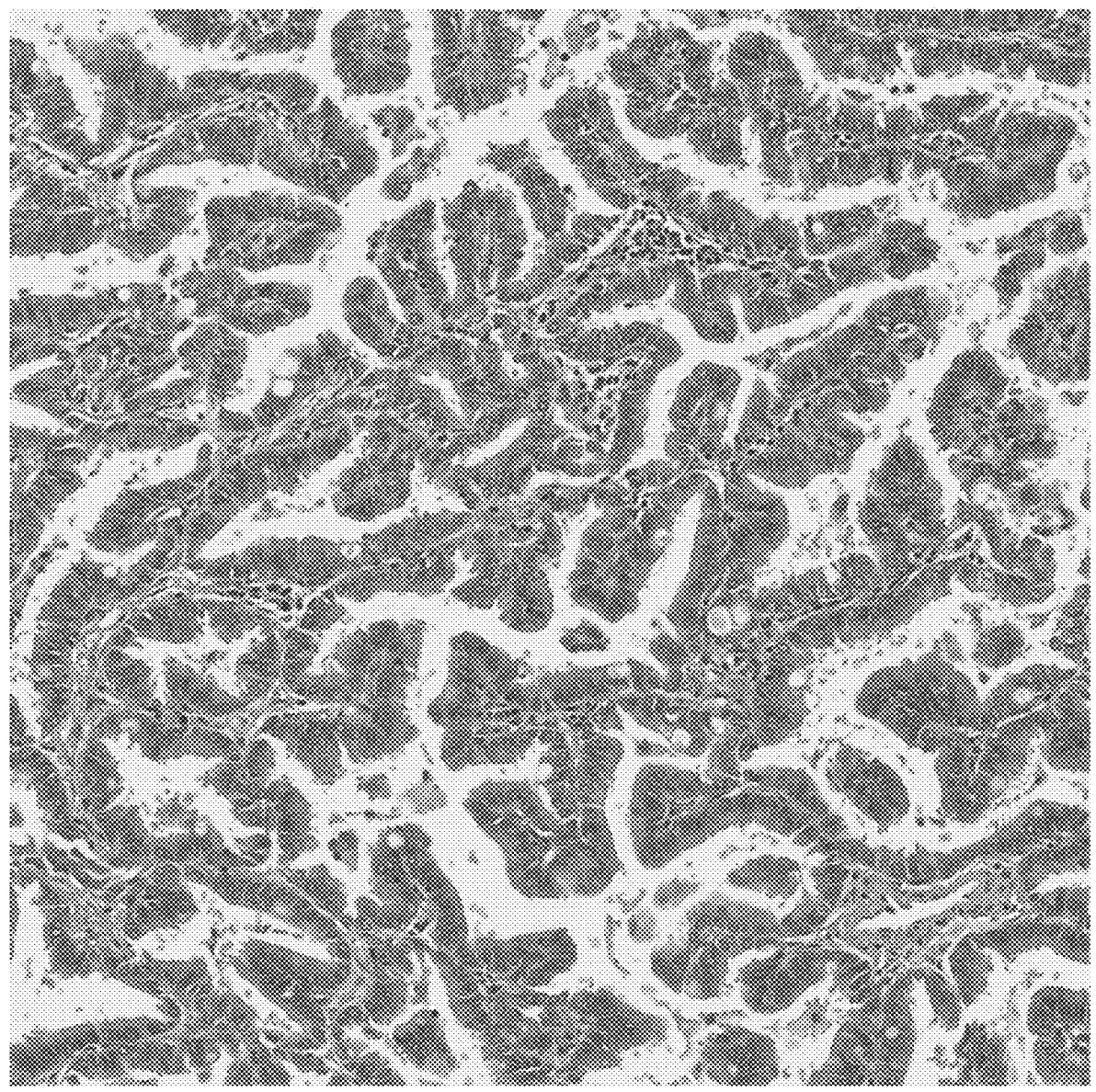

FIGS. 15A-15C illustrate non-limiting examples of digital pathology images illustrating four different nuclear morphology features corresponding to an oncogene driver mutation. FIGS. 15A-15C illustrate an example WSI for which the nuclear morphology features of "Area," "First Order Entropy," and "RunLengthNonUniformity," respectively, are highly indicative of the degree of tumor heterogeneity possibly present in the mutational context of an oncogene driver mutation.

Figure 16A:
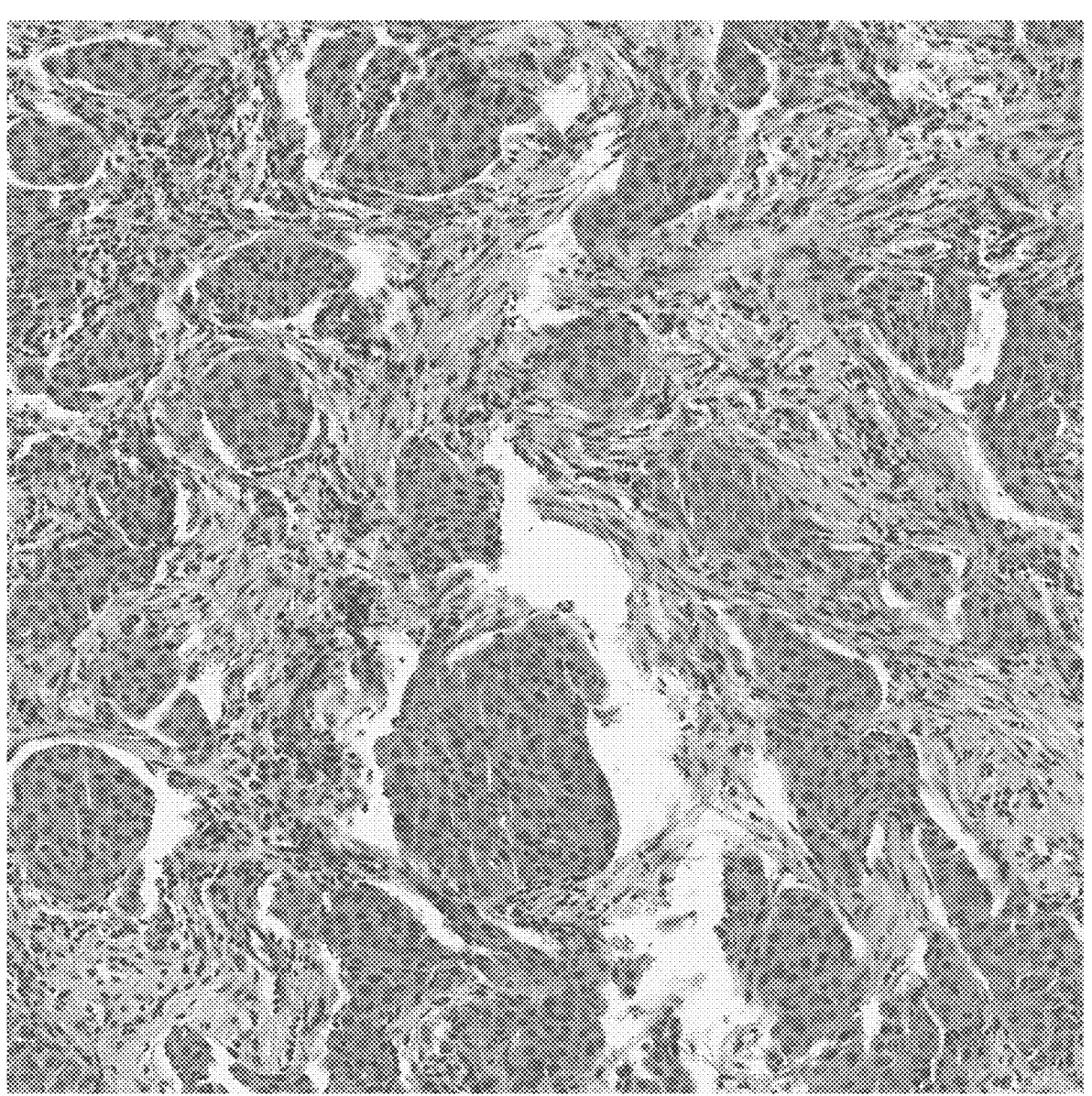
FIGS. 16A-16C illustrate non-limiting examples of digital pathology images illustrating four different nuclear morphology features corresponding to a gene fusion.
Figure 16B:
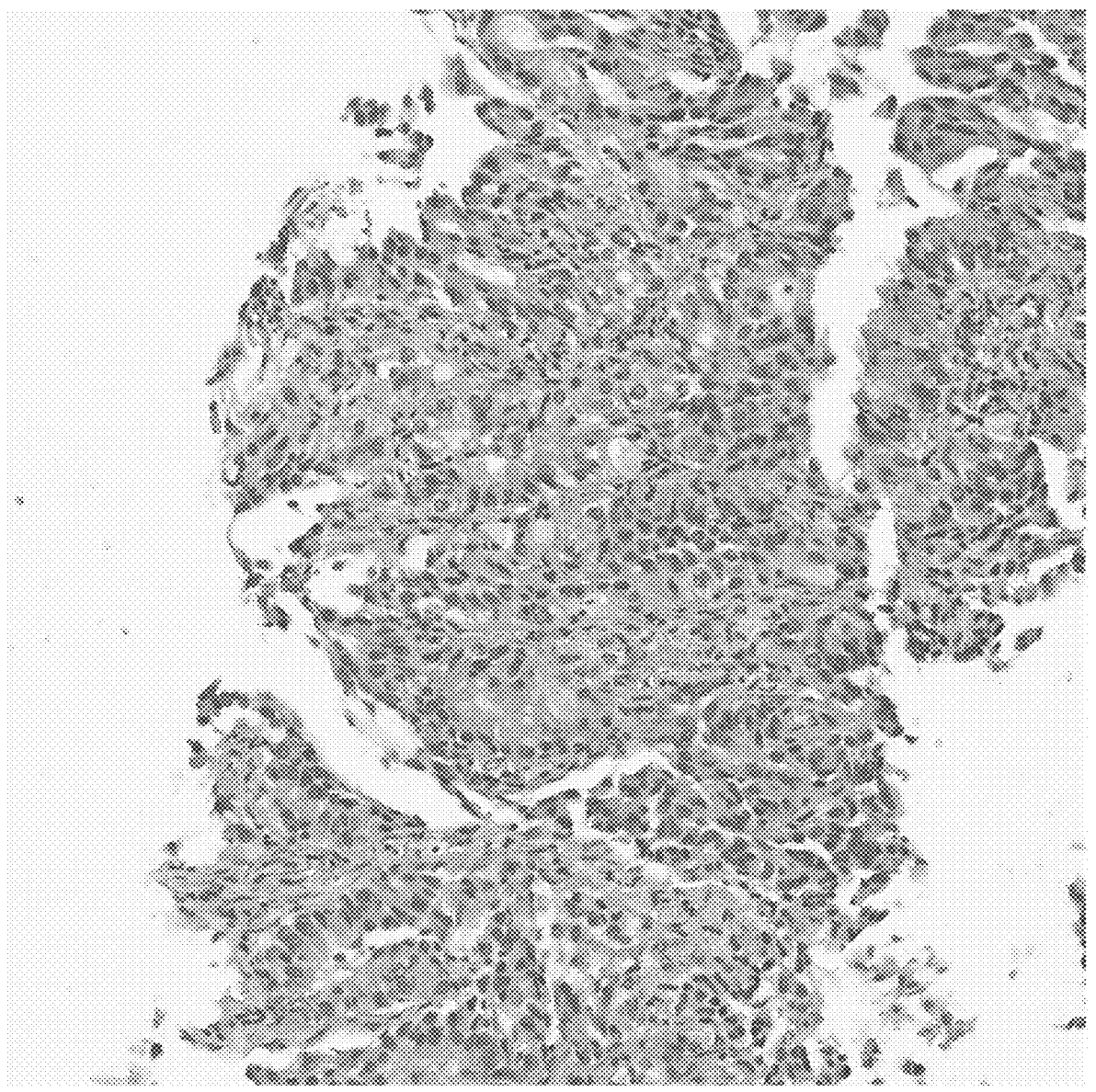
Figure 16C:
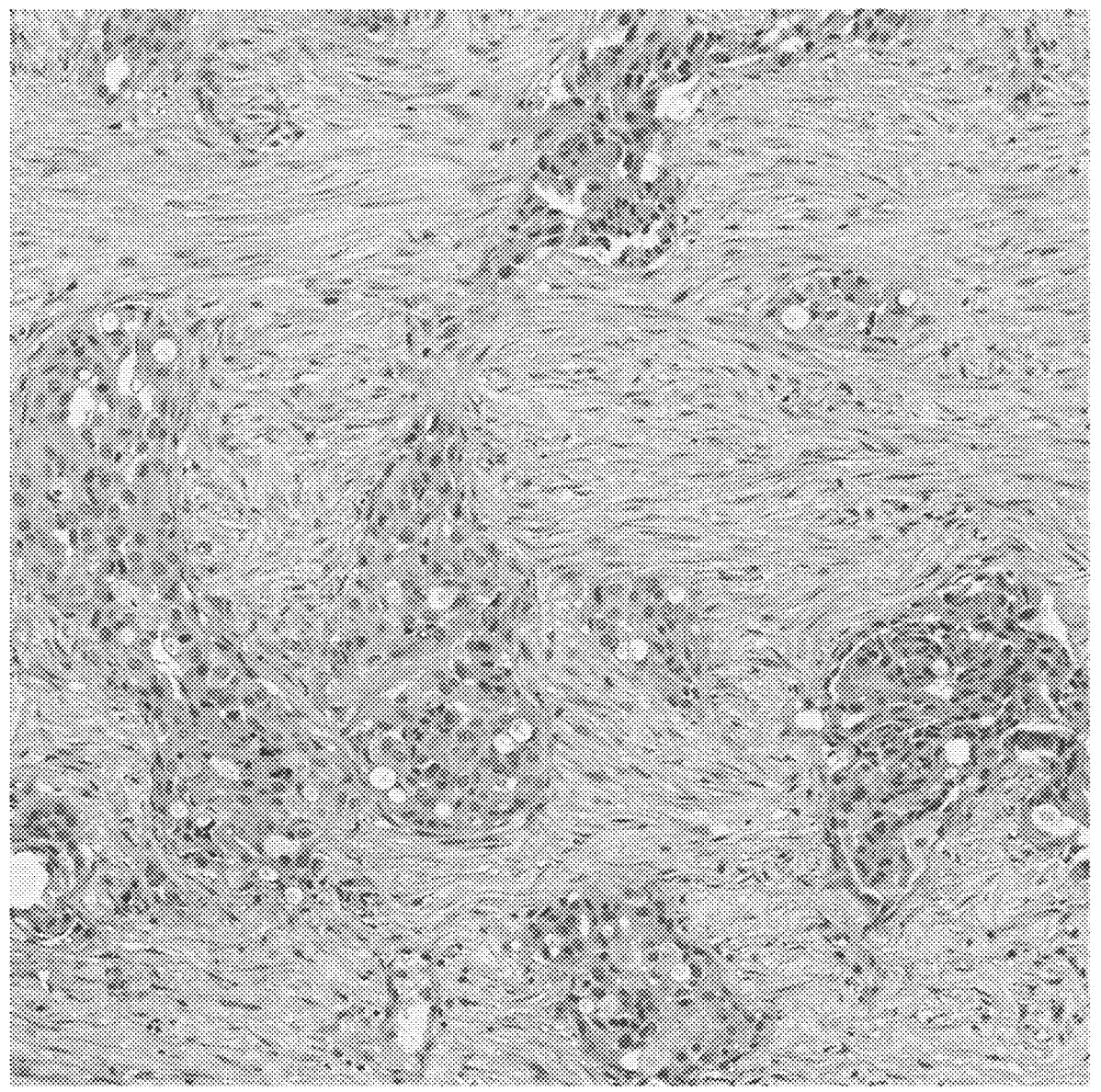

FIGS. 16A-16C illustrate non-limiting examples of digital pathology images illustrating four different nuclear morphology features corresponding to a gene fusion. FIGS. 16A-16C illustrate an example WSI for which the nuclear morphology features of "Area," "First Order Entropy," and "RunLengthNonUniformity," respectively, are highly indicative of the degree of tumor heterogeneity possibly present in the mutational context of a gene fusion.

Figure 17A:
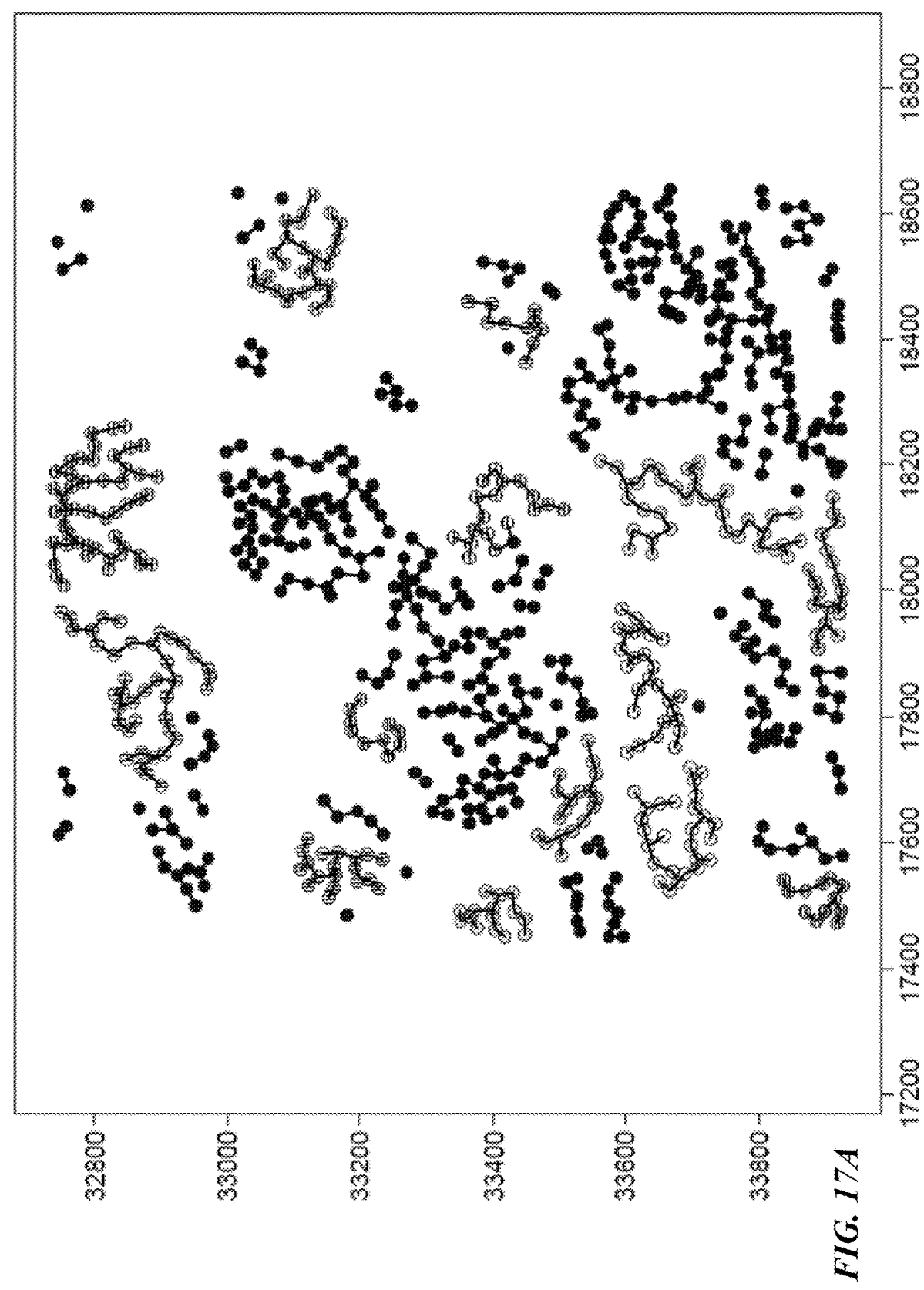
FIG. 17A illustrates a non-limiting example of identification of subgraphs of a minimum spanning tree of tumor cells depicted in a WSI.

In some embodiments, identifying tumor heterogeneity comprises identifying regions of clonal cells by conducting a cell-level spatial analysis to assess spatial distribution. In some embodiments, assessing spatial distribution comprises measuring spectral distances within subgraphs of a minimum spanning tree of tumor cells, wherein each of the subgraphs represents a cluster of adjacent cells (e.g., a tumor nest), and computing adjacency spectral distances pairwise across all of the subgraphs. FIG. 17A illustrates a non-limiting example of identification of subgraphs of a minimum spanning tree of tumor cells depicted in a WSI. After generating a minimum spanning tree connecting all cells in a field of view or WSI, subgraphs (e.g., corresponding to tumor nests) may be identified. Each subgraph may be defined by performing outlier detection and/or defined based on segmentation of detected tumor nests. Once adjacency spectral distances pairwise across all of the subgraphs, an assessment may be made regarding the spatial distribution of the tumor cells. More equidistantly distributed tumor cells may correspond to areas of homogeneous tumor cells (i.e., cells with a specific gene fusion). FIG. 17B illustrates a non-limiting example of experimental results of identification of gene fusions based on quantifying adjacency spectral distances as between the subgraphs. As shown in FIG. 17B, comparison of adjacency spectral distances across the subgraphs may provide a statistically significant distinction between gene fusions, oncogene driver mutations, and tumor suppressors and/or unknown drivers.

Figure 18A:
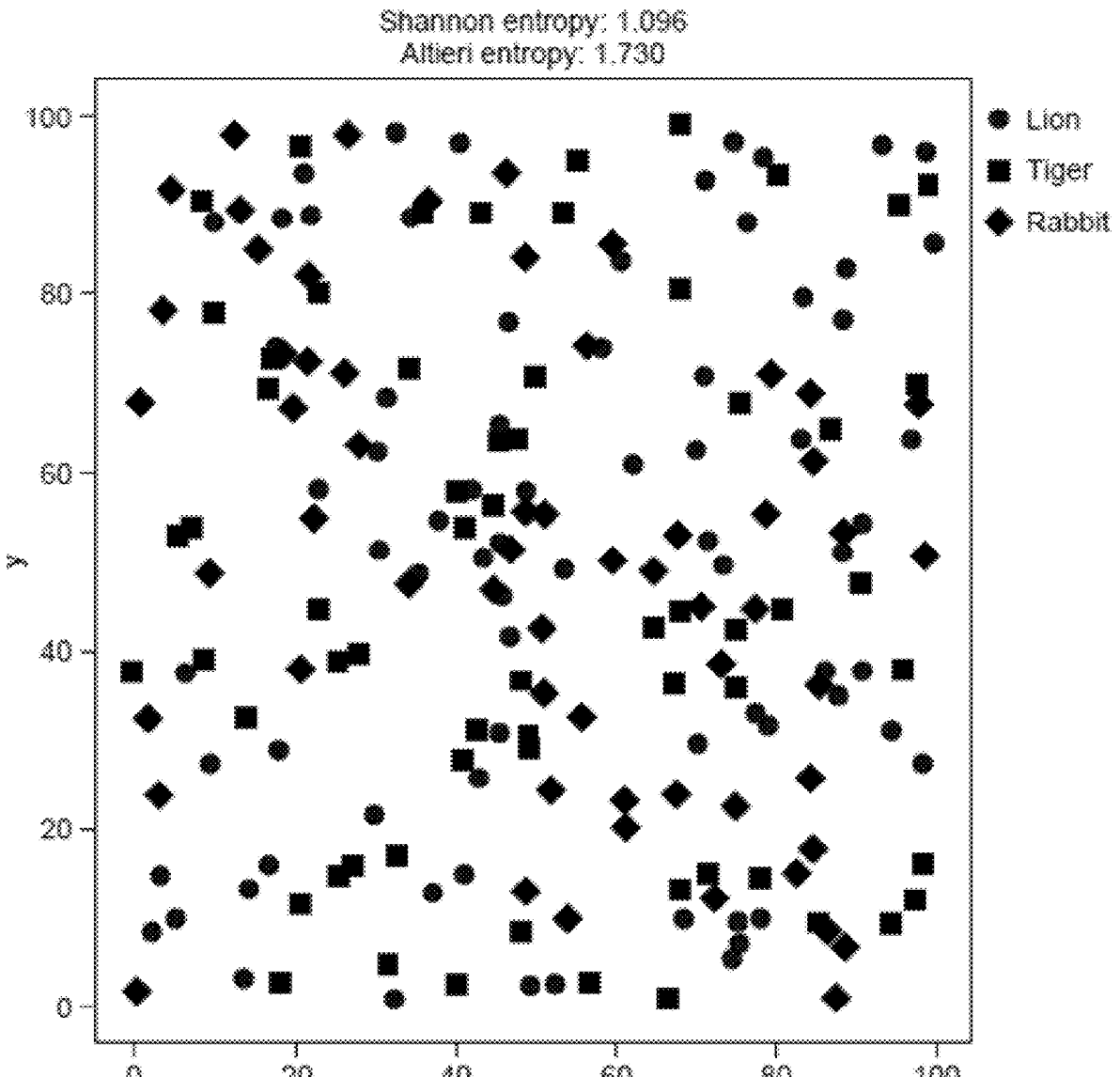
FIGS. 18A-18C illustrate non-limiting examples of spatial entropy as measured in three different distributions of tumor cell phenotypes.
Figure 18B:
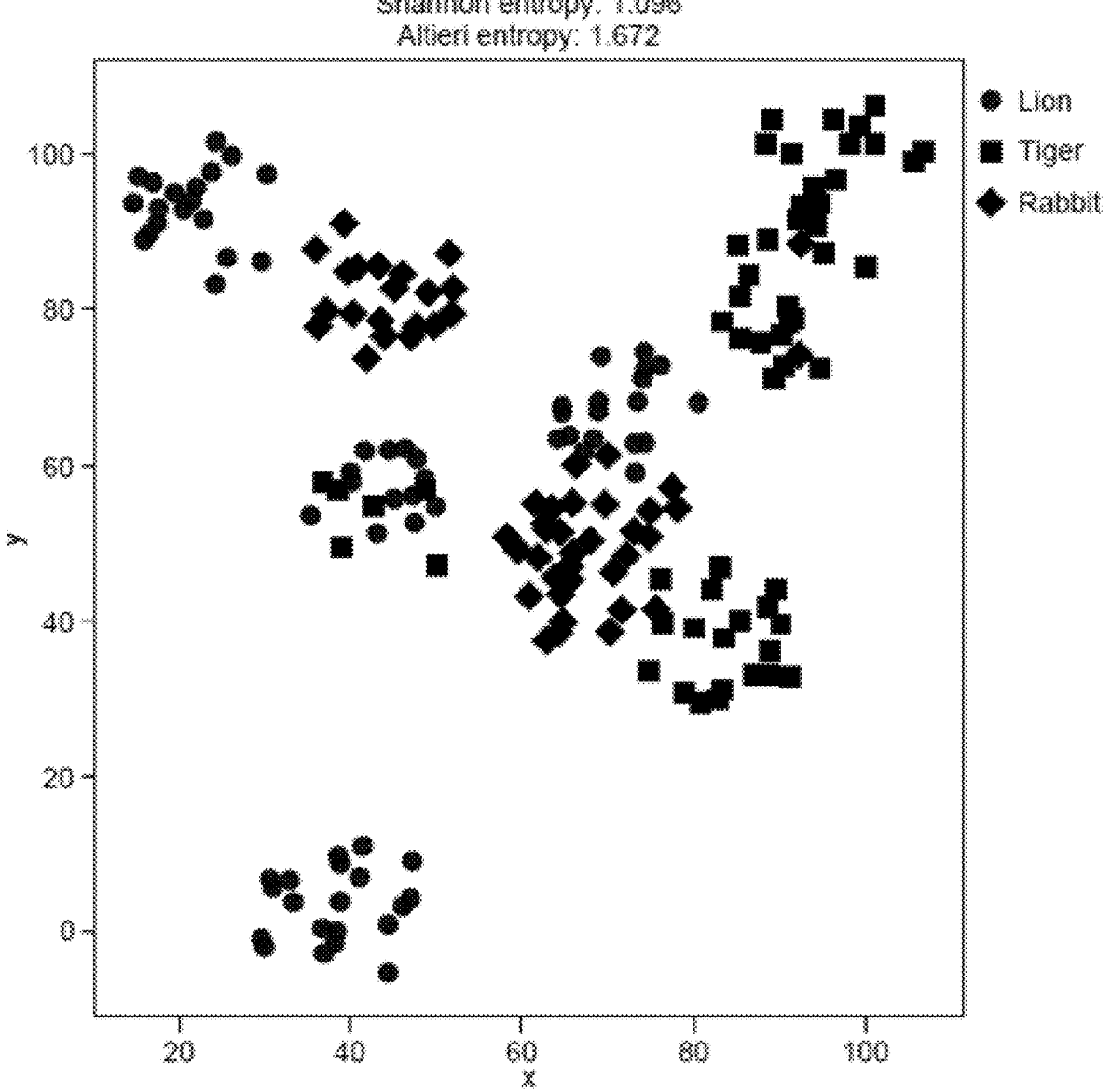
Figure 18C:
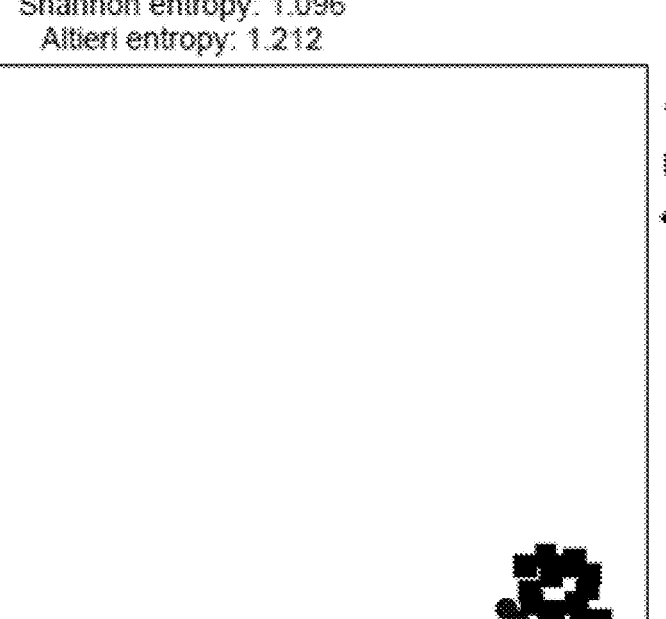

In some embodiments, identifying tumor heterogeneity comprises identifying regions of closely adjacent clonal cells by conducting a cell-level spatial analysis to assess spatial entropy. FIGS. 18A-18C illustrate non-limiting examples of spatial entropy as measured in three different distributions of tumor cell phenotypes. As shown in FIGS. 18A-18C, measures of non-spatial entropy (i.e., Shannon entropy) are unable to reflect the influence of location on heterogeneity of a distribution of occurrences, whereas spatial entropy (i.e., Altieri entropy) accurately reflects the differences in heterogeneity as between the spatially plotted occurrences along the x and y axes in FIGS. 18A-18C.

Figure 18D:
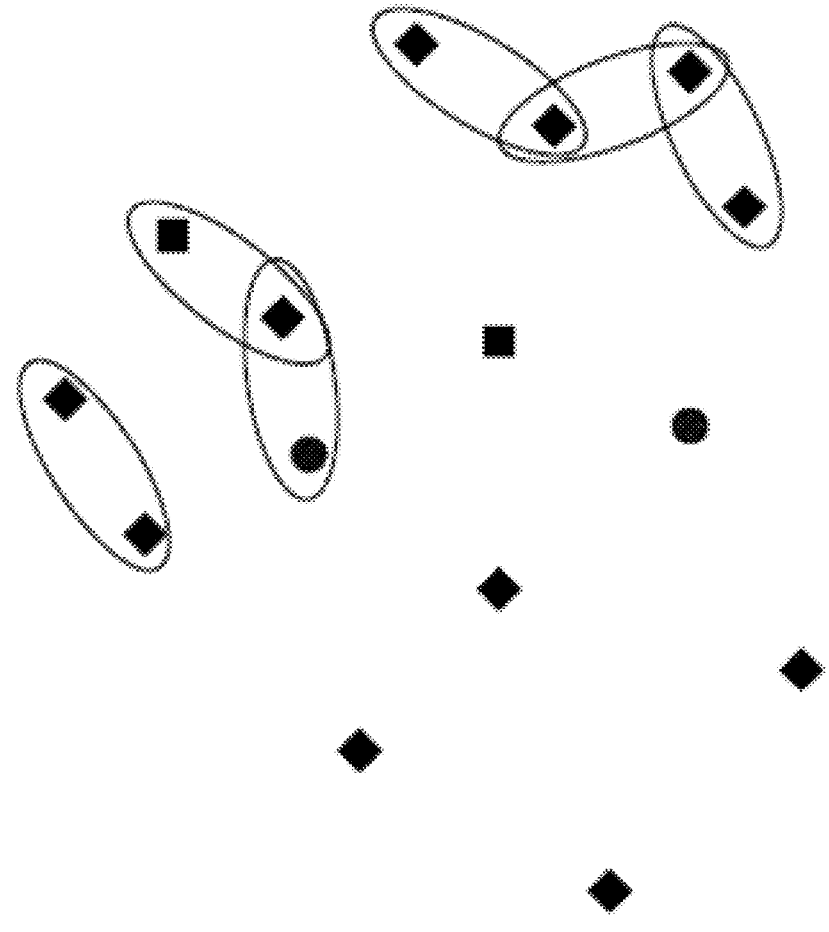
FIG. 18D is a schematic illustration of identification of pairs of tumor cells co-occurring within a specified distance and classified in a specified phenotype.

In some embodiments, assessing spatial entropy may comprise designating a set of distinct distance bins (each bin representing a range of distances between a pair of tumor cells), identifying all pairs of tumor cells belonging to each of the distance bins, computing, for each of the distance bins, a frequency of pairs of tumor cells identified as being morphologically similar, and then computing a weighted sum of all of the bin frequency values. The weight applied to each distance bin may correspond to the number of pairs of tumor cells in the distance bin. The set of distance bins may be limited to only those bins representing distance ranges with a maximum distance below a specified threshold. FIG. 18D is a schematic illustration of identification of pairs of tumor cells co-occurring within a specified distance and classified in a specified phenotype.

Figure 18E:
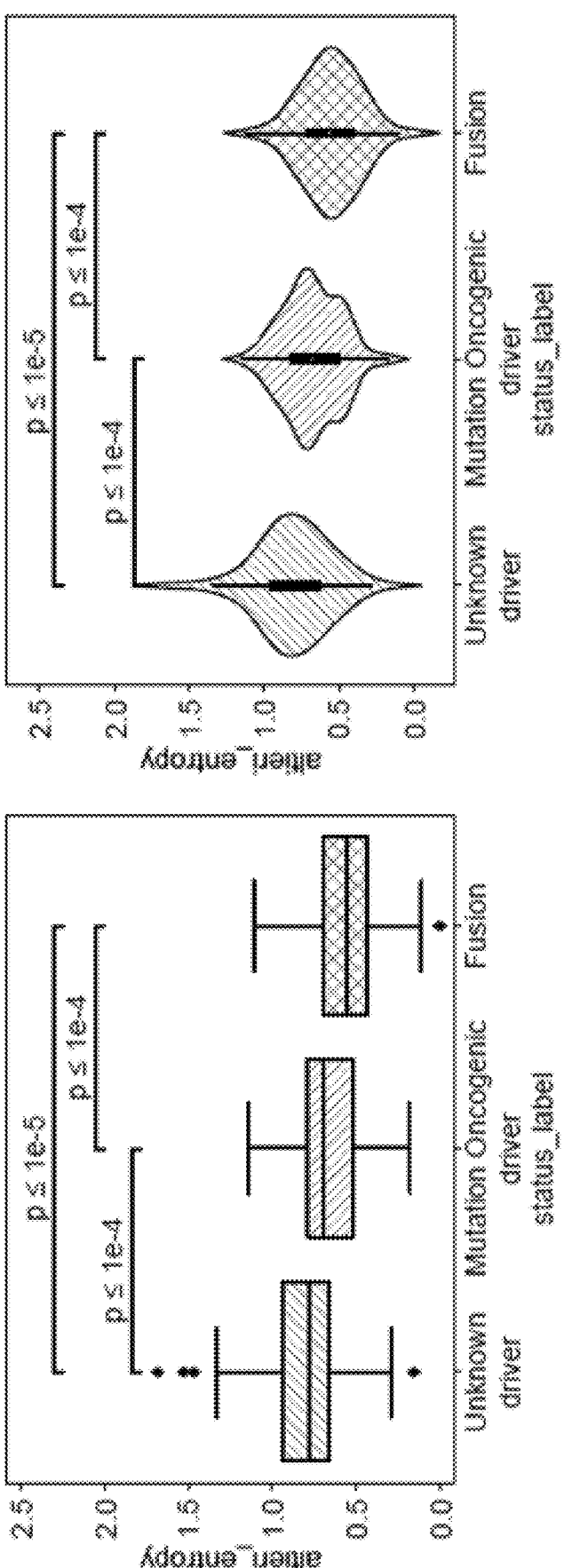
FIGS. 18E-18F illustrate non-limiting examples of experimental results of identification, based on measuring spatial entropy, of gene fusions, oncogene driver mutations, and tumor suppressors and/or unknown drivers.
Figure 18F:
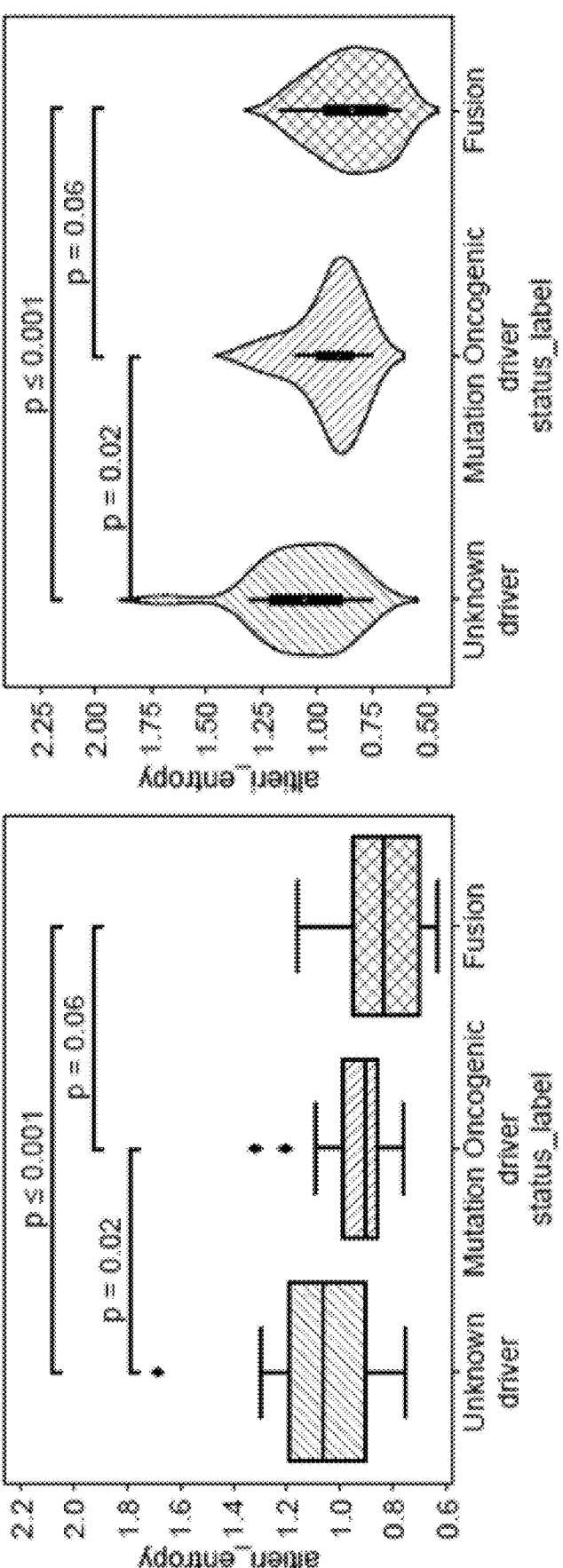

FIGS. 18E-18F illustrate non-limiting examples of experimental results of identification, based on measuring spatial entropy, of gene fusions, oncogene driver mutations, and tumor suppressors and/or unknown drivers. As shown in FIGS. 18E-18F, spatial entropy may provide a statistically significant distinction between gene fusions, oncogene driver mutations, and tumor suppressors and/or unknown drivers.

Figure 19:
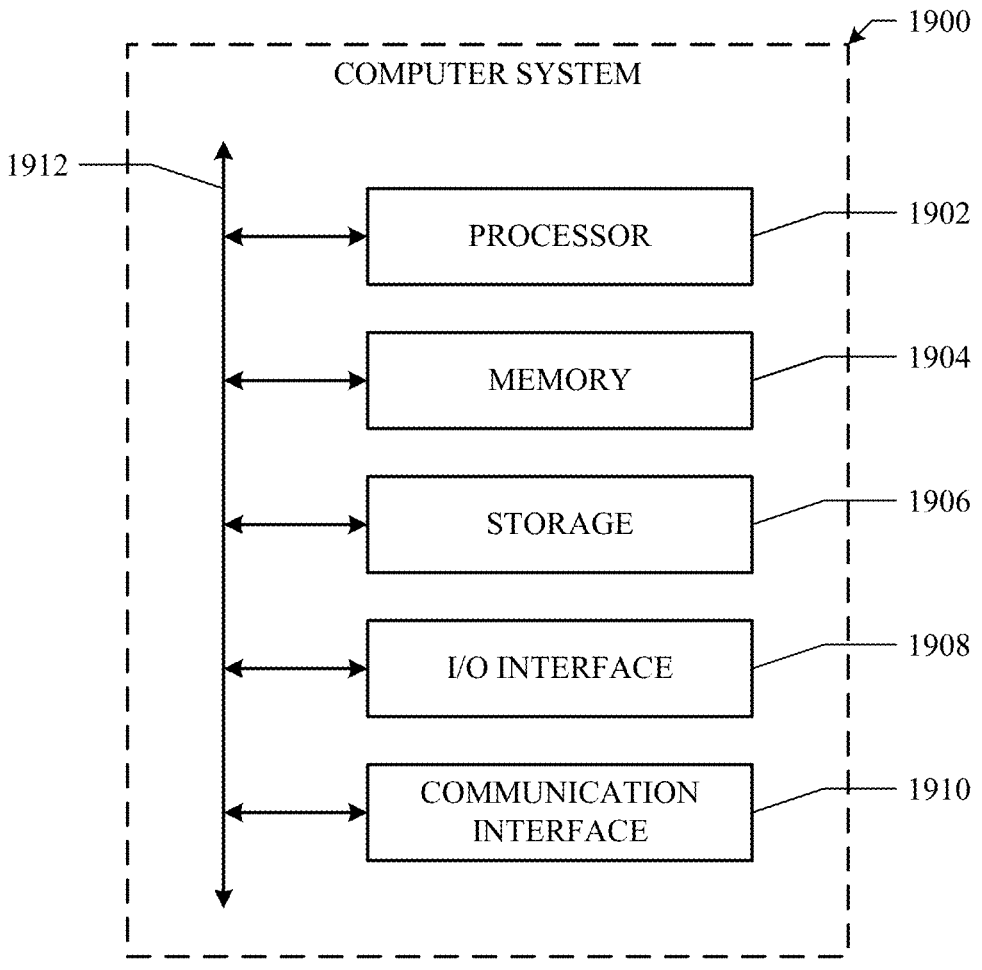
FIG. 19 illustrates an example of a computing system.

FIG. 19 illustrates an example computer system 1900. In particular embodiments, one or more computer systems 1900 perform one or more steps of one or more methods described or illustrated herein. In particular embodiments, one or more computer systems 1900 provide functionality described or illustrated herein. In particular embodiments, software running on one or more computer systems 1900 performs one or more steps of one or more methods described or illustrated herein or provides functionality described or illustrated herein. Particular embodiments include one or more portions of one or more computer systems 1900. Herein, reference to a computer system may encompass a computing device, and vice versa, where appropriate. Moreover, reference to a computer system may encompass one or more computer systems, where appropriate.

This disclosure contemplates any suitable number of computer systems 1900. This disclosure contemplates computer system 1900 taking any suitable physical form. As example and not by way of limitation, computer system 1900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1900 may include one or more computer systems 1900; be unitary or distributed; span multiple locations; span multiple machines; span multiple data centers; or reside in a cloud, which may include one or more cloud components in one or more networks. Where appropriate, one or more computer systems 1900 may perform without substantial spatial or temporal limitation one or more steps of one or more methods described or illustrated herein. As an example and not by way of limitation, one or more computer systems 1900 may perform in real time or in batch mode one or more steps of one or more methods described or illustrated herein. One or more computer systems 1900 may perform at different times or at different locations one or more steps of one or more methods described or illustrated herein, where appropriate.

In particular embodiments, computer system 1900 includes a processor 1902, memory 1904, storage 1906, an input/output (I/O) interface 1908, a communication interface 1910, and a bus 1912. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1902 includes hardware for executing instructions, such as those making up a computer program. As an example and not by way of limitation, to execute instructions, processor 1902 may retrieve (or fetch) the instructions from an internal register, an internal cache, memory 1904, or storage 1906; decode and execute them; and then write one or more results to an internal register, an internal cache, memory 1904, or storage 1906. In particular embodiments, processor 1902 may include one or more internal caches for data, instructions, or addresses. This disclosure contemplates processor 1902 including any suitable number of any suitable internal caches, where appropriate. As an example and not by way of limitation, processor 1902 may include one or more instruction caches, one or more data caches, and one or more translation lookaside buffers (TLBs). Instructions in the instruction caches may be copies of instructions in memory 1904 or storage 1906, and the instruction caches may speed up retrieval of those instructions by processor 1902. Data in the data caches may be copies of data in memory 1904 or storage 1906 for instructions executing at processor 1902 to operate on; the results of previous instructions executed at processor 1902 for access by subsequent instructions executing at processor 1902 or for writing to memory 1904 or storage 1906; or other suitable data. The data caches may speed up read or write operations by processor 1902. The TLBs may speed up virtual-address translation for processor 1902. In particular embodiments, processor 1902 may include one or more internal registers for data, instructions, or addresses. This disclosure contemplates processor 1902 including any suitable number of any suitable internal registers, where appropriate. Where appropriate, processor 1902 may include one or more arithmetic logic units (ALUs); be a multi-core processor; or include one or more processors 1902. Although this disclosure describes and illustrates a particular processor, this disclosure contemplates any suitable processor.

In particular embodiments, memory 1904 includes main memory for storing instructions for processor 1902 to execute or data for processor 1902 to operate on. As an example and not by way of limitation, computer system 1900 may load instructions from storage 1906 or another source (such as, for example, another computer system 1900) to memory 1904. Processor 1902 may then load the instructions from memory 1904 to an internal register or internal cache. To execute the instructions, processor 1902 may retrieve the instructions from the internal register or internal cache and decode them. During or after execution of the instructions, processor 1902 may write one or more results (which may be intermediate or final results) to the internal register or internal cache. Processor 1902 may then write one or more of those results to memory 1904. In particular embodiments, processor 1902 executes only instructions in one or more internal registers or internal caches or in memory 1904 (as opposed to storage 1906 or elsewhere) and operates only on data in one or more internal registers or internal caches or in memory 1904 (as opposed to storage 1906 or elsewhere). One or more memory buses (which may each include an address bus and a data bus) may couple processor 1902 to memory 1904. Bus 1912 may include one or more memory buses, as described below. In particular embodiments, one or more memory management units (MMUs) reside between processor 1902 and memory 1904 and facilitate accesses to memory 1904 requested by processor 1902. In particular embodiments, memory 1904 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1904 may include one or more memories 1904, where appropriate. Although this disclosure describes and illustrates particular memory, this disclosure contemplates any suitable memory.

In particular embodiments, storage 1906 includes mass storage for data or instructions. As an example and not by way of limitation, storage 1906 may include a hard disk drive (HDD), a floppy disk drive, flash memory, an optical disc, a magneto-optical disc, magnetic tape, or a Universal Serial Bus (USB) drive or a combination of two or more of these. Storage 1906 may include removable or non-removable (or fixed) media, where appropriate. Storage 1906 may be internal or external to computer system 1900, where appropriate. In particular embodiments, storage 1906 is non-volatile, solid-state memory. In particular embodiments, storage 1906 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1906 taking any suitable physical form. Storage 1906 may include one or more storage control units facilitating communication between processor 1902 and storage 1906, where appropriate. Where appropriate, storage 1906 may include one or more storages 1906. Although this disclosure describes and illustrates particular storage, this disclosure contemplates any suitable storage.

In particular embodiments, I/O interface 1908 includes hardware, software, or both, providing one or more interfaces for communication between computer system 1900 and one or more I/O devices. Computer system 1900 may include one or more of these I/O devices, where appropriate. One or more of these I/O devices may enable communication between a person and computer system 1900. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1908 for them. Where appropriate, I/O interface 1908 may include one or more device or software drivers enabling processor 1902 to drive one or more of these I/O devices. I/O interface 1908 may include one or more I/O interfaces 1908, where appropriate. Although this disclosure describes and illustrates a particular I/O interface, this disclosure contemplates any suitable I/O interface.

In particular embodiments, communication interface 1910 includes hardware, software, or both providing one or more interfaces for communication (such as, for example, packet-based communication) between computer system 1900 and one or more other computer systems 1900 or one or more networks. As an example and not by way of limitation, communication interface 1910 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1910 for it. As an example and not by way of limitation, computer system 1900 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1900 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1900 may include any suitable communication interface 1910 for any of these networks, where appropriate. Communication interface 1910 may include one or more communication interfaces 1910, where appropriate. Although this disclosure describes and illustrates a particular communication interface, this disclosure contemplates any suitable communication interface.

In particular embodiments, bus 1912 includes hardware, software, or both coupling components of computer system 1900 to each other. As an example and not by way of limitation, bus 1912 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1912 may include one or more buses 1912, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

EMBODIMENTS

1. A method comprising, by a digital pathology image processing system:

accessing a digital pathology image that depicts tumor cells sampled from a subject; selecting a plurality of patches from the digital pathology image, wherein each of the patches depicts tumor cells;

generating a mutation prediction for each of the patches, wherein the mutation prediction represents a prediction of a likelihood that an actionable mutation appears in the patch; and generating, based on the plurality of mutation predictions, a prognostic prediction related to one or more treatment regimens for the subject.

2. The method of Embodiment 1, wherein generating the mutation predictions comprises:

detecting one or more features from each of the plurality of patches, wherein the one or more features comprise one or more of a clinical feature or a histologic feature, and wherein generating the label for each of the plurality of patches is based on the one or more features.

3. The method of Embodiments 2 or 3, wherein generating the mutation predictions is based on tumor morphology, wherein the tumor morphology is based on an analysis of one or more of a presence of signet ring cells, a number of signet ring cells, a presence of hepatoid cells, a number of hepatoid cells, extracellular mucin, or a tumor growth pattern.

4. The method of any of Embodiments 1-3, wherein generating the mutation predictions is based on one or more machine-learning models, wherein the method further comprises training the one or more machine-learning models based on a plurality of training data comprising one or more labeled depictions of tumor cells and one or more labeled depictions of other histologic or clinical features.

5. The method of any of Embodiments 1-4, wherein generating the prognostic prediction is based on generating mutation predictions for patches from one or more additional digital pathology images, each of the one or more additional digital pathology images depicting an additional particular sample of the biological sample from the subject, and wherein the analysis comprises:

generating a mutation prediction for each of the patches from the one or more additional digital pathology images; and generating a combined prognostic prediction for the subject based on all of the mutation predictions.

6. The method of any of Embodiments 1-5, further comprising:

outputting, via a graphical user interface, the prognostic prediction, wherein the graphical user interface comprises a graphical representation of the digital pathology image, and wherein the graphical representation comprises an indication of the mutation prediction generated for each of the plurality of patches and a predicted level of confidence associated with the prognostic prediction.

7. The method of any of Embodiments 1-6, further comprising:

generating a recommendation associated with use of the one or more treatment regimens.

8. The method of any of Embodiments 1-7, wherein the particular section of the biological sample was stained with one or more stains.

9. The method of any of Embodiments 1-8, wherein generating the prognostic prediction is further based on a weighted combination of the mutation predictions generated for the patches.

10. The method of any of Embodiments 1-9, wherein generating a mutation prediction for a patch depicting tumor cells comprises:

classifying the tumor cells into phenotypes, each of the phenotypes corresponding to a different mutation class.

11. The method of Embodiment 10, wherein classifying the tumor cells into phenotypes comprises:

identifying nuclear heterogeneity in the patch; and quantifying the identified nuclear heterogeneity, wherein generating the mutation prediction is further based on the quantified nuclear heterogeneity.

12. The method of Embodiments 10 or 11, wherein generating the mutation prediction comprises:

conducting a cell-level spatial analysis to assess spatial distribution, wherein the spatial distribution indicates regions of clonal cells and the spatial arrangement of cells within each of the regions of clonal cells.

13. The method of Embodiment 12, wherein assessing spatial distribution comprises:

measuring spectral distances within subgraphs of a minimum spanning tree of the tumor cells, wherein each of the subgraphs represents a tumor nest;

computing adjacency spectral distances pairwise across all of the subgraphs.

14. The method of Embodiment 13, wherein each of the subgraphs is defined by performing outlier detection.

15. The method of Embodiments 13 or 14, wherein each of the subgraphs is defined based on segmentation of detected tumor nests.

16. The method of any of Embodiments 10-15, wherein generating the mutation prediction comprises:

identifying regions of closely adjacent clonal cells in the patch by conducting a cell-level spatial analysis to assess spatial entropy.

17. The method of Embodiment 16, wherein assessing spatial entropy comprises:

designating a set of distinct distance bins, wherein each of the distance bins corresponds to a range of distances between a pair of tumor cells;

for each of the distance bins, identifying pairs of the tumor cells, wherein the distance between the tumor cells in each of the pairs falls within the range of distances corresponding to the distance bin;

computing, for each of the distance bins, a frequency of pairs of tumor cells identified as being morphologically similar;

classifying, for each possible pair of tumor cells classified into a phenotype, the pair of tumor cells into one of a predefined number of bins, each of the bins representing a distance between spatial locations of each of the cells in the pair;

computing, for each of the bins, a frequency of classification of the pairs of tumor cells in the bin.

18. The method of Embodiment 17, wherein the weight applied to each distance bin may correspond to the number of pairs of tumor cells in the distance bin.

19. The method of Embodiments 17 or 18, wherein the set of distance bins may be limited to only those bins representing distance ranges with a maximum distance below a specified threshold 20. The method of any of Embodiments 1-19, wherein the generating the prognostic prediction comprises:

determining a mutational context of the digital pathology image to be an unknown driver or a tumor suppressor, wherein a level of heterogeneity of the cluster of tumor cells is high, and wherein the prognostic prediction is related to a treatment regimen comprising immuno- therapy.

21. The method of any of Embodiments 1-20, wherein the generating the prognostic prediction comprises:

determining a mutational context of the digital pathology image to be an oncogene driver mutation, wherein a level of heterogeneity of the cluster of tumor cells is intermediate, and wherein the prognostic prediction is related to a treatment regimen comprising a targeted therapy corresponding to a mutation.

22. The method of any of Embodiments 1-21, wherein:

if an actionable mutation appears in at least one of the patches, the one or more treatment regimens comprises a targeted therapy associated with the actionable muta- tion;

else the one or more treatment regimens comprises immu- notherapy.

23. One or more computer-readable non-transitory stor- age media embodying software that is operable when executed to:

access a digital pathology image that depicts tumor cells sampled from a subject;

select a plurality of patches from the digital pathology image, wherein each of the patches depicts tumor cells;

generate a mutation prediction for each of the patches, wherein the mutation prediction represents a prediction of a likelihood that an actionable mutation appears in the patch; and generate, based on the plurality of mutation predictions, a prognostic prediction related to one or more treatment regimens for the subject.

24. The computer-readable non-transitory storage media of Embodiment 23, wherein generating the mutation pre- dictions comprises:

detecting one or more features from each of the plurality of patches, wherein the one or more features comprise one or more of a clinical feature or a histologic feature, and wherein generating the label for each of the plu- rality of patches is based on the one or more features.

25. The computer-readable non-transitory storage media of Embodiments 23 or 24, wherein generating the mutation predictions is based on tumor morphology, wherein the tumor morphology is based on an analysis of one or more of a presence of signet ring cells, a number of signet ring cells, a presence of hepatoid cells, a number of hepatoid cells, extracellular mucin, or a tumor growth pattern.

26. The computer-readable non-transitory storage media of any of Embodiments 23-25, wherein generating the mutation predictions is based on one or more machine- learning models, wherein the computer-readable non-tran- sitory storage media further comprises training the one or more machine-learning models based on a plurality of training data comprising one or more labeled depictions of tumor cells and one or more labeled depictions of other histologic or clinical features.

27. The computer-readable non-transitory storage media of any of Embodiments 23-26, wherein generating the prognostic prediction is based on generating mutation pre- dictions for patches from one or more additional digital pathology images, each of the one or more additional digital pathology images depicting an additional particular sample of the biological sample from the subject, and wherein the analysis comprises:

generating a mutation prediction for each of the patches from the one or more additional digital pathology images; and generating a combined prognostic prediction for the sub- ject based on all of the mutation predictions.

28. The computer-readable non-transitory storage media of any of Embodiments 23-27, further comprising:

outputting, via a graphical user interface, the prognostic prediction, wherein the graphical user interface com- prises a graphical representation of the digital pathol- ogy image, and wherein the graphical representation comprises an indication of the mutation prediction generated for each of the plurality of patches and a predicted level of confidence associated with the prog- nostic prediction.

29. The computer-readable non-transitory storage media of any of Embodiments 23-28, further comprising:

generating a recommendation associated with use of the one or more treatment regimens.

30. The computer-readable non-transitory storage media of any of Embodiments 23-29, wherein the particular section of the biological sample was stained with one or more stains.

31. The computer-readable non-transitory storage media of any of Embodiments 23-30, wherein generating the prognostic prediction is further based on a weighted com- bination of the mutation predictions generated for the patches.

32. The computer-readable non-transitory storage media of any of Embodiments 23-31, wherein generating a muta- tion prediction for a patch depicting tumor cells comprises:

classifying the tumor cells into phenotypes, each of the phenotypes corresponding to a different mutation class.

33. The computer-readable non-transitory storage media of Embodiment 32, wherein classifying the tumor cells into phenotypes comprises:

identifying nuclear heterogeneity in the patch; and quantifying the identified nuclear heterogeneity, wherein generating the mutation prediction is further based on the quantified nuclear heterogeneity.

34. The computer-readable non-transitory storage media of Embodiments 32 or 33, wherein generating the mutation prediction comprises:

conducting a cell-level spatial analysis to assess spatial distribution, wherein the spatial distribution indicates regions of clonal cells and the spatial arrangement of cells within each of the regions of clonal cells.

35. The computer-readable non-transitory storage media of Embodiment 34, wherein assessing spatial distribution comprises:

measuring spectral distances within subgraphs of a mini- mum spanning tree of the tumor cells, wherein each of the subgraphs represents a tumor nest;

computing adjacency spectral distances pairwise across all of the subgraphs.

36. The computer-readable non-transitory storage media of Embodiment 35, wherein each of the subgraphs is defined by performing outlier detection.

37. The computer-readable non-transitory storage media of Embodiments 35 or 36, wherein each of the subgraphs is defined based on segmentation of detected tumor nests.

38. The computer-readable non-transitory storage media of any of Embodiments 32-37, wherein generating the mutation prediction comprises:

identifying regions of closely adjacent clonal cells in the patch by conducting a cell-level spatial analysis to assess spatial entropy.

39. The computer-readable non-transitory storage media of Embodiment 38, wherein assessing spatial entropy comprises:

designating a set of distinct distance bins, wherein each of the distance bins corresponds to a range of distances between a pair of tumor cells;

for each of the distance bins, identifying pairs of the tumor cells, wherein the distance between the tumor cells in each of the pairs falls within the range of distances corresponding to the distance bin;

computing, for each of the distance bins, a frequency of pairs of tumor cells identified as being morphologically similar;

classifying, for each possible pair of tumor cells classified into a phenotype, the pair of tumor cells into one of a predefined number of bins, each of the bins representing a distance between spatial locations of each of the cells in the pair;

computing, for each of the bins, a frequency of classification of the pairs of tumor cells in the bin.

40. The computer-readable non-transitory storage media of Embodiment 39, wherein the weight applied to each distance bin may correspond to the number of pairs of tumor cells in the distance bin.

41. The computer-readable non-transitory storage media of Embodiments 39 or 40, wherein the set of distance bins may be limited to only those bins representing distance ranges with a maximum distance below a specified threshold 42. The computer-readable non-transitory storage media of any of Embodiments 23-41, wherein the generating the prognostic prediction comprises:

determining a mutational context of the digital pathology image to be an unknown driver or a tumor suppressor, wherein a level of heterogeneity of the cluster of tumor cells is high, and wherein the prognostic prediction is related to a treatment regimen comprising immunotherapy.

43. The computer-readable non-transitory storage media of any of Embodiments 23-42, wherein the generating the prognostic prediction comprises:

determining a mutational context of the digital pathology image to be an oncogene driver mutation, wherein a level of heterogeneity of the cluster of tumor cells is intermediate, and wherein the prognostic prediction is related to a treatment regimen comprising a targeted therapy corresponding to a mutation.

44. The computer-readable non-transitory storage media of any of Embodiments 23-43, wherein:

if an actionable mutation appears in at least one of the patches, the one or more treatment regimens comprises a targeted therapy associated with the actionable mutation;

else the one or more treatment regimens comprises immunotherapy.

45. A system comprising: one or more processors; and a non-transitory memory coupled to the processors comprising instructions executable by the processors, the processors operable when executing the instructions to:

access a digital pathology image that depicts tumor cells sampled from a subject;

select a plurality of patches from the digital pathology image, wherein each of the patches depicts tumor cells;

generate a mutation prediction for each of the patches, wherein the mutation prediction represents a prediction of a likelihood that an actionable mutation appears in the patch; and generate, based on the plurality of mutation predictions, a prognostic prediction related to one or more treatment regimens for the subject.

46. The system of Embodiment 45, wherein generating the mutation predictions comprises:

detecting one or more features from each of the plurality of patches, wherein the one or more features comprise one or more of a clinical feature or a histologic feature, and wherein generating the label for each of the plurality of patches is based on the one or more features.

47. The system of Embodiments 45 or 46, wherein generating the mutation predictions is based on tumor morphology, wherein the tumor morphology is based on an analysis of one or more of a presence of signet ring cells, a number of signet ring cells, a presence of hepatoid cells, a number of hepatoid cells, extracellular mucin, or a tumor growth pattern.

48. The system of any of Embodiments 45-47, wherein generating the mutation predictions is based on one or more machine-learning models, wherein the system further comprises training the one or more machine-learning models based on a plurality of training data comprising one or more labeled depictions of tumor cells and one or more labeled depictions of other histologic or clinical features.

49. The system of any of Embodiments 45-48, wherein generating the prognostic prediction is based on generating mutation predictions for patches from one or more additional digital pathology images, each of the one or more additional digital pathology images depicting an additional particular sample of the biological sample from the subject, and wherein the analysis comprises:

generating a mutation prediction for each of the patches from the one or more additional digital pathology images; and generating a combined prognostic prediction for the subject based on all of the mutation predictions.

50. The system of any of Embodiments 45-49, further comprising:

outputting, via a graphical user interface, the prognostic prediction, wherein the graphical user interface comprises a graphical representation of the digital pathology image, and wherein the graphical representation comprises an indication of the mutation prediction generated for each of the plurality of patches and a predicted level of confidence associated with the prognostic prediction.

51. The system of any of Embodiments 45-50, further comprising:

generating a recommendation associated with use of the one or more treatment regimens.

52. The system of any of Embodiments 45-51, wherein the particular section of the biological sample was stained with one or more stains.

53. The system of any of Embodiments 45-52, wherein generating the prognostic prediction is further based on a weighted combination of the mutation predictions generated for the patches.

54. The system of any of Embodiments 45-53, wherein generating a mutation prediction for a patch depicting tumor cells comprises:

classifying the tumor cells into phenotypes, each of the phenotypes corresponding to a different mutation class.

55. The system of Embodiment 54, wherein classifying the tumor cells into phenotypes comprises:

identifying nuclear heterogeneity in the patch; and quantifying the identified nuclear heterogeneity, wherein generating the mutation prediction is further based on the quantified nuclear heterogeneity.

56. The system of Embodiments 54 or 55, wherein generating the mutation prediction comprises:

conducting a cell-level spatial analysis to assess spatial distribution, wherein the spatial distribution indicates regions of clonal cells and the spatial arrangement of cells within each of the regions of clonal cells.

57. The system of Embodiment 56, wherein assessing spatial distribution comprises:

measuring spectral distances within subgraphs of a minimum spanning tree of the tumor cells, wherein each of the subgraphs represents a tumor nest;

computing adjacency spectral distances pairwise across all of the subgraphs.

58. The system of Embodiment 57, wherein each of the subgraphs is defined by performing outlier detection.

59. The system of Embodiments 57 or 58, wherein each of the subgraphs is defined based on segmentation of detected tumor nests.

60. The system of any of Embodiments 54-59, wherein generating the mutation prediction comprises:

identifying regions of closely adjacent clonal cells in the patch by conducting a cell-level spatial analysis to assess spatial entropy.

61. The system of Embodiment 60, wherein assessing spatial entropy comprises:

designating a set of distinct distance bins, wherein each of the distance bins corresponds to a range of distances between a pair of tumor cells;

for each of the distance bins, identifying pairs of the tumor cells, wherein the distance between the tumor cells in each of the pairs falls within the range of distances corresponding to the distance bin;

computing, for each of the distance bins, a frequency of pairs of tumor cells identified as being morphologically similar;

classifying, for each possible pair of tumor cells classified into a phenotype, the pair of tumor cells into one of a predefined number of bins, each of the bins representing a distance between spatial locations of each of the cells in the pair;

computing, for each of the bins, a frequency of classification of the pairs of tumor cells in the bin.

62. The system of Embodiment 61, wherein the weight applied to each distance bin may correspond to the number of pairs of tumor cells in the distance bin.

63. The system of Embodiments 61 or 62, wherein the set of distance bins may be limited to only those bins representing distance ranges with a maximum distance below a specified threshold 64. The system of any of Embodiments 45-63, wherein the generating the prognostic prediction comprises:

determining a mutational context of the digital pathology image to be an unknown driver or a tumor suppressor, wherein a level of heterogeneity of the cluster of tumor cells is high, and wherein the prognostic prediction is related to a treatment regimen comprising immunotherapy.

65. The system of any of Embodiments 45-64, wherein the generating the prognostic prediction comprises:

determining a mutational context of the digital pathology image to be an oncogene driver mutation, wherein a level of heterogeneity of the cluster of tumor cells is intermediate, and wherein the prognostic prediction is related to a treatment regimen comprising a targeted therapy corresponding to a mutation.

66. The system of any of Embodiments 45-65, wherein:

if an actionable mutation appears in at least one of the patches, the one or more treatment regimens comprises a targeted therapy associated with the actionable mutation;

else the one or more treatment regimens comprises immunotherapy.

What is claimed is:

1. A method comprising, by a digital pathology image processing system:

accessing a digital pathology image that depicts tumor cells sampled from a subject;

selecting a plurality of patches from the digital pathology image, wherein each of the patches depicts tumor cells;

generating a mutation prediction for each of the patches, wherein the mutation prediction is based at least in part on a relationship between one or more detected image-based features in a respective patch and one or more actionable mutations, and represents a prediction of a likelihood that an actionable mutation appears in the respective patch; and generating, based on the plurality of mutation predictions, a prognostic prediction related to one or more treatment regimens for the subject.

2. The method of claim 1, wherein generating the mutation predictions comprises:

detecting one or more image-based features from each of the plurality of patches, wherein the one or more features comprise one or more of a clinical feature and a histologic feature.

3. The method of claim 1, wherein generating the mutation predictions is based on tumor morphology, and wherein the tumor morphology is based on an analysis of one or more of a presence of signet ring cells, a number of signet ring cells, a presence of hepatoid cells, a number of hepatoid cells, extracellular mucin, and a tumor growth pattern.

4. The method of claim 1, wherein generating the mutation predictions is based on one or more machine-learning models, wherein the method further comprises training the one or more machine-learning models based on a plurality of training data comprising one or more labeled depictions of tumor cells and one or more labeled depictions of other histologic or clinical features.

5. The method of claim 1, wherein generating the prognostic prediction is based on generating mutation predictions for patches from one or more additional digital pathology images, each of the one or more additional digital pathology images depicting an additional sample of the tumor cells sampled from the subject, and wherein the analysis comprises:

generating a mutation prediction for each of the patches from the one or more additional digital pathology images; and generating a combined prognostic prediction for the subject based on all of the mutation predictions.

6. The method of claim 1, further comprising:

outputting, via a graphical user interface, the prognostic prediction, wherein the graphical user interface comprises a graphical representation of the digital pathology image, and wherein the graphical representation comprises an indication of the mutation prediction generated for each of the plurality of patches and a predicted level of confidence associated with the prognostic prediction; and generating a recommendation associated with use of the one or more treatment regimens.

7. The method of claim 1, wherein the tumor cells sampled from the subject are stained with one or more stains.

8. The method of claim 1, wherein generating the prognostic prediction is further based on a weighted combination of the mutation predictions generated for the patches.

9. The method of claim 1, wherein generating a mutation prediction for a patch depicting tumor cells comprises:

classifying the tumor cells into phenotypes, each of the phenotypes corresponding to a different mutation class.

10. The method of claim 9, wherein classifying the tumor cells into phenotypes comprises:

identifying nuclear heterogeneity in the patch; and quantifying the identified nuclear heterogeneity, wherein generating the mutation prediction is further based on the quantified nuclear heterogeneity.

11. The method of claim 9, wherein generating the mutation prediction comprises:

conducting a cell-level spatial analysis to assess spatial distribution, wherein the spatial distribution indicates regions of clonal cells and a spatial arrangement of cells within each of the regions of clonal cells.

12. The method of claim 11, wherein assessing spatial distribution comprises:

measuring spectral distances within subgraphs of a minimum spanning tree of the tumor cells, wherein each of the subgraphs represents a tumor nest; and computing adjacency spectral distances pairwise across all of the subgraphs.

13. The method of claim 12, wherein each of the subgraphs is defined by performing outlier detection and/or based on segmentation of detected tumor nests.

14. The method of claim 9, wherein generating the mutation prediction comprises:

identifying regions of adjacent clonal cells in the patch by conducting a cell-level spatial analysis to assess spatial entropy.

15. The method of claim 14, wherein assessing spatial entropy comprises:

designating a set of distinct distance bins, wherein each of the distance bins corresponds to a range of distances between a pair of tumor cells;

for each of the distance bins, identifying pairs of the tumor cells, wherein the distance between the tumor cells in each of the pairs falls within the range of distances corresponding to the distance bin;

computing, for each of the distance bins, a frequency of pairs of tumor cells identified as being not morphologically heterogenous;

classifying, for each possible pair of tumor cells classified into a phenotype, the pair of tumor cells into one of a predefined number of bins, each of the bins representing a distance between spatial locations of each of the cells in the pair; and computing, for each of the bins, a frequency of classification of the pairs of tumor cells in the bin, wherein a weight applied to each of the distance bins corresponds to a number of the pairs of the tumor cells in the distance bin, and wherein the set of distance bins comprises a plurality of bins representing distance ranges with a maximum distance below a specified threshold.

16. The method of claim 1, wherein the generating the prognostic prediction comprises:

determining a mutational context of the digital pathology image to be an unknown driver or a tumor suppressor, wherein a cluster of tumor cells is heterogenous, and wherein the prognostic prediction is related to a treatment regimen comprising immunotherapy.

17. The method of claim 1, wherein the generating the prognostic prediction comprises:

determining a mutational context of the digital pathology image to be an oncogene driver mutation, wherein a cluster of tumor cells is heterogenous, and wherein the prognostic prediction is related to a treatment regimen comprising a targeted therapy corresponding to a mutation.

18. The method of claim 1, wherein:

if an actionable mutation appears in at least one of the patches, the one or more treatment regimens comprises a targeted therapy associated with the actionable mutation;

else the one or more treatment regimens comprises immunotherapy.

19. One or more computer-readable non-transitory storage media embodying software that is operable when executed to:

access a digital pathology image that depicts tumor cells sampled from a subject;

select a plurality of patches from the digital pathology image, wherein each of the patches depicts tumor cells;

generate a mutation prediction for each of the patches, wherein the mutation prediction is based at least in part on a relationship between one or more detected image-based features in a respective patch and one or more actionable mutations, and represents a prediction of a likelihood that an actionable mutation appears in the respective patch; and generate, based on the plurality of mutation predictions, a prognostic prediction related to one or more treatment regimens for the subject.

20. A system comprising: one or more processors; and a non-transitory memory coupled to the processors comprising instructions executable by the processors, the processors operable when executing the instructions to:

access a digital pathology image that depicts tumor cells sampled from a subject;

select a plurality of patches from the digital pathology image, wherein each of the patches depicts tumor cells;

generate a mutation prediction for each of the patches, wherein the mutation prediction is based at least in part on a relationship between one or more detected image-based features in a respective patch and one or more actionable mutations, and represents a prediction of a likelihood that an actionable mutation appears in the respective patch; and generate, based on the plurality of mutation predictions, a prognostic prediction related to one or more treatment regimens for the subject.

* * * * *